(12) United States Patent
Campbell

(10) Patent No.: US 11,019,818 B2
(45) Date of Patent: Jun. 1, 2021

(54) HERBICIDAL 3-SUBSTITUTED LACTAMS

(71) Applicant: FMC Corporation, Philadelphia, PA (US)

(72) Inventor: Matthew James Campbell, Flemington, NJ (US)

(73) Assignee: FMC Corporation, Philadelphia, PA (US)

(*) Notice: Subject to any disclaimer, the term of this patent is extended or adjusted under 35 U.S.C. 154(b) by 0 days.

(21) Appl. No.: 16/615,890

(22) PCT Filed: May 30, 2018

(86) PCT No.: PCT/US2018/035017
§ 371 (c)(1),
(2) Date: Nov. 22, 2019

(87) PCT Pub. No.: WO2018/222647
PCT Pub. Date: Dec. 6, 2018

(65) Prior Publication Data
US 2020/0120931 A1     Apr. 23, 2020

Related U.S. Application Data

(60) Provisional application No. 62/512,685, filed on May 30, 2017.

(51) Int. Cl.
| | | |
|---|---|---|
| *A01N 43/36* | (2006.01) | |
| *A01N 43/40* | (2006.01) | |
| *A01N 43/54* | (2006.01) | |
| *A01N 43/60* | (2006.01) | |
| *C07D 207/24* | (2006.01) | |
| *C07D 401/04* | (2006.01) | |
| *C07D 403/04* | (2006.01) | |
| *C07D 405/04* | (2006.01) | |
| *C07D 409/04* | (2006.01) | |

(52) U.S. Cl.
CPC ............. *A01N 43/36* (2013.01); *A01N 43/40* (2013.01); *A01N 43/54* (2013.01); *A01N 43/60* (2013.01); *C07D 207/24* (2013.01); *C07D 401/04* (2013.01); *C07D 403/04* (2013.01); *C07D 405/04* (2013.01); *C07D 409/04* (2013.01)

(58) Field of Classification Search
None
See application file for complete search history.

(56) References Cited

U.S. PATENT DOCUMENTS

| | | |
|---|---|---|
| 3,741,989 A | 6/1973 | Zaugg |
| 3,959,481 A | 5/1976 | Davis et al. |
| 4,594,094 A | 6/1986 | Kollmeyer |
| 4,874,422 A | 10/1989 | Woolard |
| 5,196,534 A | 3/1993 | Whitehead et al. |
| 5,856,273 A | 1/1999 | Kay et al. |
| 7,205,318 B2 | 4/2007 | Qiao et al. |
| 7,355,053 B2 | 4/2008 | Reinhard et al. |
| 7,375,232 B2 | 5/2008 | Clark et al. |
| 8,293,926 B2 | 10/2012 | Yasuoka et al. |
| 8,461,202 B2 | 6/2013 | Sancho Sanz et al. |
| 8,575,154 B2 | 11/2013 | Kori et al. |
| 8,946,216 B2 | 2/2015 | Deng et al. |
| 9,119,397 B2 | 9/2015 | Yerkes et al. |
| 9,446,995 B2 | 9/2016 | Chong |
| 9,737,073 B2 | 8/2017 | Gifford et al. |

(Continued)

FOREIGN PATENT DOCUMENTS

| | | |
|---|---|---|
| CN | 102531918 | 10/2013 |
| DE | 1262277 | 3/1968 |

(Continued)

OTHER PUBLICATIONS

Murata et al.; "Oxidation of N-Acyl-Pyrrolidines and -Piperidines with Iron(II)-Hydrogen Peroxide and an Iron Complex-Molecular Oxygen"; J. Chem. Soc. Perkin Trans.; 1987; 1259-1262. (XP055297105).

Banerjee et al., "A Stereoselective Cyclization Strategy for the Preparation of gamma-Lactams and Their Use in the Synthesis of alpha-Methyl-beta-Proline", J. Org. Chem. 2012, vol. 77, pp. 10925-10930.

Campaigne et el.; Synthesis of Some Ureidodihydrofurans and Related Pyrimidones as Potential Antimalarials; J. Med. Chem.; 1969; 339-342. (XP002278920).

(Continued)

*Primary Examiner* — Alton N Pryor
(74) *Attorney, Agent, or Firm* — Reed A Coats; FMC Corporation

(57) ABSTRACT

This disclosure relates, in part, to compounds of Formula 1 (including all stereoisomers), N-oxides of such compounds, and salts of such compounds and N-oxides:

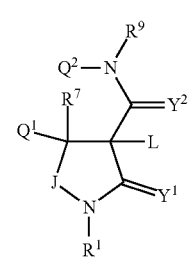

wherein L, $Y^1$, $R^1$, J, $Q^1$, $R^7$, $Y^2$, $R^9$ and $Q^2$ are as defined in the disclosure.

Also disclosed are compositions containing the compounds of Formula 1 and methods for controlling undesired vegetation comprising contacting the undesired vegetation or its environment with an effective amount of a compound or a composition of the invention.

11 Claims, No Drawings

(56) References Cited

U.S. PATENT DOCUMENTS

| | | | |
|---|---|---|---|
| 9,944,602 B2 | 4/2018 | Satterfield et al. | |
| 9,969,728 B2 | 5/2018 | Defays et al. | |
| 10,227,286 B2 | 3/2019 | Satterfield | |
| 10,294,202 B2 * | 5/2019 | Satterfield | C07D 401/12 |
| 10,405,547 B2 | 9/2019 | Satterfield et al. | |
| 10,442,807 B2 | 10/2019 | Campbell | |
| 2004/0242671 A1 | 12/2004 | Grimee et al. | |
| 2007/0123508 A1 | 5/2007 | Olsson et al. | |
| 2009/0203694 A1 | 8/2009 | Hurley et al. | |
| 2011/0218199 A1 | 9/2011 | Georges et al. | |
| 2015/0173371 A1 | 6/2015 | Mann et al. | |
| 2016/0137639 A1 | 5/2016 | Kotoku et al. | |
| 2018/0049437 A1 | 2/2018 | Satterfield et al. | |
| 2018/0057442 A1 | 3/2018 | Satterfield | |
| 2018/0077931 A1 | 3/2018 | Stevenson et al. | |
| 2018/0099935 A1 | 4/2018 | Satterfield et al. | |
| 2018/0141904 A1 | 5/2018 | Campbell et al. | |
| 2018/0213788 A1 | 8/2018 | Satterfield et al. | |
| 2020/0010446 A1 | 1/2020 | Chen | |
| 2020/0115337 A1 | 4/2020 | Campbell | |
| 2020/0154709 A1 | 5/2020 | McMahon | |

FOREIGN PATENT DOCUMENTS

| | | |
|---|---|---|
| EP | 2336104 | 6/2011 |
| IN | 1462DEL08 | 6/2008 |
| JP | 53-056288 | 5/1978 |
| JP | 54-088114 | 7/1979 |
| JP | 08-269145 | 10/1996 |
| KR | 20130142477 | 12/2013 |
| RU | 2555370 | 7/2015 |
| WO | 200009481 | 2/2000 |
| WO | 2004046081 | 6/2004 |
| WO | 2006081562 | 8/2006 |
| WO | 2009062371 | 5/2009 |
| WO | 20120034957 | 3/2012 |
| WO | 20150084796 | 6/2015 |
| WO | 20160003997 | 1/2016 |
| WO | 20160094117 | 6/2016 |
| WO | 20160164201 | 10/2016 |
| WO | 2016182780 | 11/2016 |
| WO | 20160176082 | 11/2016 |
| WO | 20160196019 | 12/2016 |
| WO | 20160196593 | 12/2016 |
| WO | 20170023515 | 2/2017 |
| WO | 2017075559 | 5/2017 |
| WO | 20180118384 | 6/2018 |
| WO | 2018/175226 | 9/2018 |
| WO | 20180175231 | 9/2018 |
| WO | 2018222646 | 12/2018 |

OTHER PUBLICATIONS

Cauliez et al.; "Studies on Pyrrolidinones On the Carbamoylation of Some Pyroglutamic Derivatives"; J. Het. Chem.; 33; 1996; 1233-123T (XP055297107).

Hajra, S. et al., "Organocatalytic Enantioselective Conjugate Addition of Nitromethane to Alkylidinemalonates: Asymmetric Synthesis of Pyrrolidine-3-Carboxylic Acid Derivatives", RSC Advances, 2013, 3, 10185-10188.

Hwang et al.; "Diastereoselective Synthesis of Oxazolidinone Derivatives and Their Antifungal Activities"; Korean J. Of Med. Chem.; vol. 4, No. 1; 1994; 52-56. (XP009191451).

IPCOM000241978D; Jun. 11, 2015.

PubChem Entry Cid 29937915 (4S)-4[3-(trifluoromethyl)phenyl]pyrolidin-2-one: May 28, 2009.

Nang et al., "Asymmetric Cyanation of Activated Olefins with Ethyl Cyanoformate Catalyzed by a Modular Titanium catalyst", Org. Lett., 2010, vol. 12(6), pp. 1280-1283.

KP002734980; Jan. 20, 2002.
KP002734981; W00009481; Feb. 24, 2000.
KP002759805; Jan. 20, 2002.
KP002759806; Mar. 23, 2009.

International Search Report and Written Opinion dated Aug. 8, 2018 pertaining to corresponding PCT/US2018/035017 patent application.

* cited by examiner

HERBICIDAL 3-SUBSTITUTED LACTAMS

FIELD OF THE INVENTION

This invention relates to certain herbicidal 3-substituted lactams, their N-oxides, salts and compositions, and methods of their use for controlling undesirable vegetation.

BACKGROUND OF THE INVENTION

The control of undesired vegetation is extremely important in achieving high crop efficiency. Achievement of selective control of the growth of weeds especially in such useful crops as rice, soybean, sugar beet, maize, potato, wheat, barley, tomato and plantation crops, among others, is very desirable. Unchecked weed growth in such useful crops can cause significant reduction in productivity and thereby result in increased costs to the consumer. The control of undesired vegetation in noncrop areas is also important. Many products are commercially available for these purposes, but the need continues for new compounds that are more effective, less costly, less toxic, environmentally safer or have different sites of action. WO 2015/084796, WO 2016/003997 and WO 2016/196593 disclose cyclic amides as herbicides. The compounds of the present invention are distinct from the compounds described in these application publications. The herbicidal 3-substituted lactams of the present invention are not disclosed in these publications.

SUMMARY OF THE INVENTION

This disclosure relates, in part, to compounds of Formula 1 (including all stereoisomers), N-oxides of such compounds, and salts of such compounds and N-oxides:

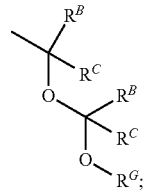

1 wherein
L is selected from

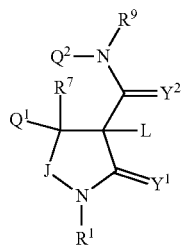

L-1

L-2

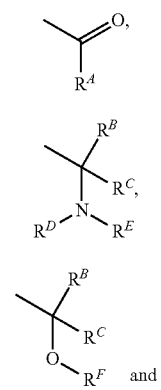

L-3 and

L-4

$R^A$ is $C_1$-$C_7$ alkyl, $C_1$-$C_7$ haloalkyl, $C_3$-$C_9$ cycloalkyl, $C_3$-$C_9$ halocycloalkyl, $C_1$-$C_7$ alkoxy, $C_1$-$C_7$ haloalkoxy, $C_3$-$C_9$ cycloalkoxy, $C_3$-$C_9$ halocycloalkoxy, $C_2$-$C_8$ alkenyl, $C_2$-$C_8$ haloalkenyl, $C_1$-$C_7$ alkylamino, $C_1$-$C_7$ haloalkylamino, $C_2$-$C_9$ dialkylamino, $C_2$-$C_9$ halodialkylamino, $C_3$-$C_9$ cycloalkylamino or $C_3$-$C_9$ halocycloalkylamino, each substituted or unsubstituted with up to 3 substituents independently selected from $R^8$ or $G^1$; or $R^A$ is $G^1$ or $OG^1$; or $R^A$ is taken together with $R^9$ as $-C(R^J)(R^J)C(=O)-$ (i.e. to form a ring);

$R^B$ is H, $C_1$-$C_4$ alkoxy, $C_1$-$C_4$ haloalkyl or $C_1$-$C_4$ alkyl; or phenyl substituted or unsubstituted with halogen or $C_1$-$C_4$ alkyl;

$R^C$ is H, $C_1$-$C_4$ alkoxy, $C_1$-$C_4$ haloalkyl or $C_1$-$C_4$ alkyl; or phenyl substituted or unsubstituted with halogen or $C_1$-$C_4$ alkyl;

$R^D$ is H, $C_1$-$C_4$ alkyl or $C_2$-$C_4$ alkylcarbonyl;

$R^E$ is H, hydroxy, amino, cyano, formyl, $-C(O)NH_2$, $C_1$-$C_6$ alkyl, $C_1$-$C_6$ haloalkyl, $C_2$-$C_6$ cyanoalkyl, $C_3$-$C_6$ cycloalkyl, $C_4$-$C_8$ cycloalkylalkyl, $C_2$-$C_8$ alkoxyalkyl, $C_3$-$C_8$ alkoxyalkoxyalkyl, $C_2$-$C_8$ haloalkoxyalkyl, $C_2$-$C_8$ alkenyl, $C_2$-$C_8$ haloalkenyl, $C_2$-$C_8$ alkenylalkyl, $C_2$-$C_8$ haloalkenylalkyl, $C_2$-$C_8$ alkylcarbonyl, $C_2$-$C_8$ haloalkylcarbonyl, $C_4$-$C_{10}$ cycloalkylcarbonyl, $C_5$-$C_{10}$ cycloalkylcarbonylalkyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl or $C_2$-$C_8$ dialkylaminosulfonyl; or $G^E$ or $W^EG^E$;

$R^F$ is H, formyl, $-C(O)NH_2$, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $-P(=O)(OH)_2$, $C_1$-$C_6$ dialkylphosphoryl, $C_1$-$C_6$ haloalkylphosphoryl, $C_3$-$C_8$ cycloalkylphosphoryl, $C_2$-$C_8$ dialkoxyphosphoryl, $C_6$-$C_{14}$ dicycloalkoxyphosphoryl, $C_8$-$C_{16}$ dicycloalkylalkoxyphosphoryl, $C_2$-$C_{12}$ bis(alkylamino)phosphoryl, $C_4$-$C_{24}$ bis(dialkylamino)phosphoryl; or $G^F$ or $W^FG^F$;

$R^G$ is formyl, $-C(O)NH_2$, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, —P(=O)(OH)$_2$, $C_1$-$C_6$ dialkylphosphoryl, $C_1$-$C_6$ haloalkylphosphoryl, $C_3$-$C_8$ cycloalkylphosphoryl, $C_2$-$C_8$ dialkoxyphosphoryl, $C_6$-$C_{14}$ dicycloalkoxyphosphoryl, $C_8$-$C_{16}$ dicycloalkylalkoxyphosphoryl, $C_2$-$C_{12}$ bis(alkylamino)phosphoryl, $C_4$-$C_{24}$ bis(dialkylamino)phosphoryl; or phenyl substituted or unsubstituted with $R^{16}$; or $W^G G^G$;

$R^I$ is H, $C_1$-$C_4$ alkoxy, $C_1$-$C_4$ haloalkyl or $C_1$-$C_4$ alkyl; or phenyl substituted or unsubstituted with halogen or $C_1$-$C_4$ alkyl;

$R^J$ is H, $C_1$-$C_4$ alkoxy, $C_1$-$C_4$ haloalkyl or $C_1$-$C_4$ alkyl; or phenyl substituted or unsubstituted with halogen or $C_1$-$C_4$ alkyl;

$Q^1$ is a phenyl ring or a naphthalenyl ring system, each ring or ring system substituted or unsubstituted with up to 5 substituents independently selected from $R^7$; or a 4- to 7-membered heterocyclic ring; or an 8- to 10-membered bicyclic ring system, each ring or ring system containing ring members selected from carbon atoms and 1 to 5 heteroatoms independently selected from up to 2 O, up to 2 S and up to 5 N atoms, wherein up to 3 carbon ring members are independently selected from C(=O) and C(=S), and the sulfur atom ring members are independently selected from S(=O)$_u$(=NR$^{14}$)$_v$, each ring or ring system substituted or unsubstituted with up to 5 substituents independently selected from $R^{10}$ on carbon atom ring members and selected from $R^{12}$ on nitrogen atom ring members; or $Q^2$ is a phenyl ring or a naphthalenyl ring system, each ring or ring system substituted or unsubstituted with up to 5 substituents independently selected from $R^{10}$; or a 4- to 7-membered heterocyclic ring; or an 8- to 10-membered bicyclic ring system, each ring or ring system containing ring members selected from carbon atoms and 1 to 4 heteroatoms independently selected from up to 2 O, up to 2 S and up to 5 N atoms, wherein up to 3 carbon ring members are independently selected from C(=O) and C(=S), and the sulfur atom ring members are independently selected from S(=O)$_u$(=NR$^{14}$)$_v$, each ring or ring system substituted or unsubstituted with up to 5 substituents independently selected from $R^{11}$ on carbon atom ring members and selected from $R^{13}$ on nitrogen atom ring members; or J is —CR$^2$R$^3$—, —CR$^2$R$^3$—CR$^4$R$^5$—, —NR$^6$— or —O—;

$Y^1$ and $Y^2$ are each independently O, S or NR$^{15}$;

$R^1$ is H, hydroxy, amino, cyano, formyl, $C_3$-$C_8$ alkylcarbonylalkyl, —C(C$_1$-$C_4$ alkyl)=N—O(C$_1$-$C_4$ alkyl), —C(O)NH$_2$, $C_1$-$C_6$ alkyl, $C_1$-$C_6$ haloalkyl, $C_2$-$C_6$ alkenyl, $C_3$-$C_6$ alkynyl, $C_2$-$C_6$ cyanoalkyl, $C_3$-$C_6$ cycloalkyl, $C_3$-$C_8$ cycloalkenyl, $C_4$-$C_8$ cycloalkylalkyl, $C_2$-$C_8$ alkoxyalkyl, $C_3$-$C_8$ alkoxyalkoxyalkyl, $C_2$-$C_8$ haloalkoxyalkyl, $C_2$-$C_8$ haloalkenylalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_5$-$C_{10}$ cycloalkylcarbonylalkyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl; or —CPh=N—O(C$_1$-$C_4$ alkyl), each substituted or unsubstituted on ring members with up to 5 substituents independently selected from $R^{13}$; or $G^1$;

$R^2$ and $R^3$ are each independently H, halogen, hydroxy, $C_1$-$C_4$ alkyl, $C_1$-$C_4$ haloalkyl or $C_1$-$C_4$ alkoxy; or $R^2$ and $R^3$ are taken together with the carbon atom to which they are bonded to form a $C_3$-$C_7$ cycloalkyl ring;

$R^4$ and $R^5$ are each independently H, halogen, hydroxy, $C_1$-$C_4$ alkyl, $C_1$-$C_4$ haloalkyl or $C_1$-$C_4$ alkoxy;

$R^6$ is $C_1$-$C_6$ alkyl, $C_2$-$C_6$ alkenyl, $C_3$-$C_6$ alkynyl or $C_1$-$C_6$ alkoxy; or $R^1$ and $R^6$ are taken together as $C_3$-$C_6$ alkylene or —CH$_2$OCH$_2$—;

$R^7$ is H, halogen, hydroxy, $C_1$-$C_4$ alkoxy, $C_1$-$C_4$ haloalkyl or $C_1$-$C_4$ alkyl;

each $R^8$ is independently cyano, hydroxy, amino, nitro, —CHO, —C(=O)OH, —C(=O)NH$_2$, —SO$_2$NH$_2$, $C_2$-$C_6$ alkenyl, $C_2$-$C_6$ alkynyl, $C_2$-$C_8$ alkylcarbonyl, $C_2$-$C_8$ haloalkylcarbonyl, $C_2$-$C_8$ alkoxycarbonyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_1$-$C_6$ alkoxy, $C_1$-$C_6$ haloalkoxy, $C_2$-$C_8$ alkylcarbonyloxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylaminosulfonyl, $C_2$-$C_8$ dialkylaminosulfonyl, $C_3$-$C_{10}$ trialkylsilyl, $C_1$-$C_6$ alkylamino, $C_2$-$C_8$ dialkylamino, $C_2$-$C_8$ alkylcarbonylamino or $C_1$-$C_6$ alkylsulfonylamino;

$R^9$ is H, hydroxy, amino, $C_1$-$C_6$ alkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl or $C_3$-$C_{10}$ trialkylsilyl or $G^1$;

each $R^{10}$ and $R^{11}$ is independently halogen, hydroxy, cyano, nitro, amino, $C_1$-$C_8$ alkyl, $C_1$-$C_8$ cyanoalkyl, $C_1$-$C_8$ cyanoalkoxy, $C_1$-$C_8$ haloalkyl, $C_1$-$C_8$ hydroxyalkyl, $C_1$-$C_8$ nitroalkyl, $C_2$-$C_8$ alkenyl, $C_2$-$C_8$ haloalkenyl, $C_2$-$C_8$ nitroalkenyl, $C_2$-$C_8$ alkynyl, $C_2$-$C_8$ haloalkynyl, $C_2$-$C_8$ alkoxyalkyl, $C_3$-$C_8$ alkoxyalkoxyalkyl, $C_2$-$C_8$ haloalkoxyalkyl, $C_2$-$C_8$ haloalkoxyhaloalkoxy, $C_3$-$C_6$ cycloalkyl, cyclopropylmethyl, 1-methylcyclopropyl, 2-methylcyclopropyl, $C_4$-$C_{10}$ cycloalkylalkyl, $C_4$-$C_{10}$ halocycloalkylalkyl, $C_5$-$C_{12}$ alkylcycloalkylalkyl, $C_5$-$C_{12}$ cycloalkylalkenyl, $C_5$-$C_{12}$ cycloalkylalkynyl, $C_3$-$C_8$ cycloalkyl, $C_3$-$C_8$ halocycloalkyl, $C_4$-$C_{10}$ alkylcycloalkyl, $C_6$-$C_{12}$ cycloalkylcycloalkyl, $C_3$-$C_8$ cycloalkenyl, $C_3$-$C_8$ halocycloalkenyl, $C_2$-$C_8$ haloalkoxyalkoxy, $C_2$-$C_8$ alkoxyalkoxy, $C_4$-$C_{10}$ cycloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylamino, $C_2$-$C_8$ dialkylamino, $C_2$-$C_8$ halodialkylamino, $C_2$-$C_8$ alkylaminoalkyl, $C_2$-$C_8$ haloalkylaminoalkyl, $C_4$-$C_{10}$ cycloalkylaminoalkyl, $C_3$-$C_{10}$ dialkylaminoalkyl, —CHO, $C_2$-$C_8$ alkylcarbonyl, $C_2$-$C_8$ haloalkylcarbonyl, $C_4$-$C_{10}$ cycloalkylcarbonyl, —C(=O)OH, $C_2$-$C_8$ alkoxycarbonyl, $C_2$-$C_8$ haloalkoxycarbonyl, $C_4$-$C_{10}$ cycloalkoxycarbonyl, $C_5$-$C_{12}$ cycloalkylalkoxycarbonyl, —C(=O)NH$_2$, $C_2$-$C_8$ alkylaminocarbonyl, $C_4$-$C_{10}$ cycloalkylaminocarbonyl, $C_3$-$C_{10}$ dialkylaminocarbonyl, $C_1$-$C_8$ alkoxy, $C_1$-$C_8$ haloalkoxy, $C_2$-$C_8$ alkenyloxy, $C_2$-$C_8$ haloalkenyloxy, $C_3$-$C_8$ alkynyloxy, $C_3$-$C_8$ haloalkynyloxy, $C_3$-$C_8$ cycloalkoxy, $C_3$-$C_8$ halocycloalkoxy, $C_4$-$C_{10}$ cycloalkylalkoxy, $C_3$-$C_{10}$ alkylcarbonylalkoxy, $C_2$-$C_8$ alkylcarbonyloxy, $C_2$-$C_8$ haloalkylcarbonyloxy, $C_4$-$C_{10}$ cycloalkylcarbonyloxy, $C_1$-$C_8$ alkylsulfonyloxy, $C_1$-$C_8$ haloalkylsulfonyloxy, $C_1$-$C_8$ alkylthio, $C_1$-$C_8$ haloalkylthio, $C_3$-$C_8$ cycloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, $C_3$-$C_8$ cycloalkylsulfonyl, formylamino, $C_2$-$C_8$ alkylcarbonylamino, $C_2$-$C_8$ haloalkylcarbonylamino, $C_3$-$C_8$ cycloalkylamino, $C_2$-$C_8$ alkoxycarbonylamino, $C_1$-$C_6$ alkylsulfonylamino, $C_1$-$C_6$ haloalkylsulfonylamino, —SF$_5$, —SCN, SO$_2$NH$_2$, $C_3$-$C_{12}$ trialkylsilyl, $C_4$-$C_{12}$ trialkylsilylalkyl or $C_4$-$C_{12}$ trialkylsilylalkoxy; or G$^2$; or R$^{20}$S(=O)=N—, R$^{20}$S(=O)$_2$NR$^{19}$—C(=O)— or R$^{20}$(R$^{19}$N=)$_q$S(=O)$_p$—, wherein the free bond projecting to the right indicates the connecting point to Q$^1$; or each R$^{12}$ and R$^{13}$ is independently cyano, $C_1$-$C_3$ alkyl, $C_1$-$C_8$ hydroxyalkyl, $C_2$-$C_3$ alkenyl, $C_2$-$C_3$ alkynyl, $C_3$-$C_6$ cycloalkyl, $C_2$-$C_3$ alkoxyalkyl, $C_1$-$C_3$ alkoxy, $C_2$-$C_3$ alkylcarbonyl, $C_2$-$C_3$ alkoxycarbonyl, $C_2$-$C_3$ alkylaminoalkyl or $C_3$-$C_4$ dialkylaminoalkyl;

each R$^{14}$ is independently H, cyano, $C_2$-$C_3$ alkylcarbonyl or $C_2$-$C_3$ haloalkylcarbonyl;

each R$^{15}$ is independently H, cyano, hydroxy, CHO, $C_1$-$C_4$ alkyl, $C_1$-$C_4$ haloalkyl, $C_1$-$C_4$ alkoxy, $C_2$-$C_6$ alkylcarbonyl, $C_2$-$C_6$ haloalkylcarbonyl, —(C=O)CH$_3$ or —(C=O)CF$_3$;

each G$^1$ is independently phenyl; or a 5- or 6-membered heterocyclic ring, each substituted or unsubstituted on ring members with up to 5 substituents independently selected from R$^{17}$;

each W$^E$, W$^F$ and W$^G$ is independently —C(=O)—, —C(=O)O—, —C(=O)NH— or —S(=O)$_2$—;

each G$^E$, G$^F$ and G$^G$ is independently phenyl substituted or unsubstituted with R$^{16}$; or a 5- or 6-membered heterocyclic ring, each heterocyclic ring substituted or unsubstituted on ring members with up to 5 substituents independently selected from R$^{16}$;

each G$^2$ is independently phenyl, phenylmethyl (i.e. benzyl), pyridinylmethyl, phenylcarbonyl (i.e. benzoyl), phenoxy, phenylethynyl, phenylsulfonyl or a 5- or 6-membered heterocyclic ring, each substituted or unsubstituted on ring members with up to 5 substituents independently selected from R$^{18}$;

each R$^{16}$, R$^{17}$ and R$^{18}$ is independently halogen, cyano, hydroxy, amino, nitro, —CHO, —C(=O)OH, —C(=O)NH$_2$, —SO$_2$NH$_2$, $C_1$-$C_6$ alkyl, $C_1$-$C_6$ haloalkyl, $C_2$-$C_6$ alkenyl, $C_2$-$C_6$ alkynyl, $C_2$-$C_8$ alkylcarbonyl, $C_2$-$C_8$ haloalkylcarbonyl, $C_2$-$C_8$ alkoxycarbonyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_1$-$C_6$ alkoxy, $C_1$-$C_6$ haloalkoxy, $C_2$-$C_8$ alkylcarbonyloxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylaminosulfonyl, $C_2$-$C_8$ dialkylaminosulfonyl, $C_3$-$C_{10}$ trialkylsilyl, $C_1$-$C_6$ alkylamino, $C_2$-$C_8$ dialkylamino, $C_2$-$C_8$ alkylcarbonylamino, $C_1$-$C_6$ alkylsulfonylamino, phenyl, pyridinyl or thienyl;

each R$^{19}$ is independently H, cyano, $C_2$-$C_3$ alkylcarbonyl or $C_2$-$C_3$ haloalkylcarbonyl;

each R$^{20}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_1$-$C_6$ alkoxy or $C_3$-$C_{10}$ trialkylsilyl; or G$^1$;

each u and v are independently 0, 1 or 2 in each instance of S(=O)$_u$(=NR$^{14}$)$_v$, provided that the sum of u and v is 0, 1 or 2; and each p and q are independently 0, 1 or 2 in each instance of R$^{20}$(R$^{19}$N=)$_q$S(=O)$_p$—, provided that the sum of u and v is 0, 1 or 2 and when p is 0, q is other than 1 or 2.

More particularly, this invention pertains to a compound of Formula 1 (including all stereoisomers), an N-oxide or a salt thereof. This invention also relates to a herbicidal composition comprising a compound of the invention (i.e. in a herbicidally effective amount) and at least one component selected from the group consisting of surfactants, solid diluents and liquid diluents. This invention further relates to a method for controlling the growth of undesired vegetation comprising contacting the vegetation or its environment with a herbicidally effective amount of a compound of the invention (e.g., as a composition described herein).

This invention also includes a herbicidal mixture comprising (a) a compound selected from Formula 1, N-oxides, and salts thereof, and (b) at least one additional active ingredient selected from (b1) through (b16); and salts of compounds of (b1) through (b16), as described below.

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated)

the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to herein, the term "seedling", used either alone or in a combination of words means a young plant developing from the embryo of a seed.

As referred to herein, the term "broadleaf" used either alone or in words such as "broadleaf weed" means dicot or dicotyledon, a term used to describe a group of angiosperms characterized by embryos having two cotyledons.

As used herein, the term "alkylating agent" refers to a chemical compound in which a carbon-containing radical is bound through a carbon atom to a leaving group such as halide or sulfonate, which is displaceable by bonding of a nucleophile to said carbon atom. Unless otherwise indicated, the term "alkylating" does not limit the carbon-containing radical to alkyl.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkylene" denotes a straight-chain or branched alkanediyl. Examples of "alkylene" include $CH_2CH_2CH_2$, $CH_2CH(CH_3)$ and the different butylene, pentylene and hexylene isomers.

"Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkoxyalkoxyalkyl" denotes at least alkoxy substitution on the alkoxy moiety of alkoxyalkyl moiety. Examples of "alkoxyalkoxyalkyl" include $CH_3OCH_2OCH_2$—, $CH_3CH_2O(CH_3)CHOCH_2$— and $(CH_3O)_2CHOCH_2$—. "Alkoxyalkoxy" denotes alkoxy substitution on alkoxy. Examples of alkoxyalkoxy include $CH_3CH_2OCH_2O$, $(CH_3)_2CHOCH_2CH_2O$ and $CH_3CH_2CH_2OCH_2O$. "Alkenyloxy" includes straight-chain or branched alkenyloxy moieties. Examples of "alkenyloxy" include $H_2C=CHCH_2O$, $(CH_3)_2C=CHCH_2O$, $(CH_3)CH=CHCH_2O$, $(CH_3)CH=C(CH_3)CH_2O$ and $CH_2=CHCH_2CH_2O$. "Alkynyloxy" includes straight-chain or branched alkynyloxy moieties. Examples of "alkynyloxy" include $HC\equiv CCH_2O$, $CH_3C\equiv CCH_2O$ and $CH_3C\equiv CCH_2CH_2O$. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(O)$—, $CH_3CH_2S(O)$—, $CH_3CH_2CH_2S(O)$—, $(CH_3)_2CHS(O)$— and the different butylsulfinyl, pentylsulfinyl and hexylsulfinyl isomers. "Alkylsulfonyl" indicates a sulfonyl moiety substituted with a straight-chain or branched alkyl group. Examples of "alkylsulfonyl" include $CH_3S(O)_2$—, $CH_3CH_2S(O)_2$—, $CH_3CH_2CH_2S(O)_2$—, $(CH_3)_2CHS(O)_2$—, and the different butylsulfonyl, pentylsulfonyl and hexylsulfonyl isomers. "Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2CH_2SCH_2$ and $CH_3CH_2SCH_2CH_2$. "Alkylsulfinylalkyl" denotes alkylsulfinyl substitution on alkyl. Examples of "alkylsulfinylalkyl" include $CH_3S(=O)CH_2$, $CH_3S(=O)CH_2CH_2$, $CH_3CH_2S(=O)CH_2$ and $CH_3CH_2S(=O)CH_2CH_2$. "Alkylsulfonylalkyl" denotes alkylsulfonyl substitution on alkyl. Examples of "alkylsulfonylalkyl" include $CH_3S(=O)_2CH_2$, $CH_3S(=O)_2CH_2CH_2$, $CH_3CH_2S(=O)_2CH_2$ and $CH_3CH_2S(=O)_2CH_2CH_2$. Examples of "alkylsulfonyloxy" include $CH_3S(O)_2O$—, $CH_3CH_2S(O)_2O$— and $CH_3CH_2CH_2S(O)_2O$—. "Alkylamino", "dialkylamino", "halodialkylamino" and the like, are defined analogously to the above examples. Examples of "alkylsulfonylamino" include $CH_3S(=O)NH$— and $CH_2CH_2CH_2S(=O)NH$—. Examples of "alkylaminoalkyl" include $CH_3NHCH_2$—, $(CH_3)_2CHNHCH_2$— and $CH_3NHCH(CH_3)$—. Examples of "dialkylaminoalkyl" include $(CH_3)_2NCH_2$—, $(CH_3)_2NC(CH_3)H$— and $(CH_3)(CH_3)NCH_2$—. Examples of "alkylaminocarbonyl" include $(CH_3)NHC(O)$— and $(CH_3CH_2)NHC(O)$—. An example of "dialkylaminocarbonyl" is $(CH_3)_2NC(O)$—. An example of "alkylaminosulfonyl" is $(CH_3)NHS(O)_2$— and an example of "dialkylaminosulfonyl" is $(CH_3)_2NS(O)_2$—. The term "alkylcarbonylamino" denotes a straight-chain or branched alkyl moiety bonded to the $C(=O)$ moiety of carbonylamino group. Examples of "alkylcarbonylamino" include $CH_3C(=O)NH$— and $CH_3CH_2C(=O)NH$—. The term "alkoxycarbonylamino" denotes a straight-chain or branched alkoxy moiety bonded to the $C(=O)$ moiety of carbonylamino group. Examples of "alkoxycarbonylamino" include $CH_3OC(=O)NH$— and $CH_3CH_2OC(=O)NH$—.

"Cycloalkyl" includes, for example, cyclopropyl, cyclobutyl, cyclopentyl and cyclohexyl. The term "alkylcycloalkyl" denotes alkyl substitution on a cycloalkyl moiety and includes, for example, ethylcyclopropyl, i-propylcyclobutyl, 3-methylcyclopentyl and 4-methylcyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups. Examples of the term "alkylcycloalkylalkyl" include 1-methylcyclopropylmethyl and 2-methylcyclopentylethyl. The term "cycloalkylalkenyl" denotes cycloalkyl bonded to an alkenyl moiety. The term "cycloalkylcycloalkyl" denotes cycloalkyl substitution on a cycloalkyl moiety by a single bond. The term "cycloalkylalkynyl" denotes cycloalkyl bonded to an alkynyl moiety. The term "cycloalkylamino" denotes cycloalkyl bonded to an amino moiety. The term "cycloalkylaminocarbonyl" denotes cycloalkyl bonded to an aminocarbonyl moiety. The term "cycloalkylaminoalkyl" denotes cycloalkyl bonded to an aminoalkyl moiety. The term "cycloalkylcarbonyl" denotes cycloalkyl bonded to a carbonyl moiety. The term "cycloalkylcarbonylalkyl" denotes cycloalkyl bonded to a carbonylalkyl moiety. The term "cycloalkylcarbonyloxy" denotes cycloalkyl bonded to the carbon atom of a carbonyloxy moiety. The term "cycloalkoxy" denotes cycloalkyl linked through an oxygen atom such as cyclopentyloxy and cyclohexyloxy. The term "cycloalkoxyalkyl" denotes cycloalkoxy linked through an alkyl moiety. The terms "cycloalkylthio", "cycloalkylsulfinyl" and "cycloalkylsulfonyl" denotes cycloalkyl bonded through a sulfur, sulfinyl or sulfonyl moiety, respectively.

The term "cycloalkoxycarbonyl" denotes cycloalkoxy linked through a carbonyl moiety. "Cycloalkylalkoxy" denotes cycloalkylalkyl linked through an oxygen atom attached to the alkyl chain. Examples of "cycloalkylalkoxy" include cyclopropylmethoxy, cyclopentylethoxy, and other cycloalkyl moieties bonded to straight-chain or branched alkoxy groups. "Cycloalkenyl" includes groups such as cyclopentenyl and cyclohexenyl as well as groups with more than one double bond such as 1,3- and 1,4-cyclohexadienyl. The term "halocycloalkenyl" denotes halogen substitution on the cycloalkenyl moiety.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C$, $ClCH_2$, $CF_3CH_2$ and $CF_3CCl_2$. The terms "halocycloalkyl", "halocycloalkylalkyl", "halocycloalkoxy", "haloalkoxy", "haloalkoxyalkoxy", "haloalkylthio", "haloalkylsulfinyl", "haloalkylsulfonyl", "haloalkenyl", "haloalkynyl", "haloalkenyloxy", "haloalkenylalkyl", "haloalkylcarbonyl", "haloalkylcarbonylamino", "haloalkylsulfonylamino", "haloalkoxyhaloalkoxy", "haloalkylsulfonyloxy", "haloalkynyloxy", "haloalkoxyalkyl", "haloalkylcarbonyloxy", "haloalkylaminoalkyl" and the like, are defined analogously to the term "haloalkyl". Examples of "haloalkoxy" include $CF_3O—$, $CCl_3CH_2O—$, $HCF_2CH_2CH_2O—$ and $CF_3CH_2O—$. Examples of "haloalkylthio" include $CCl_3S—$, $CF_3S—$, $CCl_3CH_2S—$ and $ClCH_2CH_2CH_2S—$. Examples of "haloalkylsulfinyl" include $CF_3S(O)—$, $CCl_3S(O)—$, $CF_3CH_2S(O)—$ and $CF_3CF_2S(O)—$. Examples of "haloalkylsulfonyl" include $CF_3S(O)_2—$, $CCl_3S(O)_2—$, $CF_3CH_2S(O)_2—$ and $CF_3CF_2S(O)_2—$. Examples of "haloalkylsulfonyloxy" include $CHCl_2S(O)_2O—$, $CH_2ClCH_2S(O)_2O—$ and $CH_3CHClCH_2S(O)_2O—$. Examples of "haloalkenyl" include $(Cl)_2C=CHCH_2—$ and $CF_3CH_2CH=CHCH_2—$. Examples of "haloalkenyloxy" include $(Cl)_2C=CHCH_2O—$ and $CF_3CH_2CH=CHCH_2O—$. Examples of "haloalkynyl" include $HC≡CCHCl—$, $CF_3C≡C—$, $CCl_3C≡C—$ and $FCH_2C≡CCH_2—$. Examples of "haloalkynyloxy" include $HC≡CCHClO—$, $CCl_3C≡C—$ and $FCH_2C≡CCH_2O—$. Examples of "haloalkoxyalkyl" include $CF_3OCH_2—$, $ClCH_2CH_2OCH_2CH_2—$, $Cl_3CCH_2OCH_2—$ as well as branched alkyl derivatives. Examples of "haloalkoxycarbonyl" include $CF_3OC(O)—$, $ClCH_2CH_2OCH_2CH_2—$, $Cl_3CCH_2OCH_2OC(O)—$ as well as branched alkyl derivatives.

"Alkylcarbonyl" denotes a straight-chain or branched alkyl moiety bonded to a $C(=O)$ moiety. "Alkoxycarbonyl" denotes a straight-chain or branched alkoxy moiety bonded to a $C(=O)$ moiety. Examples of "alkylcarbonyl" include $CH_3C(=O)—$, $CH_3CH_2CH_2C(=O)—$ and $(CH_3)_2CHC(=O)—$. Examples of "alkoxycarbonyl" include $CH_3OC(=O)—$, $CH_3CH_2OC(=O)—$, $CH_3CH_2CH_2OC(=O)—$, $(CH_3)_2CHOC(=O)—$ and the different butoxy- or pentoxy-carbonyl isomers. "Cycloalkylalkoxycarbonyl" denotes a cycloalkylalkyl moieties bonded to an oxygen atom of alkoxycarbonyl moiety. Examples of "cycloalkylalkoxycarbonyl" include cyclopropyl-$CH_2OC(=O)—$, cyclopropyl-$CH(CH_3)OC(=O)—$ and cyclopentyl-$CH_2OC(=O)—$. "Alkylcarbonylalkyl" denotes a straight-chain or branched chain alkyl group bonded to the carbon atom of to a carbonylalkyl moiety. Examples of "alkylcarbonylalkyl" include $(CH_3)C(=O)CH_2—$ and $(CH_3CH_2)C(=O)CH_2—$. "Alkylcarbonyloxy" denotes a straight-chain or branched-chain alkyl group bonded to the carbon atom of to a carbonyloxy moiety. Examples of "alkylcarbonyloxy" include $(CH_3)C(=O)O—$ and $(CH_3CH_2)C(=O)O—$.

The term "dialkylphosphoryl" refers to a phosine oxide derivative. Examples of "dialkylphosphoryl" include $—P(=O)(CH_3)_2$ and $—P(=O)(CH_2CH_3)_2$. The term "haloalkylphosphoryl" refers to a halogenated phosphine oxide derivative. Examples of "haloalkylphosphory" include $P(=O)(CH_2Cl)_2$ and $—P(=O)(CH_2CH_2Br)_2$ and $—P(=O)(CH_2CH_2CH_2CF_2)_2$. The term "cycloalkylphosphoryl" refers to a cycloalkyl phosphine oxide derivative. Examples of "cycloalkylphosphoryl" include $—P(=O)(c-Pr)_2$ and $—P(=O)(c-hex)_2$. The term "dialkoxyphosphoryl" refers to a phosphonic acid derivative. Examples of "dialkoxyphosphoryl" include $—P(=O)(OCH_3)_2$ and $—P(=O)(OCH_2CH_3)_2$. The term "dicycloalkylalkoxyphosphoryl" refers to a phosphonic acid derivative. Examples of "dicycloalkylalkoxyphophoryl" include $—P(=O)(O-c-Pr)_2$ and $—P(=O)(O-c-Bu)_2$. Examples of bis(alkylamino)phosphoryl include $—P(=O)(NHCH_3)_2$ and $—P(=O)(NHCH_2CH_3)_2$. Examples of bis(dialkylamino)phosphoryl include $—P(=O)(N(CH_3)_2)_2$, and $—P(=O)(N(CH_2CH_3)_2)_2$.

The term "cyanoalkyl" or "cyanoalkoxy" means a cyano group bonded through an alkyl or alkoxy moiety, respectively. The carbon in the cyano group is not included in the total number of carbon atoms for this term. The term "nitroalkyl" or "nitroalkenyl" represents a nitro group bonded through an alkyl or alkenyl moiety, respectively. The term "hydroxyalkyl" means a hydroxyl group bonded through an alkyl moiety. The term "trialkylsilyl" means three alkyl groups bonded through silicon. The term "trialkylsilylalkyl" means three alkyl groups bonded through a silylalkyl moiety. The term "trialkylsilylalkoxy" means three alkyl groups bonded through a silylalkoxy moiety.

The total number of carbon atoms in a substituent group is indicated by the "$C_i$-$C_j$" prefix where i and j are numbers from 1 to 24. For example, $C_1$-$C_4$ alkylsulfonyl designates methylsulfonyl through butylsulfonyl; $C_2$ alkoxyalkyl designates $CH_3OCH_2—$; $C_3$ alkoxyalkyl designates, for example, $CH_3CH(OCH_3)—$, $CH_3OCH_2CH_2—$ or $CH_3CH_2OCH_2—$; and $C_4$ alkoxyalkyl designates the various isomers of an alkyl group substituted with an alkoxy group containing a total of four carbon atoms, examples including $CH_3CH_2CH_2OCH_2—$ and $CH_3CH_2OCH_2CH_2—$.

When a compound is substituted with a substituent bearing a subscript that indicates the number of said substituents can exceed 1, said substituents (when they exceed 1) are independently selected from the group of defined substituents, e.g., $(R^7)_n$, n is 1, 2, 3, 4 or 5). When a group contains a substituent which can be hydrogen, for example $R^2$ or $R^3$ then when this substituent is taken as hydrogen, it is recognized that this is equivalent to said group being unsubstituted. When a variable group is shown to be optionally attached to a position, for example $(R^7)_n$ wherein n may be 0, then hydrogen may be at the position even if not recited in the variable group definition. When one or more positions on a group are said to be "not substituted" or "unsubstituted", then hydrogen atoms are attached to take up any free valency.

The expression "fully saturated" in relation to a ring of atoms means that the bonds between the atoms of the ring are all single. The expression "fully unsaturated" in relation to a ring means that the bonds between the atoms in the ring are single or double bonds according to valence bond theory and furthermore the bonds between the atoms in the ring include as many double bonds as possible without double bonds being cumulative (i.e. no C=C=C, N=C=C, etc.). The term "partially unsaturated" in relation to a ring denotes a ring comprising at least one ring member bonded to an adjacent ring member though a double bond and which conceptually potentially accommodates a number of non-cumulated double bonds through adjacent ring members (i.e. in its fully unsaturated counterpart form) greater than the number of double bonds present (i.e. in its partially unsaturated form). When a fully unsaturated ring satisfies Hückel's rule then it can also be described as aromatic.

Unless otherwise indicated, a "ring" or "ring system" as a component of Formula 1 (e.g., substituent $Q^1$) is carbocyclic or heterocyclic. The term "ring system" denotes two or more fused rings. The terms "bicyclic ring system" and "fused bicyclic ring system" denote a ring system consisting of two fused rings, in which either ring can be saturated, partially unsaturated, or fully unsaturated unless otherwise indicated. The term "fused heterobicyclic ring system" denotes a fused bicyclic ring system in which at least one ring atom is not carbon.

The term "ring member" refers to an atom or other moiety (e.g., C(=O), C(=S), S(=O) or S(=O)$_2$) forming the backbone of a ring or ring system.

The terms "carbocyclic ring", "carbocycle" or "carbocyclic ring system" denote a ring or ring system wherein the atoms forming the ring backbone are selected only from carbon. Unless otherwise indicated, a carbocyclic ring can be a saturated, partially unsaturated, or fully unsaturated ring. When a fully unsaturated carbocyclic ring satisfies Hückel's rule, then said ring is also called an "aromatic ring". "Saturated carbocyclic" refers to a ring having a backbone consisting of carbon atoms linked to one another by single bonds; unless otherwise specified, the remaining carbon valences are occupied by hydrogen atoms.

The terms "heterocyclic ring", "heterocycle" or "heterocyclic ring system" denote a ring or ring system in which at least one atom forming the ring backbone is not carbon, e.g., nitrogen, oxygen or sulfur. Typically a heterocyclic ring contains no more than 5 nitrogens, no more than 2 oxygens and no more than 2 sulfurs. Unless otherwise indicated, a heterocyclic ring can be a saturated, partially unsaturated, or fully unsaturated ring. When a fully unsaturated heterocyclic ring satisfies Hückel's rule, then said ring is also called a "heteroaromatic ring" or "aromatic heterocyclic ring". Unless otherwise indicated, heterocyclic rings and ring systems can be attached through any available carbon or nitrogen by replacement of a hydrogen on said carbon or nitrogen.

"Aromatic" indicates that each of the ring atoms is essentially in the same plane and has a p-orbital perpendicular to the ring plane, and that (4n+2) π electrons, where n is a positive integer, are associated with the ring to comply with Hückel's rule. The term "aromatic ring or ring system" denotes a carbocyclic or heterocyclic ring or ring system in which the ring or at least one ring of the ring system is aromatic. The term "aromatic ring or ring system" is also referred to as "aryl". The term "aromatic heterocyclic ring system" denotes a heterocyclic ring system in which at least one ring of the ring system is aromatic. The term "nonaromatic ring system" denotes a carbocyclic or heterocyclic ring system that may be fully saturated, as well as partially or fully unsaturated, provided that none of the rings in the ring system are aromatic. The term "nonaromatic carbocyclic ring system" describes a carbocyclic ring system in which no ring in the ring system is aromatic. The term "nonaromatic heterocyclic ring system" denotes a heterocyclic ring system in which no ring in the ring system is aromatic.

The term "substituted or unsubstituted" or "optionally substituted" in connection with the heterocyclic rings refers to groups which are unsubstituted or have at least one non-hydrogen substituent that does not extinguish the biological activity possessed by the unsubstituted analog. As used herein, the following definitions shall apply unless otherwise indicated. The term "substituted or unsubstituted" is used interchangeably with the phrase "optionally substituted" or with the term "(un)substituted." Unless otherwise indicated, an optionally substituted group may have a substituent at each substitutable position of the group, and each substitution is independent of the other.

When $Q^1$ or $Q^2$ is 4- to 7-membered heterocyclic ring system, it may be attached to the remainder of Formula 1 though any available carbon or nitrogen ring atom, unless otherwise described. As noted above, $Q^1$ and $Q^2$ can be (among others) phenyl optionally substituted with one or more substituents selected from a group of substituents as defined in the Summary of the Invention. An example of phenyl optionally substituted with one to five substituents is the ring illustrated as U-1 in Exhibit 1, wherein, for example, $R^v$ is $R^{10}$ as defined in the Summary of the Invention for $Q^1$, or $R^v$ is $R^{11}$ as defined in the Summary of the Invention for $Q^2$, and r is an integer (from 0 to 5).

As noted above, $Q^1$ and $Q^2$ can be (among others) a 5- or 6-membered unsaturated heterocyclic ring, substituted or unsubstituted with one or more substituents selected from a group of substituents as defined in the Summary of the Invention. Examples of a 5- or 6-membered unsaturated aromatic heterocyclic ring substituted or unsubstituted with from one or more substituents include the rings U-2 through U-61 illustrated in Exhibit 1 wherein $R^v$ is any substituent as defined in the Summary of the Invention for $Q^1$ and $Q^2$, and r is an integer from 0 to 4, limited by the number of available positions on each U group. As U-29, U-30, U-36, U-37, U-38, U-39, U-40, U-41, U-42 and U-43 have only one available position, for these U groups r is limited to the integers 0 or 1, and r being 0 means that the U group is unsubstituted and a hydrogen is present at the position indicated by $(R^v)_r$.

Exhibit 1

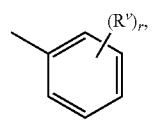

U-1

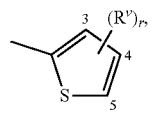

U-2

-continued
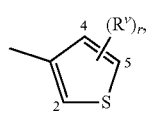 U-3
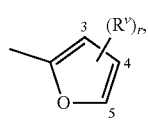 U-4
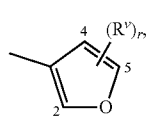 U-5
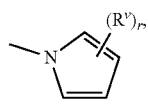 U-6
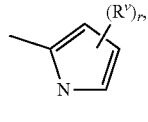 U-7
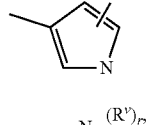 U-8
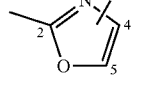 U-9
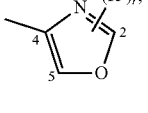 U-10
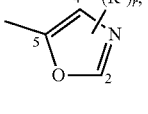 U-11
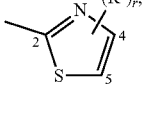 U-12
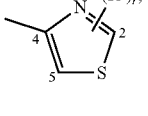 U-13
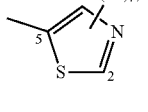 U-14
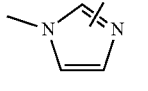 U-15
-continued
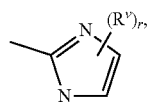 U-16
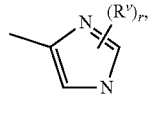 U-17
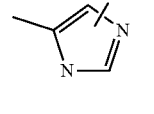 U-18
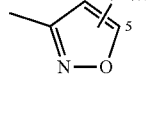 U-19
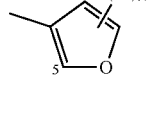 U-20
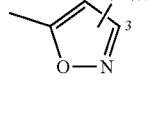 U-21
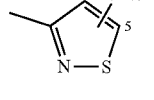 U-22
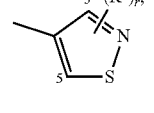 U-23
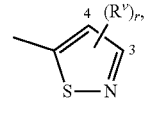 U-24
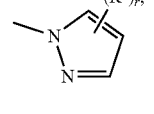 U-25
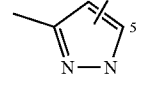 U-26
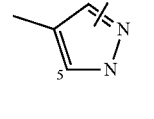 U-27
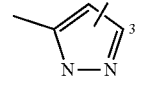 U-28

-continued
U-29 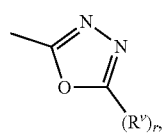
U-30 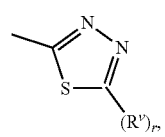
U-31 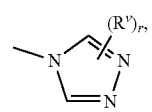
U-32 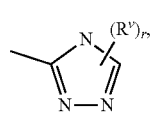
U-33 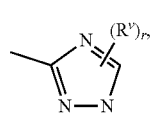
U-34 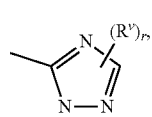
U-35 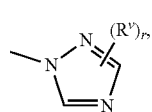
U-36 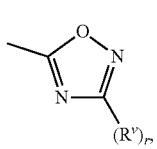
U-37 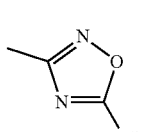
U-38 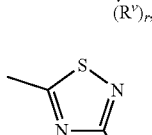
U-39 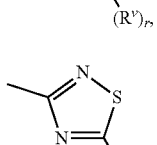
U-40 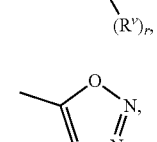
-continued
U-41 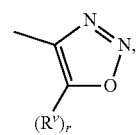
U-42 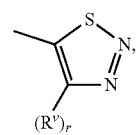
U-43 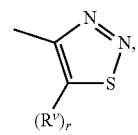
U-44 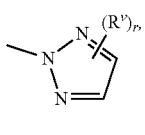
U-45 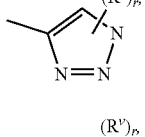
U-46 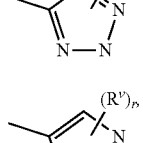
U-47 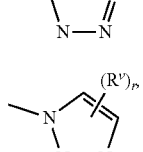
U-48 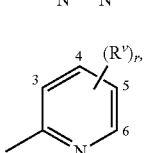
U-49 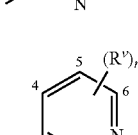
U-50 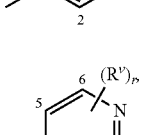
U-51 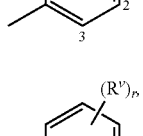
U-52

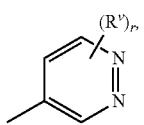 U-53

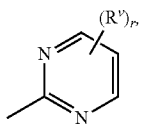 U-54

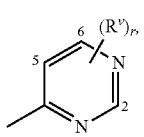 U-55

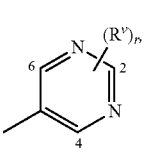 U-56

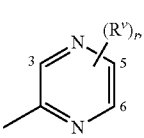 U-57

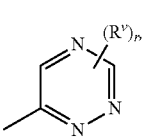 U-58

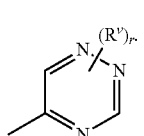 U-59

U-60

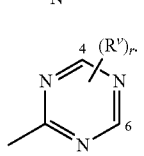 and U-61

Note that when $Q^1$ or $Q^2$ is a 5- or 6-membered saturated or unsaturated non-aromatic heterocyclic ring optionally substituted with one or more substituents selected from the group of substituents as defined in the Summary of the Invention for $Q^1$ or $Q^2$, one or two carbon ring members of the heterocycle can optionally be in the oxidized form of a carbonyl moiety.

Examples of a 5- or 6-membered saturated or non-aromatic unsaturated heterocyclic ring containing ring members selected from up to two O atoms and up to two S atoms, and optionally substituted on carbon atom ring members with up to five substituents as defined in the Summary of the Invention includes the rings G-1 through G-35 as illustrated in Exhibit 2. Note that when the attachment point on the G group is illustrated as floating, the G group can be attached to the remainder of Formula 1 through any available carbon or nitrogen of the G group by replacement of a hydrogen atom. The optional substituents corresponding to $R^v$ can be attached to any available carbon or nitrogen by replacing a hydrogen atom. For these G rings, r is typically an integer from 0 to 4, limited by the number of available positions on each G group.

Note that when $Q^1$ or $Q^2$ comprises a ring selected from G-28 through G-35, $G^2$ is selected from O, S or N. Note that when $G^2$ is N, the nitrogen atom can complete its valence by substitution with either H or the substituents corresponding to $R^v$ as defined in the Summary of the Invention for $Q^1$ or $Q^2$ (i.e. $R^{10}$ or $R^{11}$ on carbon atoms and $R^{12}$ or $R^{13}$ on nitrogen atoms).

Exhibit 2

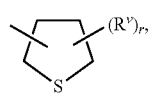 G-1

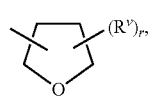 G-2

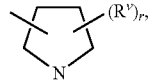 G-3

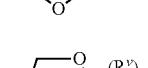 G-4

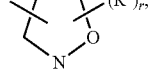 G-5

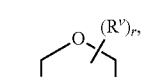 G-6

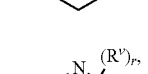 G-7

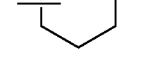 G-8

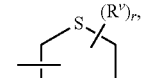 G-9

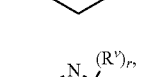 G-10

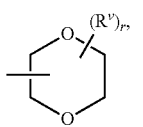 G-11

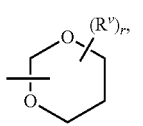 G-12

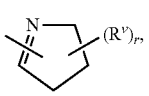 G-13

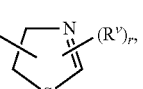 G-14

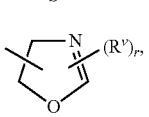 G-15

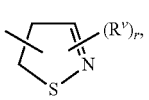 G-16

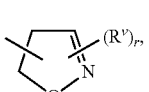 G-17

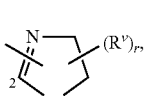 G-18

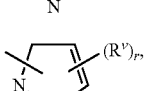 G-19

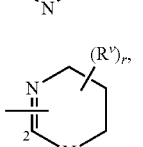 G-20

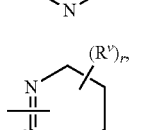 G-21

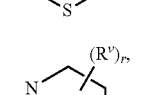 G-22

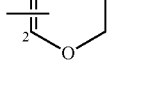 G-23

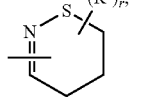 G-24

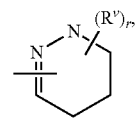 G-25

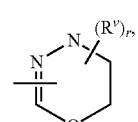 G-26

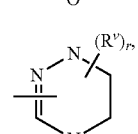 G-27

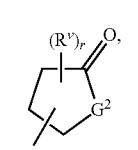 G-28

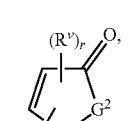 G-29

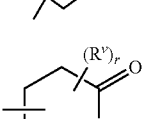 G-30

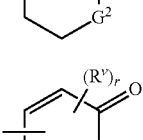 G-31

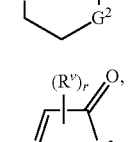 G-32

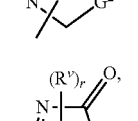 G-33

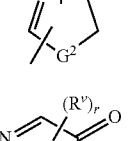 G-34 and

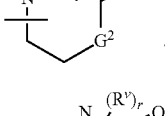 G-35

As noted above, $Q^1$ or $Q^2$ can be (among others) an 8-, 9- or 10-membered fused bicyclic ring system optionally substituted with one or more substituents selected from a group of substituents as defined in the Summary of the Invention (i.e. $R^{10}$ or $R^{11}$ on carbon atoms and $R^{12}$ or $R^{13}$ on nitrogen atoms). Examples of 8-, 9- or 10-membered fused bicyclic ring system optionally substituted with from one or more substituents include the rings U-81 through U-123 illustrated in Exhibit 3 wherein $R^v$ is any substituent as defined in the Summary of the Invention for $Q^1$ or $Q^2$ (i.e. $R^{10}$ or $R^{11}$ on carbon atoms and $R^{12}$ or $R^{13}$ on nitrogen atoms), and r is typically an integer from 0 to 5.
Exhibit 3
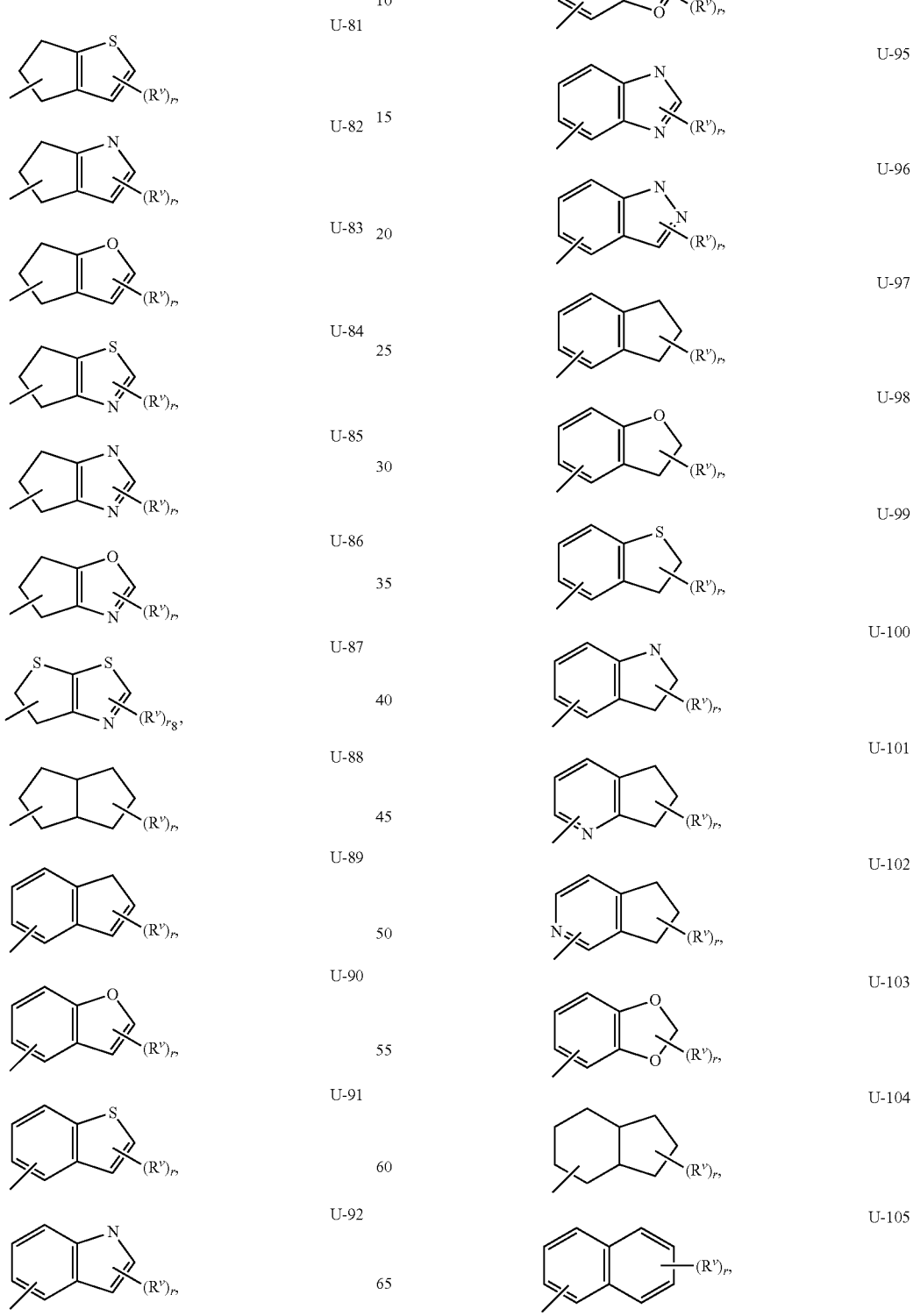

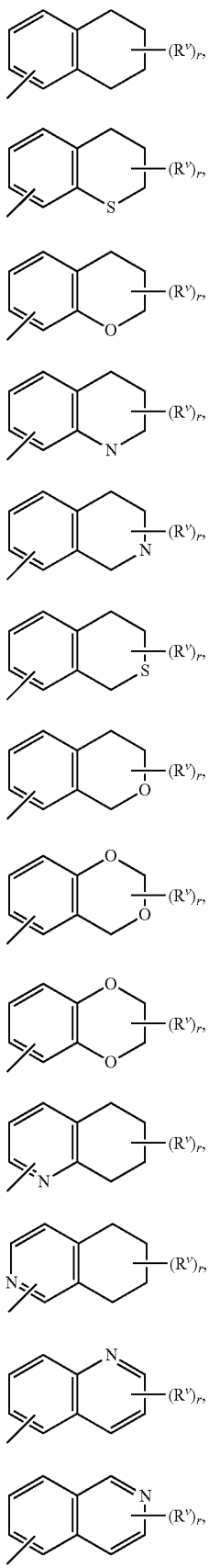

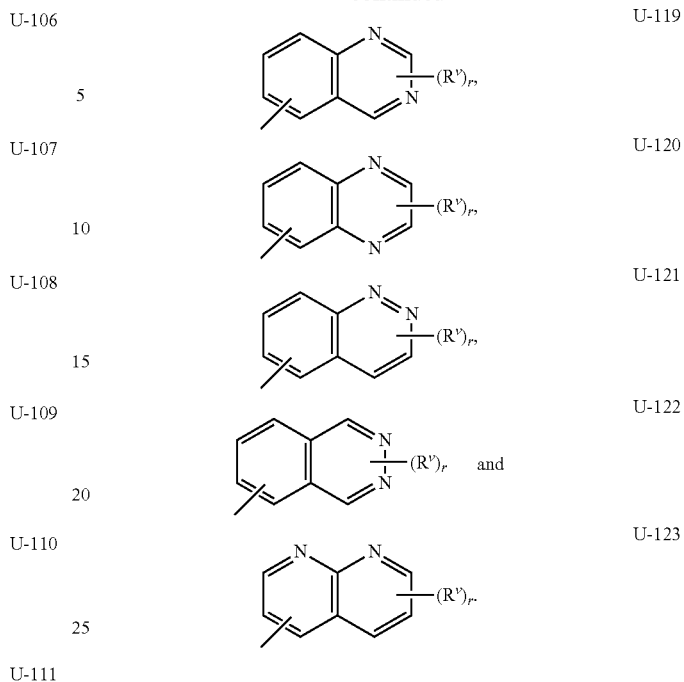

Although $R^v$ groups are shown in the structures U-1 through U-123, it is noted that they do not need to be present since they are optional substituents. Note that when $R^v$ is H when attached to an atom, this is the same as if said atom is unsubstituted. The nitrogen atoms that require substitution to fill their valence are substituted with H or $R^v$. Note that when the attachment point between $(R^v)_r$ and the U group is illustrated as floating, $(R^v)_r$ can be attached to any available carbon atom or nitrogen atom of the U group. Note that when the attachment point on the U group is illustrated as floating, the U group can be attached to the remainder of Formula 1 through any available carbon or nitrogen of the U group by replacement of a hydrogen atom. Note that some U groups can only be substituted with less than 4 $R^v$ groups (e.g., U-2 through U-5, U-7 through U-48, and U-52 through U-61).

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

Compounds of this invention can exist as one or more stereoisomers. The various stereoisomers include enantiomers, diastereomers, atropisomers and geometric isomers. Stereoisomers are isomers of identical constitution but differing in the arrangement of their atoms in space and include enantiomers, diastereomers, cis-trans isomers (also known as geometric isomers) and atropisomers. Atropisomers result from restricted rotation about single bonds where the rotational barrier is high enough to permit isolation of the isomeric species. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form. Particularly when $R^4$ and $R^5$ are each H, the $C(O)N(Q^2)(R^9)$ and $Q^1$ substituents are typically mostly in the thermodynamically preferred trans configuration on the pyrrolidinone ring.

For example, as shown in the following, the $C(O)N(Q^2)(R^9)$ moiety (i.e. a compound of Formula 1 wherein both $Y^1$ and $Y^2$ are O; $R^1$ is H; and J is $—CR^2R^3—$ and $R^2$ and $R^3$ are both H) bonded to the carbon at the 3-position of the ring and $Q^1$ bonded to the carbon at the 4-position of the ring are generally found in the trans configuration. These two carbon atoms both possess a chiral center. The most prevalant pair of enantiomers are depicted as Formula 1' and Formula 1". While this invention pertains to all stereoisomers, the preferred enantiomer for biological operability is identified as Formula 1'. For a comprehensive discussion of all aspects of stereoisomerism, see Ernest L. Eliel and Samuel H. Wilen, *Stereochemistry of Organic Compounds*, John Wiley & Sons, 1994.

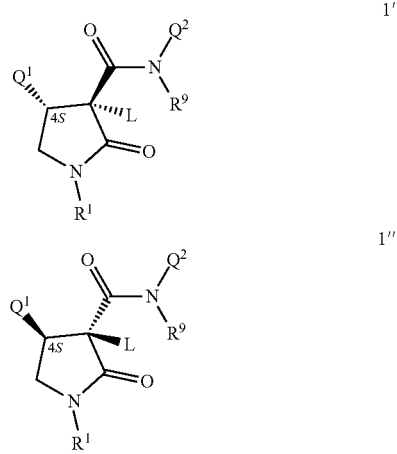

1'

1"

The skilled artisan will also recognize that the carbon atom at the 5-position of the pyrrolidinone ring (i.e. when J is $—CR^2R^3—$, the carbon atom to which both $R^2$ and $R^3$ are bonded) also contains a stereocenter indicated by a (*) as shown in Formula 1'''. This invention pertains to all stereoisomers, and therefore, when either $R^2$ or $R^3$ are other than the same substituent, then a mixture of diastereomers is possible.

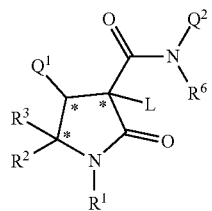

1'''

Molecular depictions drawn herein follow standard conventions for depicting stereochemistry. To indicate stereoconfiguration, bonds rising from the plane of the drawing and towards the viewer are denoted by solid wedges wherein the broad end of the wedge is attached to the atom rising from the plane of the drawing towards the viewer. Bonds going below the plane of the drawing and away from the viewer are denoted by dashed wedges wherein the narrow end of the wedge is attached to the atom closer to the viewer. Constant width lines indicate bonds with a direction opposite or neutral relative to bonds shown with solid or dashed wedges; constant width lines also depict bonds in molecules or parts of molecules in which no particular stereoconfiguration is intended to be specified.

This invention also comprises racemic mixtures, for example, equal amounts of the enantiomers of Formulae 1' and 1" (and optionally 1'''). In addition, this invention includes compounds that are enriched compared to the racemic mixture in an enantiomer of Formula 1.

Also included are the essentially pure enantiomers of compounds of Formula 1, for example, Formula 1' and Formula 1".

When enantiomerically enriched, one enantiomer is present in greater amounts than the other, and the extent of enrichment can be defined by an expression of enantiomeric excess ("ee"), which is defined as $(2x-1) \cdot 100\%$, where x is the mole fraction of the dominant enantiomer in the mixture (e.g., an ee of 20% corresponds to a 60:40 ratio of enantiomers).

Preferably the compositions of this invention have at least a 50% enantiomeric excess; more preferably at least a 75% enantiomeric excess; still more preferably at least a 90% enantiomeric excess; and the most preferably at least a 94% enantiomeric excess of the more active isomer. Of particular note are enantiomerically pure embodiments of the more active isomer.

Compounds of Formula 1 can comprise additional chiral centers. For example, substituents and other molecular constituents such as $R^4$ (i.e as a substituent on L-1) and L-2 through L-4 may themselves contain chiral centers. This invention comprises racemic mixtures as well as enriched and essentially pure stereoconfigurations at these additional chiral centers.

Compounds of this invention can exist as one or more conformational isomers due to restricted rotation about the amide bond (e.g., $C(O)N(Q^2)(R^9)$) in Formula 1. This invention comprises mixtures of conformational isomers. In addition, this invention includes compounds that are enriched in one conformer relative to others.

When enantiomerically enriched, one enantiomer is present in greater amounts than the other, and the extent of enrichment can be defined by an expression of enentiomeric ratio (ER) expressed as the relative area % of the two entantiomers determined by chiral high-performance liquid chromatography.

Preferably the compositions of this invention have at least a 50% ER; more preferably at least a 75% ER; still more preferably at least a 90% ER; and the most preferably at least a 94% ER of the more active isomer. Of particular note are enantiomerically pure embodiments of the more active isomer.

Compounds of Formula 1 can comprise additional chiral centers. For example, substituents and other molecular constituents such as $R^2$, $R^3$ and $R^6$ may themselves contain chiral centers. This invention comprises racemic mixtures as well as enriched and essentially pure stereoconfigurations at these additional chiral centers.

Compounds of Formula 1 typically exist in more than one form, and Formula 1 thus include all crystalline and non-crystalline forms of the compounds they represent. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound of Formula 1 can exhibit beneficial effects (e.g., suitability for preparation of useful formulations, improved biological performance) relative to another polymorph or a mixture of polymorphs of the same compound of Formula 1. Preparation and isolation of a particular polymorph of a compound of Formula 1 can be achieved by methods known to those skilled in the art including, for example, crystallization using selected solvents and temperatures. For a comprehensive discussion of polymorphism see R. Hilfiker, Ed., *Polymorphism in the Pharmaceutical Industry*, Wiley-VCH, Weinheim, 2006.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of a compound of Formula 1 are useful for control of undesired vegetation (i.e. are agriculturally suitable). The salts of a compound of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from Formula 1, stereoisomers, N-oxides and agriculturally suitable salts thereof.

Embodiments of the present invention as described in the Summary of the Invention include where Formula 1 as used in the following Embodiments includes N-oxides and salts thereof:

Embodiment 1. A compound of Formula 1, including all stereoisomers, N-oxides, and salts thereof, agricultural compositions containing them and their use as herbicides as described in the Summary of the Invention.

Embodiment 2. A compound of Embodiment 1 wherein L is selected from L-1, L-2 or L-3.

Embodiment 3. A compound of Embodiment 2 wherein L is selected from L-1 or L-2.

Embodiment 4. A compound of Embodiment 3 wherein L is L-1.

Embodiment 5. A compound of Embodiment 4 wherein L is L-2.

Embodiment 6. A compound of any one of Embodiments 1 through 5 wherein $R^A$ is $C_1$-$C_7$ alkyl, $C_1$-$C_7$ haloalkyl, $C_3$-$C_9$ cycloalkyl, $C_1$-$C_7$ alkoxy or $C_1$-$C_7$ haloalkoxy, $C_3$-$C_9$ cycloalkoxy, each substituted or unsubstituted with up to 2 substituents independently selected from $R^8$ or $G^1$; or
$R^A$ is $G^1$.

Embodiment 7. A compound of Embodiment 6 wherein $R^A$ is $C_1$-$C_7$ alkyl, $C_1$-$C_7$ haloalkyl, $C_1$-$C_7$ alkoxy or $C_1$-$C_7$ haloalkoxy, each substituted or unsubstituted with up to 2 substituents independently selected from $R^8$; or
$R^A$ is $G^1$.

Embodiment 8. A compound of Embodiment 7 wherein $R^A$ is $C_1$-$C_7$ alkyl or $C_1$-$C_7$ alkoxy, each substituted or unsubstituted with up to 2 substituents independently selected from $R^8$.

Embodiment 9. A compound of Embodiment 8 wherein $R^A$ is $C_1$-$C_3$ alkyl, substituted or unsubstituted with up to 2 substituents independently selected from $R^8$.

Embodiment 10. A compound of Embodiment 8 wherein $R^A$ is $C_1$-$C_3$ alkoxy, substituted or unsubstituted with up to 2 substituents independently selected from $R^8$.

Embodiment 11. A compound of any one of Embodiments 1 through 4 wherein $R^B$ is H, $C_1$-$C_4$ alkoxy, $C_1$-$C_4$ haloalkyl or $C_1$-$C_4$ alkyl.

Embodiment 12. A compound of Embodiment 11 wherein $R^B$ is H, —$OCH_3$, $CF_3$ or $CH_3$.

Embodiment 13. A compound of Embodiment 12 wherein $R^B$ is H, —$OCH_3$ or $CH_3$.

Embodiment 14. A compound of Embodiment 13 wherein $R^B$ is H.

Embodiment 15. A compound of any one of Embodiments 1 through 4 or 11 through 15 wherein $R^C$ is H, $C_1$-$C_4$ alkoxy, $C_1$-$C_4$ haloalkyl or $C_1$-$C_4$ alkyl.

Embodiment 16. A compound of Embodiment 15 wherein $R^C$ is H, $C_1$-$C_2$ alkoxy or $C_1$-$C_2$ alkyl.

Embodiment 17. A compound of Embodiment 16 wherein $R^C$ is H or $CH_3$.

Embodiment 18. A compound of Embodiment 17 wherein $R^C$ is H.

Embodiment 19. A compound of Embodiment 18 wherein $R^D$ is H, $C_1$-$C_3$ alkyl or $C_2$-$C_3$ alkylcarbonyl.

Embodiment 20. A compound of Embodiment 19 wherein $R^D$ is H, $CH_3$, $CH_2CH_3$ or —$C(=O)CH_3$.

Embodiment 21. A compound of Embodiment 20 wherein $R^D$ is H.

Embodiment 22. A compound of Embodiment 20 wherein $R^D$ is $CH_3$ or $CH_2CH_3$.

Embodiment 23. A compound of Embodiment 20 wherein $R^D$ is —C(=O)CH$_3$.

Embodiment 24. A compound of any one of Embodiments 1 through 4 or 11 through 23 wherein $R^E$ is H, hydroxy, amino, cyano, formyl, —C(O)NH$_2$, $C_1$-$C_6$ alkyl, $C_1$-$C_6$ haloalkyl, $C_2$-$C_6$ cyanoalkyl, $C_3$-$C_6$ cycloalkyl, $C_4$-$C_8$ cycloalkylalkyl, $C_2$-$C_8$ alkoxyalkyl, $C_3$-$C_8$ alkoxyalkoxyalkyl, $C_2$-$C_8$ haloalkoxyalkyl, $C_2$-$C_8$ alkenyl, $C_2$-$C_8$ haloalkenyl, $C_2$-$C_8$ alkenylalkyl, $C_2$-$C_8$ haloalkenylalkyl, $C_2$-$C_8$ alkylcarbonyl, $C_2$-$C_8$ haloalkylcarbonyl, $C_4$-$C_{10}$ cycloalkylcarbonyl, $C_5$-$C_{10}$ cycloalkylcarbonylalkyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl or $C_2$-$C_8$ dialkylaminosulfonyl.

Embodiment 25. A compound of Embodiment 24 wherein $R^E$ is H, hydroxy, amino, cyano, formyl, —C(O)NH$_2$, $C_1$-$C_6$ alkyl, $C_3$-$C_6$ cycloalkyl, $C_4$-$C_8$ cycloalkylalkyl, $C_2$-$C_8$ alkoxyalkyl, $C_3$-$C_8$ alkoxyalkoxyalkyl, $C_2$-$C_8$ alkylcarbonyl, $C_4$-$C_{10}$ cycloalkylcarbonyl, $C_5$-$C_{10}$ cycloalkylcarbonylalkyl, $C_2$-$C_8$ alkoxycarbonyl, $C_4$-$C_{10}$ cycloalkoxycarbonyl, $C_1$-$C_6$ alkylsulfonyl.

Embodiment 26. A compound of Embodiment 25 wherein $R^E$ is H, $C_1$-$C_6$ alkyl, $C_3$-$C_6$ cycloalkyl, $C_4$-$C_8$ cycloalkylalkyl, $C_2$-$C_8$ alkoxyalkyl, $C_2$-$C_8$ alkylcarbonyl, $C_2$-$C_8$ alkoxycarbonyl, $C_4$-$C_{10}$ cycloalkoxycarbonyl, $C_1$-$C_6$ alkylsulfonyl.

Embodiment 27. A compound of Embodiment 26 wherein $R^E$ is H, $C_1$-$C_6$ alkyl or $C_2$-$C_8$ alkylcarbonyl.

Embodiment 28. A compound of Embodiment 27 wherein $R^E$ is H, $C_1$-$C_2$ alkyl or $C_2$-$C_4$ alkylcarbonyl.

Embodiment 29. A compound of any one of Embodiments 1, 2 or 11 through 18 wherein $R^F$ is formyl, —C(O)NH$_2$, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, —P(=O)(OH)$_2$, $C_1$-$C_6$ dialkylphosphoryl, $C_1$-$C_6$ haloalkylphosphoryl, $C_3$-$C_8$ cycloalkylphosphoryl, $C_2$-$C_8$ dialkoxyphosphoryl, $C_6$-$C_{14}$ dicycloalkoxyphosphoryl, $C_8$-$C_{16}$ dicycloalkylalkoxyphosphoryl, $C_2$-$C_{12}$ bis(alkylamino)phosphoryl, $C_4$-$C_{24}$ bis(dialkylamino)phosphoryl; or phenyl substituted or unsubstituted with $R^{16}$.

Embodiment 30. A compound of Embodiment 29 wherein $R^F$ is $C_2$-$C_8$ alkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkylsulfonyl, $C_1$-$C_6$ haloalkylsulfonyl, $C_3$-$C_8$ cycloalkylsulfonyl or $C_1$-$C_6$ alkylaminosulfonyl; or phenyl substituted or unsubstituted with $R^{16}$.

Embodiment 31. A compound of Embodiment 30 wherein $R^F$ is $C_2$-$C_8$ alkylcarbonyl, $C_2$-$C_8$ alkoxycarbonyl, $C_2$-$C_8$ haloalkoxycarbonyl, $C_2$-$C_8$ alkylaminocarbonyl, $C_3$-$C_{10}$ dialkylaminocarbonyl or $C_1$-$C_6$ alkylsulfonyl.

Embodiment 32. A compound of Embodiment 31 wherein $R^F$ is $C_2$-$C_4$ alkylcarbonyl or $C_2$-$C_4$ alkoxycarbonyl.

Embodiment 33. A compound of any one of Embodiments 1 through 3 or 11 through 18 wherein $R^G$ is formyl, —C(O)NH$_2$, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl or $C_1$-$C_6$ alkylaminosulfonyl.

Embodiment 34. A compound of Embodiment 33 wherein $R^G$ is formyl, $C_2$-$C_8$ alkylcarbonyl, $C_2$-$C_8$ alkoxycarbonyl, $C_4$-$C_{10}$ cycloalkoxycarbonyl, $C_2$-$C_8$ alkylaminocarbonyl, $C_4$-$C_{10}$ cycloalkylaminocarbonyl, $C_1$-$C_6$ alkylsulfonyl, $C_1$-$C_6$ haloalkylsulfonyl, $C_3$-$C_8$ cycloalkylsulfonyl or $C_1$-$C_6$ alkylaminosulfonyl.

Embodiment 35. A compound of Embodiment 34 wherein $R^G$ is formyl, $C_2$-$C_8$ alkylcarbonyl, $C_2$-$C_8$ alkoxycarbonyl or $C_4$-$C_{10}$ cycloalkoxycarbonyl.

Embodiment 36. A compound of Embodiment 35 wherein $R^G$ is $C_2$-$C_8$ alkylcarbonyl or $C_2$-$C_8$ alkoxycarbonyl.

Embodiment 37. A compound of Embodiment 36 wherein $R^G$ is $C_2$-$C_4$ alkylcarbonyl or $C_2$-$C_4$ alkoxycarbonyl.

Embodiment 38. A compound of any one of Embodiments 1 through 11 wherein each $R^8$ is independently cyano, nitro, —CHO, $C_2$-$C_6$ alkenyl, $C_2$-$C_6$ alkynyl, $C_2$-$C_8$ alkylcarbonyl, $C_2$-$C_8$ haloalkylcarbonyl, $C_2$-$C_8$ alkoxycarbonyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_1$-$C_6$ alkoxy, $C_1$-$C_6$ haloalkoxy or $C_2$-$C_8$ alkylcarbonyloxy.

Embodiment 39. A compound of Embodiment 38 wherein each $R^8$ is independently $C_2$-$C_6$ alkenyl, $C_1$-$C_6$ alkoxy or $C_1$-$C_6$ haloalkoxy.

Embodiment 40. A compound of Embodiment 39 wherein each $R^8$ is independently $C_1$-$C_6$ alkoxy or $C_1$-$C_6$ haloalkoxy.

Embodiment 40A. A compound of Embodiment 40 wherein each $R^8$ is independently $C_1$-$C_6$ alkoxy.

Embodiment 41. A compound of any one of Embodiments 1 through 40A wherein J is —CR$^2$R$^3$—, —CR$^2$R$^3$—CR$^4$R$^5$— or —NR$^6$—.

Embodiment 42. A compound of Embodiment 41 wherein J is —CR$^2$R$^3$— or —CR$^2$R$^3$—CR$^4$R$^5$—.

Embodiment 43. A compound of Embodiment 42 wherein J is —CR$^2$R$^3$—CR$^4$R$^5$—.

Embodiment 44. A compound of Embodiment 43 wherein J is —CR$^2$R$^3$—.

Embodiment 45. A compound of any one of Embodiments 1 through 44 wherein $Y^1$ and $Y^2$ are each independently O or S.

Embodiment 46. A compound of Embodiment 45 wherein $Y^1$ and $Y^2$ are each independently S.

Embodiment 47. A compound of Embodiment 46 wherein $Y^1$ and $Y^2$ are each independently O.

Embodiment 48. A compound of any one of Embodiments 1 through 47 wherein $R^1$ is H, CHO, $C_3$-$C_8$ alkylcarbonylalkyl, $C_1$-$C_6$ alkyl, $C_1$-$C_6$ haloalkyl, $C_2$-$C_6$ alkenyl, $C_3$-$C_6$ alkynyl, $C_2$-$C_6$ cyanoalkyl, $C_3$-$C_6$ cycloalkyl, $C_4$-$C_8$ cycloalkylalkyl, $C_2$-$C_8$ alkoxyalkyl, $C_3$-$C_8$ alkoxyalkoxyalkyl, $C_2$-$C_8$ haloalkoxyalkyl, $C_2$-$C_8$ alkylthioalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_2$-$C_8$ alkylaminocarbonyl, $C_3$-$C_{10}$ dialkylaminocarbonyl or $C_4$-$C_{10}$ cycloalkylaminocarbonyl.

Embodiment 49. A compound of Embodiment 48 wherein $R^1$ is H, $C_3$-$C_8$ alkylcarbonylalkyl, $C_1$-$C_6$ alkyl, $C_1$-$C_6$ haloalkyl, $C_2$-$C_6$ cyanoalkyl, $C_3$-$C_6$ cycloalkyl, $C_4$-$C_8$ cycloalkylalkyl, $C_2$-$C_8$ alkoxyalkyl, $C_2$-$C_8$ haloalkoxyalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl or $C_2$-$C_8$ haloalkoxycarbonyl.

Embodiment 50. A compound of Embodiment 49 wherein $R^1$ is H, $C_1$-$C_6$ alkyl, $C_1$-$C_6$ haloalkyl, $C_2$-$C_6$ cyanoalkyl, $C_3$-$C_6$ cycloalkyl, $C_4$-$C_8$ cycloalkylalkyl, $C_2$-$C_8$ alkoxyalkyl, $C_2$-$C_8$ haloalkoxyalkyl or $C_2$-$C_8$ alkoxycarbonyl.

Embodiment 51. A compound of Embodiment 50 wherein $R^1$ is H, $C_1$-$C_6$ alkyl, $C_3$-$C_6$ cycloalkyl, $C_4$-$C_8$ cycloalkylalkyl or $C_2$-$C_8$ alkoxyalkyl.

Embodiment 52. A compound of Embodiment 51 wherein $R^1$ is H, $CH_3$, $CH_2CH_3$, cyclopropyl, cyclopropylmethyl or $CH_2OCH_3$.

Embodiment 53. A compound of any one of Embodiments 1 through 52 wherein $Q^1$ is a phenyl ring or a naphthalenyl ring system, each ring or ring system substituted or unsubstituted with up to 5 substituents independently selected from $R^{10}$; or a 5- to 6-membered heterocyclic ring; or an 8- to 10-membered bicyclic ring system, each ring or ring system containing ring members selected from carbon atoms and 1 to 4 heteroatoms independently selected from up to 2 O, up to 2 S and up to 4 N atoms, wherein up to 2 carbon ring members are independently selected from $C(=O)$ and $C(=S)$, and the sulfur atom ring members are independently selected from $S(=O)_u(=NR^{14})_v$, each ring or ring system substituted or unsubstituted with up to 4 substituents independently selected from $R^{10}$ on carbon atom ring members and selected from $R^{12}$ on nitrogen atom ring members.

Embodiment 54. A compound of Embodiment 53 wherein $Q^1$ is a phenyl ring substituted or unsubstituted with up to 4 substituents independently selected from $R^{10}$; or a 5- to 6-membered heterocyclic ring, each ring containing ring members selected from carbon atoms and 1 to 4 heteroatoms independently selected from up to 2 O, up to 2 S and up to 4 N atoms, each ring substituted or unsubstituted with up to 4 substituents independently selected from $R^{10}$ on carbon atom ring members and selected from $R^{12}$ on nitrogen atom ring members.

Embodiment 55. A compound of Embodiment 54 wherein $Q^1$ is a phenyl ring substituted or unsubstituted with up to 4 substituents independently selected from $R^{10}$.

Embodiment 56. A compound of Embodiment 55 wherein $Q^1$ is a phenyl ring substituted or unsubstituted with up to 3 substituents independently selected from $R^{10}$.

Embodiment 57. A compound of Embodiment 56 wherein $Q^1$ is a phenyl ring substituted or unsubstituted with up to 2 substituents independently selected from $R^{10}$.

Embodiment 58. A compound of Embodiment 57 wherein $Q^1$ is a phenyl ring substituted with up 2 substituents independently selected from $R^{10}$.

Embodiment 59. A compound of Embodiment 58 wherein $Q^1$ is a phenyl ring substituted with up 2 substituents independently selected from $R^{10}$ where one substituent is at the para (4-) position.

Embodiment 60. A compound of Embodiment 59 wherein $Q^1$ is a phenyl ring substituted with up 2 substituents independently selected from $R^{10}$ where one substituent is at the meta (3-) position.

Embodiment 61. A compound of any one of Embodiments 1 through 60 wherein $Q^1$ is other than an unsubstituted phenyl ring.

Embodiment 62. A compound of Embodiment 61 wherein $Q^1$ is an 8- to 10-membered bicyclic ring system containing ring members selected from carbon atoms and 1 to 4 heteroatoms independently selected from up to 2 O atoms, each ring system optionally substituted with up to 4 substituents independently selected from $R^{10}$ on carbon atom ring members.

Embodiment 63. A compound of Embodiment 62 wherein $Q^1$ is a 9-membered bicyclic ring system containing ring members selected from carbon atoms and 1 to 4 heteroatoms independently selected from up to 2 O atoms, each ring system optionally substituted with up to 4 substituents independently selected from $R^{10}$ on carbon atom ring members.

Embodiment 64. A compound of Embodiment 63 wherein $Q^1$ is a 9-membered heteroaromatic bicyclic ring system containing ring members selected from carbon atoms and 2 O atoms, system optionally substituted with up to 3 substituents independently selected from $R^{10}$ on carbon atom ring members (i.e. U-103 in Exhibit 3).

Embodiment 65. A compound of Embodiment 64 wherein $Q^1$ is U-103A:

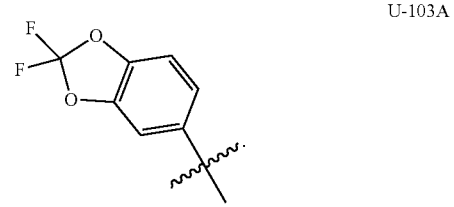 [SMILES: *c1ccc2c(c1)OC(F)(F)O2]

U-103A

Embodiment 66. A compound of any one of Embodiments 1 through 65 wherein $Q^2$ is a phenyl ring, each ring substituted or unsubstituted with up to 4 substituents independently selected from $R^{11}$; or a 5- to 6-membered heterocyclic ring; or an 8- to 10-membered bicyclic ring system, each ring or ring system containing ring members selected from carbon atoms and 1 to 4 heteroatoms independently selected from up to 2 O, up to 2 S and up to 4 N atoms, wherein up to 2 carbon ring members are independently selected from $C(=O)$ and $C(=S)$, and the sulfur atom ring members are independently selected from $S(=O)_u(=NR^{14})_v$, each ring or ring system substituted or unsubstituted with up to 4 substituents independently selected from $R^{11}$ on carbon atom ring members and selected from $R^{13}$ on nitrogen atom ring members.

Embodiment 67. A compound of Embodiment 66 wherein $Q^2$ is a phenyl ring, substituted or unsubstituted with up to 4 substituents independently selected from $R^{11}$; or a 5- to 6-membered heterocyclic ring; or an 8- to 10-membered bicyclic ring system, each ring or ring system containing ring members selected from carbon atoms and 1 to 4 heteroatoms independently selected from up to 2 O, up to 2 S and up to 4 N atoms, wherein up to 2 carbon ring members are independently selected from $C(=O)$ and $C(=S)$, and the sulfur atom ring members are independently selected from $S(=O)_u$ (=NR$^{14}$)$_v$, each ring or ring system substituted or unsubstituted with up to 4 substituents independently selected from R$^{11}$ on carbon atom ring members and selected from R$^{13}$ on nitrogen atom ring members.

Embodiment 68. A compound of Embodiment 67 wherein Q$^2$ is a phenyl ring, substituted or unsubstituted with up to 4 substituents independently selected from R$^{11}$; or a 5- to 6-membered heterocyclic ring containing ring members selected from carbon atoms and 1 to 4 heteroatoms independently selected from up to 4 N atoms, wherein up to 2 carbon ring members are independently selected from C(=O) and C(=S), each ring or ring system substituted or unsubstituted with up to 4 substituents independently selected from R$^{11}$ on carbon atom ring members and selected from R$^{13}$ on nitrogen atom ring members.

Embodiment 69. A compound of Embodiment 68 wherein Q$^2$ is a phenyl ring, substituted or unsubstituted with up to 4 substituents independently selected from R$^{11}$.

Embodiment 70. A compound of Embodiment 69 wherein Q$^2$ is a phenyl ring, substituted or unsubstituted with up to 3 substituents independently selected from R$^{11}$.

Embodiment 71. A compound of Embodiment 70 wherein Q$^2$ is a phenyl ring, substituted or unsubstituted with up to 2 substituents independently selected from R$^{11}$.

Embodiment 72. A compound of Embodiment 71 wherein Q$^2$ is a phenyl ring, substituted with at least 2 substituents independently selected from R$^{11}$ where one substituent is at the ortho (2-) position.

Embodiment 73. A compound of Embodiment 72 wherein Q$^2$ is a phenyl ring, substituted with at least 2 substituents independently selected from R$^{11}$ where one substituent is at the meta (3-) position.

Embodiment 74. A compound of any one of Embodiments 1 through 73 wherein Q$^2$ is other than an unsubstituted phenyl ring.

Embodiment 75. A compound of any one of Embodiments 1 through 74 wherein R$^2$ and R$^3$ are each independently H or C$_1$-C$_4$ alkyl.

Embodiment 76. A compound of Embodiment 75 wherein R$^2$ and R$^3$ are each independently H or CH$_3$.

Embodiment 77. A compound of Embodiment 76 wherein R$^2$ and R$^3$ are each independently H.

Embodiment 78. A compound of any one of Embodiments 1 through 77 wherein R$^4$ and R$^5$ are each independently H, halogen, C$_1$-C$_4$ alkyl or C$_1$-C$_4$ alkoxy.

Embodiment 79. A compound of Embodiment 78 wherein R$^4$ and R$^5$ are each independently H, halogen or C$_1$-C$_4$ alkyl.

Embodiment 80. A compound of Embodiment 79 wherein R$^4$ and R$^5$ are each independently H, Cl or CH$_3$.

Embodiment 81. A compound of any one of Embodiments 1 through 80 wherein R$^6$ is H, C$_1$-C$_6$ alkyl or C$_1$-C$_6$ alkoxy.

Embodiment 82. A compound of Embodiment 81 wherein R$^6$ is H or C$_1$-C$_6$ alkyl.

Embodiment 83. A compound of Embodiment 82 wherein R$^6$ is H or CH$_3$.

Embodiment 84. A compound of Embodiment 83 wherein R$^6$ is H.

Embodiment 85. A compound of any one of Embodiments 1 through 47 or 53 through 84 wherein R$^1$ and R$^6$ are taken together as C$_3$ alkylene or —CH$_2$OCH$_2$—.

Embodiment 86. A compound of Embodiment 85 wherein R$^1$ and R$^6$ are taken together as C$_3$ alkylene.

Embodiment 87. A compound of any one of Embodiments 1 through 86 wherein R$^7$ is H, halogen, C$_1$-C$_4$ alkoxy or C$_1$-C$_4$ alkyl.

Embodiment 88. A compound of Embodiment 87 wherein R$^7$ is H, F, Cl or CH$_3$.

Embodiment 89. A compound of any one of Embodiments 1 through 88 wherein R$^7$ is H or CH$_3$.

Embodiment 90. A compound of Embodiment 89 wherein R$^7$ is H.

Embodiment 91. A compound of any one of Embodiments 1 through 90 wherein R$^9$ is H, C$_1$-C$_6$ alkyl, C$_2$-C$_8$ alkoxyalkyl, C$_2$-C$_8$ alkylthioalkyl, C$_2$-C$_8$ alkylsulfinylalkyl, C$_2$-C$_8$ alkylsulfonylalkyl, C$_2$-C$_8$ alkylcarbonyl, C$_4$-C$_{10}$ cycloalkylcarbonyl, C$_2$-C$_8$ alkoxycarbonyl or C$_4$-C$_{10}$ cycloalkoxycarbonyl.

Embodiment 92. A compound of Embodiment 91 wherein R$^9$ is H, C$_1$-C$_6$ alkyl, C$_2$-C$_8$ alkoxyalkyl, C$_2$-C$_8$ alkylcarbonyl or C$_2$-C$_8$ alkoxycarbonyl.

Embodiment 93. A compound of Embodiment 92 wherein R$^9$ is H, C$_1$-C$_6$ alkyl or C$_2$-C$_8$ alkoxycarbonyl.

Embodiment 94. A compound of Embodiment 93 wherein R$^9$ is H, CH$_3$ or —C(=O)CH$_3$.

Embodiment 95. A compound of Embodiment 94 wherein R$^9$ is H.

Embodiment 96. A compound of any one of Embodiments 1 through 95 wherein each R$^{10}$ and R$^{11}$ is halogen, nitro, C$_1$-C$_8$ alkyl, C$_1$-C$_8$ cyanoalkyl, C$_1$-C$_8$ cyanoalkoxy, C$_1$-C$_8$ haloalkyl, C$_1$-C$_8$ nitroalkyl, C$_2$-C$_8$ alkenyl, C$_2$-C$_8$ haloalkenyl, C$_2$-C$_8$ nitroalkenyl, C$_2$-C$_8$ alkoxyalkyl, C$_3$-C$_8$ alkoxyalkoxyalkyl, C$_2$-C$_8$ haloalkoxyalkyl, C$_2$-C$_8$ haloalkoxyhaloalkoxy, C$_4$-C$_{10}$ cycloalkylalkyl, C$_4$-C$_{10}$ halocycloalkylalkyl, C$_5$-C$_{12}$ alkylcycloalkylalkyl, C$_5$-C$_{12}$ cycloalkylalkenyl, C$_3$-C$_8$ cycloalkyl, C$_3$-C$_8$ halocycloalkyl, C$_4$-C$_{10}$ alkylcycloalkyl, C$_6$-C$_{12}$ cycloalkylcycloalkyl, C$_3$-C$_8$ cycloalkenyl, C$_3$-C$_8$ halocycloalkenyl, C$_2$-C$_8$ haloalkoxyalkoxy, C$_2$-C$_8$ alkoxyalkoxy, C$_4$-C$_{10}$ cycloalkoxyalkyl, C$_2$-C$_8$ alkylcarbonyl, C$_2$-C$_8$ haloalkylcarbonyl, C$_4$-C$_{10}$ cycloalkylcarbonyl, —C(=O)OH, C$_2$-C$_8$ alkoxycarbonyl, C$_2$-C$_8$ haloalkoxycarbonyl, C$_4$-C$_{10}$ cycloalkoxycarbonyl, C$_5$-C$_{12}$ cycloalkylalkoxycarbonyl, —C(=O)NH$_2$, C$_1$-C$_8$ alkoxy, C$_1$-C$_8$ haloalkoxy, C$_2$-C$_8$ alkenyloxy, C$_2$-C$_8$ haloalkenyloxy, C$_3$-C$_8$ cycloalkoxy, C$_3$-C$_8$ halocycloalkoxy, C$_4$-C$_{10}$ cycloalkylalkoxy, C$_3$-C$_{10}$ alkylcarbonylalkoxy, C$_2$-C$_8$ alkylcarbonyloxy, C$_2$-C$_8$ haloalkylcarbonyloxy, C$_4$-C$_{10}$ cycloalkylcarbonyloxy, C$_1$-C$_8$ alkylsulfonyloxy, C$_1$-C$_8$ haloalkylsulfonyloxy, C$_1$-C$_8$ alkylsulfonyl, C$_1$-C$_8$ haloalkylsulfonyl, C$_3$-C$_8$ cycloalkylsulfonyl.

Embodiment 97. A compound of Embodiment 96 wherein each R$^{10}$ and R$^{11}$ is independently halogen, C$_1$-C$_8$ alkyl, C$_1$-C$_8$ haloalkyl, C$_2$-C$_8$ alkoxyalkyl, C$_3$-C$_8$ alkoxyalkoxyalkyl, C$_4$-C$_{10}$ cycloalkylalkyl, C$_5$-C$_{12}$ alkylcycloalkylalkyl, C$_3$-C$_8$ cycloalkyl, C$_3$-C$_8$ halocycloalkyl, C$_6$-C$_{12}$ cycloalkylcycloalkyl, C$_3$-C$_8$ halocycloalkenyl, C$_2$-C$_8$ haloalkoxyalkoxy, C$_2$-C$_8$ alkoxyalkoxy, C$_4$-C$_{10}$ cycloalkoxyalkyl, C$_2$-C$_8$ alkylcarbonyl, C$_2$-C$_8$ haloalkylcarbonyl, C$_4$-C$_{10}$ cycloalkylcarbonyl, C$_2$-C$_8$ alkoxycarbonyl, C$_4$-C$_{10}$ cycloalkoxycarbonyl, C$_5$-C$_{12}$ cycloalkylalkoxycarbonyl, C$_1$-C$_8$ alkoxy, C$_1$-C$_8$ haloalkoxy, C$_2$-C$_8$ haloalkenyloxy, C$_3$-C$_8$ cycloalkoxy, C$_3$-C$_8$ halocycloalkoxy, C$_4$-C$_{10}$ cycloalkylalkoxy, C$_3$-C$_{10}$ alkylcarbonylalkoxy or C$_2$-C$_8$ haloalkylcarbonyloxy.

Embodiment 98. A compound of Embodiment 97 wherein each R$^{10}$ and R$^{11}$ is independently halogen, C$_1$-C$_8$ alkyl, C$_1$-C$_8$ haloalkyl, C$_2$-C$_8$ alkoxyalkyl, C$_4$-C$_{10}$ cycloalkylalkyl, $C_5$-$C_{12}$ alkylcycloalkylalkyl, $C_3$-$C_8$ cycloalkyl, $C_3$-$C_8$ halocycloalkyl, $C_2$-$C_8$ haloalkoxyalkoxy, $C_1$-$C_8$ alkoxy, $C_1$-$C_8$ haloalkoxy or $C_2$-$C_8$ alkoxyalkoxy.

Embodiment 99. A compound of Embodiment 98 wherein each $R^{10}$ and $R^{11}$ is independently halogen, $C_1$-$C_8$ alkyl, $C_1$-$C_8$ haloalkyl, $C_3$-$C_8$ cycloalkyl, $C_1$-$C_8$ alkoxy or $C_1$-$C_8$ haloalkoxy.

Embodiment 100. A compound of Embodiment 99 wherein each $R^{10}$ and $R^{11}$ is independently halogen, $C_1$-$C_8$ alkyl, $C_1$-$C_8$ haloalkyl, $C_1$-$C_8$ alkoxy or $C_1$-$C_8$ haloalkoxy.

Embodiment 101. A compound of Embodiment 100 wherein each $R^{10}$ and $R^{11}$ is independently halogen or $C_1$-$C_8$ alkyl.

Embodiment 102. A compound of Embodiment 100 wherein each $R^{10}$ and $R^{11}$ is independently halogen or $C_1$-$C_8$ haloalkyl.

Embodiment 103. A compound of Embodiment 100 wherein each $R^{10}$ and $R^{11}$ is independently halogen or $C_1$-$C_8$ alkoxy.

Embodiment 104. A compound of Embodiment 100 wherein each $R^{10}$ and $R^{11}$ is independently halogen or $C_1$-$C_8$ haloalkoxy.

Embodiment 105. A compound of Embodiment 100 wherein each $R^{10}$ and $R^{11}$ is independently $C_1$-$C_8$ alkyl or $C_1$-$C_8$ alkoxy.

Embodiment 106. A compound of Embodiment 100 wherein each $R^{10}$ and $R^{11}$ is independently $C_1$-$C_8$ alkyl or $C_1$-$C_8$ haloalkyl.

Embodiment 107. A compound of any one of Embodiments 1 through 106 wherein each $R^{12}$ and $R^{13}$ is independently $C_1$-$C_3$ alkyl, $C_2$-$C_3$ alkenyl, $C_3$-$C_6$ cycloalkyl, $C_2$-$C_3$ alkoxyalkyl, $C_2$-$C_3$ alkylcarbonyl or $C_2$-$C_3$ alkylaminoalkyl.

Embodiment 108. A compound of Embodiment 107 wherein each $R^{12}$ and $R^{13}$ is independently $C_1$-$C_3$ alkyl, $C_3$-$C_6$ cycloalkyl or $C_2$-$C_3$ alkylcarbonyl.

Embodiment 109. A compound of Embodiment 108 wherein each $R^{12}$ and $R^{13}$ is independently $C_1$-$C_3$ alkyl or $C_2$-$C_3$ alkylcarbonyl.

Embodiment 110. A compound of Embodiment 109 wherein each $R^{12}$ and $R^{13}$ is independently $C_1$-$C_3$ alkyl.

Embodiment 111. A compound of Embodiment 110 wherein each $R^{12}$ and $R^{13}$ is independently $CH_3$.

Embodiment 112. A compound of any one of Embodiments 1 through 111 wherein each $R^{14}$ is independently H or —(C=O)CH$_3$.

Embodiment 113. A compound of Embodiment 112 wherein each $R^{14}$ is independently H.

Embodiment 114. A compound of any one of Embodiments 1 through 113 wherein $R^{15}$ is H, CHO, $C_1$-$C_4$ alkyl, $C_2$-$C_6$ alkylcarbonyl or $C_2$-$C_6$ haloalkylcarbonyl.

Embodiment 115. A compound of Embodiment 114 wherein $R^{15}$ is H, $CH_3$, —(C=O)CH$_3$ or —(C=O)CF$_3$.

Embodiment 116. A compound of Embodiment 115 wherein each $R^{15}$ is independently H or $CH_3$.

Embodiment 117. A compound of any one of Embodiments 1 through 116 wherein each $G^1$ is independently phenyl; or a 6-membered heterocyclic ring, each substituted or unsubstituted on ring members with up to 4 substituents independently selected from $R^{17}$.

Embodiment 118. A compound of Embodiment 117 wherein each $G^1$ is independently phenyl substituted or unsubstituted on ring members with up to 3 substituents independently selected from $R^{17}$.

Embodiment 119. A compound of any one of Embodiments 1 through 118 wherein each $R^{16}$, $R^{17}$ and $R^{18}$ is independently halogen, cyano, hydroxy, amino, nitro, —CHO, —C(=O)OH, —C(=O)NH$_2$, —SO$_2$NH$_2$, $C_1$-$C_6$ alkyl, $C_1$-$C_6$ haloalkyl, $C_2$-$C_6$ alkenyl, $C_2$-$C_6$ alkynyl, $C_2$-$C_8$ alkylcarbonyl, $C_1$-$C_8$ hydroxyalkyl, $C_2$-$C_8$ haloalkylcarbonyl, $C_2$-$C_6$ alkoxyalkyl, $C_2$-$C_6$ alkylaminoalkyl, $C_2$-$C_8$ alkoxycarbonyl, $C_3$-$C_8$ cycloalkyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_3$-$C_8$ dialkylaminoalkyl, $C_1$-$C_6$ alkoxy, $C_1$-$C_6$ haloalkoxy, $C_2$-$C_8$ alkylcarbonyloxy or $C_1$-$C_6$ alkylthio.

Embodiment 120. A compound of Embodiment 119 wherein each $R^{16}$, $R^{17}$ and $R^{18}$ is independently halogen, cyano, hydroxy, amino, nitro, —CHO, —C(=O)OH, —C(=O)NH$_2$, —SO$_2$NH$_2$, $C_1$-$C_6$ alkyl or $C_1$-$C_6$ haloalkyl.

Embodiment 121. A compound of Embodiment 120 wherein each $R^{16}$, $R^{17}$ and $R^{18}$ is independently halogen, nitro, $C_1$-$C_6$ alkyl or $C_1$-$C_6$ haloalkyl.

Embodiment 122. A compound of Embodiment 121 wherein each $R^{16}$, $R^{17}$ and $R^{18}$ is independently halogen, $C_1$-$C_6$ alkyl or $C_1$-$C_6$ haloalkyl.

Embodiment 123. A compound of Embodiment 122 wherein each $R^{16}$, $R^{17}$ and $R^{18}$ is independently halogen or $C_1$-$C_6$ alkyl.

Embodiment 124. A compound of Embodiment 123 wherein each $R^{16}$, $R^{17}$ and $R^{18}$ is independently halogen.

Embodiment 125. A compound of any one of Embodiments 1 through 124 provided the sum of u and v is 0.

Embodiment 126. A compound of any one of Embodiments 1 through 125 provided the sum of u and v is 2.

Embodiments of this invention, including Embodiments 1-126 above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this invention, including Embodiments 1-126 above as well as any other embodiments described herein, and any combination thereof, pertain to the compositions and methods of the present invention.

Embodiment A. A compound of Summary of the Invention 1 wherein:
$R^A$ is $C_1$-$C_7$ alkyl, $C_1$-$C_7$ haloalkyl, $C_3$-$C_9$ cycloalkyl, $C_1$-$C_7$ alkoxy or $C_1$-$C_7$ haloalkoxy, $C_3$-$C_9$ cycloalkoxy, each substituted or unsubstituted with up to 2 substituents independently selected from $R^8$ or $G^1$; or
$R^A$ is $G^1$;
$R^B$ is H, $C_1$-$C_4$ alkoxy, $C_1$-$C_4$ haloalkyl or $C_1$-$C_4$ alkyl;
$R^C$ is H, $C_1$-$C_4$ alkoxy, $C_1$-$C_4$ haloalkyl or $C_1$-$C_4$ alkyl;
$R^D$ is H, $C_1$-$C_3$ alkyl or $C_2$-$C_3$ alkylcarbonyl;
$R^E$ is H, hydroxy, amino, cyano, formyl, —C(O)NH$_2$, $C_1$-$C_6$ alkyl, $C_1$-$C_6$ haloalkyl, $C_2$-$C_6$ cyanoalkyl, $C_3$-$C_6$ cycloalkyl, $C_4$-$C_8$ cycloalkylalkyl, $C_2$-$C_8$ alkoxyalkyl, $C_3$-$C_8$ alkoxyalkoxyalkyl, $C_2$-$C_8$ haloalkoxyalkyl, $C_2$-$C_8$ alkenyl, $C_2$-$C_8$ haloalkenyl, $C_2$-$C_8$ alkenylalkyl, $C_2$-$C_8$ haloalkenylalkyl, $C_2$-$C_8$ alkylcarbonyl, $C_2$-$C_8$ haloalkylcarbonyl, $C_4$-$C_{10}$ cycloalkylcarbonyl, $C_5$-$C_{10}$ cycloalkylcarbonylalkyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl or $C_2$-$C_8$ dialkylaminosulfonyl;

$R^F$ is formyl, —C(O)NH$_2$, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, —P(=O)(OH)$_2$, $C_1$-$C_6$ dialkylphosphoryl, $C_1$-$C_6$ haloalkylphosphoryl, $C_3$-$C_8$ cycloalkylphosphoryl, $C_2$-$C_8$ dialkoxyphosphoryl, $C_6$-$C_{14}$ dicycloalkoxyphosphoryl, $C_8$-$C_{16}$ dicycloalkylalkoxyphosphoryl, $C_2$-$C_{12}$ bis(alkylamino)phosphoryl, $C_4$-$C_{24}$ bis(dialkylamino) phosphoryl; or phenyl substituted or unsubstituted with $R^{16}$;

$R^G$ is formyl, —C(O)NH$_2$, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl or $C_1$-$C_6$ alkylaminosulfonyl;

$Q^1$ is a phenyl ring or a naphthalenyl ring system, each ring or ring system substituted or unsubstituted with up to 5 substituents independently selected from $R^{10}$; or a 5- to 6-membered heterocyclic ring; or an 8- to 10-membered bicyclic ring system, each ring or ring system containing ring members selected from carbon atoms and 1 to 4 heteroatoms independently selected from up to 2 O, up to 2 S and up to 4 N atoms, wherein up to 2 carbon ring members are independently selected from C(=O) and C(=S), and the sulfur atom ring members are independently selected from S(=O)$_u$ (=NR$^{14}$)$_v$, each ring or ring system substituted or unsubstituted with up to 4 substituents independently selected from $R^{10}$ on carbon atom ring members and selected from $R^{12}$ on nitrogen atom ring members;

$Q^2$ is a phenyl ring, each ring substituted or unsubstituted with up to 4 substituents independently selected from $R^{11}$; or a 5- to 6-membered heterocyclic ring; or an 8- to 10-membered bicyclic ring system, each ring or ring system containing ring members selected from carbon atoms and 1 to 4 heteroatoms independently selected from up to 2 O, up to 2 S and up to 4 N atoms, wherein up to 2 carbon ring members are independently selected from C(=O) and C(=S), and the sulfur atom ring members are independently selected from S(=O)$_u$ (=NR$^{14}$)$_v$, each ring or ring system substituted or unsubstituted with up to 4 substituents independently selected from $R^{11}$ on carbon atom ring members and selected from $R^{13}$ on nitrogen atom ring members;

J is —CR$^2$R$^3$—, —CR$^2$R$^3$—CR$^4$R$^5$— or —NR$^6$—;

$Y^1$ and $Y^2$ are each independently O or S;

$R^1$ is H, CHO, $C_3$-$C_8$ alkylcarbonylalkyl, $C_1$-$C_6$ alkyl, $C_1$-$C_6$ haloalkyl, $C_2$-$C_6$ alkenyl, $C_3$-$C_6$ alkynyl, $C_2$-$C_6$ cyanoalkyl, $C_3$-$C_6$ cycloalkyl, $C_4$-$C_8$ cycloalkylalkyl, $C_2$-$C_8$ alkoxyalkyl, $C_3$-$C_8$ alkoxyalkoxyalkyl, $C_2$-$C_8$ haloalkoxyalkyl, $C_2$-$C_8$ alkylthioalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_2$-$C_8$ alkylaminocarbonyl, $C_3$-$C_{10}$ dialkylaminocarbonyl or $C_4$-$C_{10}$ cycloalkylaminocarbonyl;

$R^2$ and $R^3$ are each independently H or $C_1$-$C_4$ alkyl;

$R^4$ and $R^5$ are each independently H, halogen, $C_1$-$C_4$ alkyl or $C_1$-$C_4$ alkoxy;

$R^6$ is H, $C_1$-$C_6$ alkyl or $C_1$-$C_6$ alkoxy;

$R^7$ is H, halogen, $C_1$-$C_4$ alkoxy or $C_1$-$C_4$ alkyl;

each $R^8$ is independently cyano, nitro, —CHO, $C_2$-$C_6$ alkenyl, $C_2$-$C_6$ alkynyl, $C_2$-$C_8$ alkylcarbonyl, $C_2$-$C_8$ haloalkylcarbonyl, $C_2$-$C_8$ alkoxycarbonyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_1$-$C_6$ alkoxy, $C_1$-$C_6$ haloalkoxy or $C_2$-$C_8$ alkylcarbonyloxy;

$R^9$ is H, $C_1$-$C_6$ alkyl, $C_2$-$C_8$ alkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_4$-$C_{10}$ cycloalkylcarbonyl, $C_2$-$C_8$ alkoxycarbonyl or $C_4$-$C_{10}$ cycloalkoxycarbonyl;

each $R^{10}$ and $R^{11}$ is halogen, nitro, $C_1$-$C_8$ alkyl, $C_1$-$C_8$ cyanoalkyl, $C_1$-$C_8$ cyanoalkoxy, $C_1$-$C_8$ haloalkyl, $C_1$-$C_8$ nitroalkyl, $C_2$-$C_8$ alkenyl, $C_2$-$C_8$ haloalkenyl, $C_2$-$C_8$ nitroalkenyl, $C_2$-$C_8$ alkoxyalkyl, $C_3$-$C_8$ alkoxyalkylalkyl, $C_2$-$C_8$ haloalkoxyalkyl, $C_2$-$C_8$ haloalkoxyhaloalkoxy, $C_4$-$C_{10}$ cycloalkylalkyl, $C_4$-$C_{10}$ halocycloalkylalkyl, $C_5$-$C_{12}$ alkylcycloalkylalkyl, $C_5$-$C_{12}$ cycloalkylalkenyl, $C_3$-$C_8$ cycloalkyl, $C_3$-$C_8$ halocycloalkyl, $C_4$-$C_{10}$ alkylcycloalkyl, $C_6$-$C_{12}$ cycloalkylcycloalkyl, $C_3$-$C_8$ cycloalkenyl, $C_3$-$C_8$ halocycloalkenyl, $C_2$-$C_8$ haloalkoxyalkoxy, $C_2$-$C_8$ alkoxyalkoxy, $C_4$-$C_{10}$ cycloalkoxyalkyl, $C_2$-$C_8$ alkylcarbonyl, $C_2$-$C_8$ haloalkylcarbonyl, $C_4$-$C_{10}$ cycloalkylcarbonyl, —C(=O)OH, $C_2$-$C_8$ alkoxycarbonyl, $C_2$-$C_8$ haloalkoxycarbonyl, $C_4$-$C_{10}$ cycloalkoxycarbonyl, $C_5$-$C_{12}$ cycloalkylalkoxycarbonyl, —C(=O)NH$_2$, $C_1$-$C_8$ alkoxy, $C_1$-$C_8$ haloalkoxy, $C_2$-$C_8$ alkenyloxy, $C_2$-$C_8$ haloalkenyloxy, $C_3$-$C_8$ cycloalkoxy, $C_3$-$C_8$ halocycloalkoxy, $C_4$-$C_{10}$ cycloalkylalkoxy, $C_3$-$C_{10}$ alkylcarbonylalkoxy, $C_2$-$C_8$ alkylcarbonyloxy, $C_2$-$C_8$ haloalkylcarbonyloxy, $C_4$-$C_{10}$ cycloalkylcarbonyloxy, $C_1$-$C_8$ alkylsulfonyloxy, $C_1$-$C_8$ haloalkylsulfonyloxy, $C_1$-$C_8$ alkylsulfonyl, $C_1$-$C_8$ haloalkylsulfonyl, $C_3$-$C_8$ cycloalkylsulfonyl;

each $G^1$ is independently phenyl; or a 6-membered heterocyclic ring, each substituted or unsubstituted on ring members with up to 4 substituents independently selected from $R^{17}$;

each $R^{16}$ and $R^{17}$ is independently halogen, cyano, hydroxy, amino, nitro, —CHO, —C(=O)OH, —C(=O)NH$_2$, —SO$_2$NH$_2$, $C_1$-$C_6$ alkyl, $C_1$-$C_6$ haloalkyl, $C_2$-$C_6$ alkenyl, $C_2$-$C_6$ alkynyl, $C_2$-$C_8$ alkylcarbonyl, $C_1$-$C_8$ hydroxyalkyl, $C_2$-$C_8$ haloalkylcarbonyl, $C_2$-$C_6$ alkoxyalkyl, $C_2$-$C_6$ alkylaminoalkyl, $C_2$-$C_8$ alkoxycarbonyl, $C_3$-$C_8$ cycloalkyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_3$-$C_8$ dialkylaminoalkyl, $C_1$-$C_6$ alkoxy, $C_1$-$C_6$ haloalkoxy, $C_2$-$C_8$ alkylcarbonyloxy or $C_1$-$C_6$ alkylthio; and provided the sum of u and v is 2.

Embodiment B. A compound of Embodiment A wherein L is selected from L-1, L-2 or L-3;

$R^A$ is $C_1$-$C_7$ alkyl, $C_1$-$C_7$ haloalkyl, $C_1$-$C_7$ alkoxy or $C_1$-$C_7$ haloalkoxy; each substituted or unsubstituted with up to 2 substituents independently selected from $R^8$; or $R^A$ is $G^1$;

$R^B$ is H, —OCH$_3$, CF$_3$ or CH$_3$;

$R^C$ is H, $C_1$-$C_2$ alkoxy or $C_1$-$C_2$ alkyl;

$R^D$ is H, $CH_3$, $CH_2CH_3$ or —C(=O)$CH_3$ $CH_2CH_3$;

$R^E$ is H, hydroxy, amino, cyano, formyl, —C(O)$NH_2$, $C_1$-$C_6$ alkyl, $C_3$-$C_6$ cycloalkyl, $C_4$-$C_8$ cycloalkylalkyl, $C_2$-$C_8$ alkoxyalkyl, $C_3$-$C_8$ alkoxyalkoxyalkyl, $C_2$-$C_8$ alkylcarbonyl, $C_4$-$C_{10}$ cycloalkylcarbonyl, $C_5$-$C_{10}$ cycloalkylcarbonylalkyl, $C_2$-$C_8$ alkoxycarbonyl, $C_4$-$C_{10}$ cycloalkoxycarbonyl, $C_1$-$C_6$ alkylsulfonyl;

$R^F$ is $C_2$-$C_8$ alkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkylsulfonyl, $C_1$-$C_6$ haloalkylsulfonyl, $C_3$-$C_8$ cycloalkylsulfonyl or $C_1$-$C_6$ alkylaminosulfonyl; or phenyl substituted or unsubstituted with $R^{16}$;

$R^G$ is formyl, $C_2$-$C_8$ alkylcarbonyl, $C_2$-$C_8$ alkoxycarbonyl, $C_4$-$C_{10}$ cycloalkoxycarbonyl, $C_2$-$C_8$ alkylaminocarbonyl, $C_4$-$C_{10}$ cycloalkylaminocarbonyl, $C_1$-$C_6$ alkylsulfonyl, $C_1$-$C_6$ haloalkylsulfonyl, $C_3$-$C_8$ cycloalkylsulfonyl or $C_1$-$C_6$ alkylaminosulfonyl;

each $R^8$ is independently $C_2$-$C_6$ alkenyl, $C_1$-$C_6$ alkoxy or $C_1$-$C_6$ haloalkoxy;

J is —$CR^2R^3$— or —$CR^2R^3$—$CR^4R^5$—;

$Y^1$ and $Y^2$ are each independently O;

$R^1$ is H, $C_3$-$C_8$ alkylcarbonylalkyl, $C_1$-$C_6$ alkyl, $C_1$-$C_6$ haloalkyl, $C_2$-$C_6$ cyanoalkyl, $C_3$-$C_6$ cycloalkyl, $C_4$-$C_8$ cycloalkylalkyl, $C_2$-$C_8$ alkoxyalkyl, $C_2$-$C_8$ haloalkoxyalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl or $C_2$-$C_8$ haloalkoxycarbonyl;

$Q^1$ is a phenyl ring substituted or unsubstituted with up to 4 substituents independently selected from $R^{10}$; or a 5- to 6-membered heterocyclic ring, each ring containing ring members selected from carbon atoms and 1 to 4 heteroatoms independently selected from up to 2 O, up to 2 S and up to 4 N atoms, each ring substituted or unsubstituted with up to 4 substituents independently selected from $R^{10}$ on carbon atom ring members and selected from $R^{12}$ on nitrogen atom ring members;

$Q^2$ is a phenyl ring, substituted or unsubstituted with up to 4 substituents independently selected from $R^{11}$; or a 5- to 6-membered heterocyclic ring; or an 8- to 10-membered bicyclic ring system, each ring or ring system containing ring members selected from carbon atoms and 1 to 4 heteroatoms independently selected from up to 2 O, up to 2 S and up to 4 N atoms, wherein up to 2 carbon ring members are independently selected from C(=O) and C(=S), and the sulfur atom ring members are independently selected from S(=O)$_u$(=$NR^{14}$)$_v$, each ring or ring system substituted or unsubstituted with up to 4 substituents independently selected from $R^{11}$ on carbon atom ring members and selected from $R^{13}$ on nitrogen atom ring members;

$R^2$ and $R^3$ are each independently H or $CH_3$;

$R^4$ and $R^5$ are each independently H, halogen or $C_1$-$C_4$ alkyl;

$R^7$ is H, F, Cl or $CH_3$;

$R^9$ is H, $C_1$-$C_6$ alkyl, $C_2$-$C_8$ alkoxyalkyl, $C_2$-$C_8$ alkylcarbonyl or $C_2$-$C_8$ alkoxycarbonyl;

each $R^{10}$ and $R^{11}$ is independently halogen, $C_1$-$C_8$ alkyl, $C_1$-$C_8$ haloalkyl, $C_2$-$C_8$ alkoxyalkyl, $C_3$-$C_8$ alkoxyalkoxyalkyl, $C_4$-$C_{10}$ cycloalkylalkyl, $C_5$-$C_{12}$ alkylcycloalkylalkyl, $C_3$-$C_8$ cycloalkyl, $C_3$-$C_8$ halocycloalkyl, $C_6$-$C_{12}$ cycloalkylcycloalkyl, $C_3$-$C_8$ halocycloalkenyl, $C_2$-$C_8$ haloalkoxyalkoxy, $C_2$-$C_8$ alkoxyalkoxy, $C_4$-$C_{10}$ cycloalkoxyalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_4$-$C_{10}$ cycloalkoxycarbonyl, $C_5$-$C_{12}$ cycloalkylalkoxycarbonyl, $C_1$-$C_8$ alkoxy, $C_1$-$C_8$ haloalkoxy, $C_2$-$C_8$ haloalkenyloxy, $C_3$-$C_8$ cycloalkoxy, $C_3$-$C_8$ halocycloalkoxy, $C_4$-$C_{10}$ cycloalkylalkoxy, $C_3$-$C_{10}$ alkylcarbonylalkoxy or $C_2$-$C_8$ haloalkylcarbonyloxy;

each $R^{12}$ and $R^{13}$ is independently $C_1$-$C_3$ alkyl, $C_3$-$C_6$ cycloalkyl or $C_2$-$C_3$ alkylcarbonyl;

each $R^{14}$ is independently H;

$R^{15}$ is H, $CH_3$, —(C=O)$CH_3$ or —(C=O)$CF_3$;

each $G^1$ is independently phenyl substituted or unsubstituted on ring members with up to 3 substituents independently selected from $R^{17}$; and each $R^{16}$ and $R^{17}$ is independently halogen, cyano, hydroxy, amino, nitro, —CHO, —C(=O)OH, —C(=O)$NH_2$, —$SO_2NH_2$, $C_1$-$C_6$ alkyl or $C_1$-$C_6$ haloalkyl.

Embodiment C. A compound of Embodiment B wherein

L is selected from L-1 or L-2;

$R^A$ is $C_1$-$C_7$ alkyl or $C_1$-$C_7$ alkoxy; each substituted or unsubstituted with up to 2 substituents independently selected from $R^8$;

$R^B$ is H, —$OCH_3$ or $CH_3$;

$R^C$ is H or $CH_3$;

$R^D$ is $CH_3$ or $CH_2CH_3$;

$R^E$ is H, $C_1$-$C_6$ alkyl, $C_3$-$C_6$ cycloalkyl, $C_4$-$C_8$ cycloalkylalkyl, $C_2$-$C_8$ alkoxyalkyl, $C_2$-$C_8$ alkylcarbonyl, $C_2$-$C_8$ alkoxycarbonyl, $C_4$-$C_{10}$ cycloalkoxycarbonyl, $C_1$-$C_6$ alkylsulfonyl;

each $R^8$ is independently $C_1$-$C_6$ alkoxy or $C_1$-$C_6$ haloalkoxy;

J is —$CR^2R^3$—;

$Y^1$ and $Y^2$ are each independently O;

$R^1$ is H, $C_1$-$C_6$ alkyl, $C_1$-$C_6$ haloalkyl, $C_2$-$C_6$ cyanoalkyl, $C_3$-$C_6$ cycloalkyl, $C_4$-$C_8$ cycloalkylalkyl, $C_2$-$C_8$ alkoxyalkyl, $C_2$-$C_8$ haloalkoxyalkyl or $C_2$-$C_8$ alkoxycarbonyl;

$Q^1$ is a phenyl ring substituted or unsubstituted with up to 4 substituents independently selected from $R^{10}$;

$Q^2$ is a phenyl ring, substituted or unsubstituted with up to 4 substituents independently selected from $R^{11}$; or a 5- to 6-membered heterocyclic ring containing ring members selected from carbon atoms and 1 to 4 heteroatoms independently selected from up to 4 N atoms, wherein up to 2 carbon ring members are independently selected from C(=O) and C(=S), each ring or ring system substituted or unsubstituted with up to 4 substituents independently selected from $R^{11}$ on carbon atom ring members and selected from $R^{13}$ on nitrogen atom ring members;

$R^2$ and $R^3$ are each independently H;

$R^7$ is H or $CH_3$;

$R^9$ is H, $C_1$-$C_6$ alkyl or $C_2$-$C_8$ alkoxycarbonyl;

each $R^{10}$ and $R^{11}$ is independently halogen, $C_1$-$C_8$ alkyl, $C_1$-$C_8$ haloalkyl, $C_2$-$C_8$ alkoxyalkyl, $C_4$-$C_{10}$ cycloalkylalkyl, $C_5$-$C_{12}$ alkylcycloalkylalkyl, $C_3$-$C_8$ cycloalkyl, $C_3$-$C_8$ halocycloalkyl, $C_2$-$C_8$ haloalkoxyalkoxy, $C_1$-$C_8$ alkoxy, $C_1$-$C_8$ haloalkoxy or $C_2$-$C_8$ alkoxyalkoxy; and each $R^{12}$ and $R^{13}$ is independently $C_1$-$C_3$ alkyl or $C_2$-$C_3$ alkylcarbonyl.

Embodiment D. A compound of Embodiment C wherein

L is selected from L-1;

$R^A$ is $C_1$-$C_3$ alkyl substituted or unsubstituted with up to 2 substituents independently selected from $R^8$;

each $R^8$ is independently $C_1$-$C_6$ alkoxy;

$R^1$ is H, $C_1$-$C_6$ alkyl, $C_3$-$C_6$ cycloalkyl, $C_4$-$C_8$ cycloalkylalkyl or $C_2$-$C_8$ alkoxyalkyl;

Q¹ is a phenyl ring substituted or unsubstituted with up to 3 substituents independently selected from R¹⁰;

Q² is a phenyl ring, substituted or unsubstituted with up to 4 substituents independently selected from R¹¹;

$R^7$ is H;

$R^9$ is H, $CH_3$ or —C(=O)$CH_3$; and each $R^{10}$ and $R^{11}$ is independently halogen, $C_1$-$C_8$ alkyl, $C_1$-$C_8$ haloalkyl, $C_3$-$C_8$ cycloalkyl, $C_1$-$C_8$ alkoxy or $C_1$-$C_8$ haloalkoxy.

Embodiment E. A compound of Embodiment C wherein
L is selected from L-1;
$R^4$ is $C_1$-$C_3$ alkoxy, substituted or unsubstituted with up to 2 substituents independently selected from $R^8$;
each $R^8$ is independently $C_1$-$C_6$ alkoxy;
$R^1$ is H, $CH_3$, $CH_2CH_3$, cyclopropyl, cyclopropylmethyl or $CH_2OCH_3$;
Q¹ is a phenyl ring substituted or unsubstituted with up to 2 substituents independently selected from $R^{10}$;
Q² is a phenyl ring, substituted or unsubstituted with up to 3 substituents independently selected from $R^{11}$;
$R^7$ is H;
$R^9$ is H; and
each $R^{10}$ and $R^{11}$ is independently halogen, $C_1$-$C_8$ alkyl, $C_1$-$C_8$ haloalkyl, $C_1$-$C_8$ alkoxy or $C_1$-$C_8$ haloalkoxy.

Specific Embodiments of the Invention include a compound of the Summary of the Invention selected from:

(3S,4R)—N-(2,3-difluorophenyl)-3-(hydroxymethyl)-1-methyl-2-oxo-4-[4-(trifluoromethyl)-3-pyrrolidinecarboxamide (cis);

(3R,4S)—N-(2,3-difluorophenyl)-3-(hydroxymethyl)-1-methyl-2-oxo-4-[4-(trifluoromethyl)-3-pyrrolidinecarboxamide (trans);

(3S,4R)-3-[(acetyloxy)methyl]-N-(2,3-difluorophenyl)-1-methyl-2-oxo-4-[4-(trifluoromethyl)-3-pyrrolidinenecarboxamide; and (3S,4R)-3-acetyl-N-(2,3-difluorophenyl)-1-methyl-2-oxo-4-[4-(trifluoromethyl)-3-pyrrolidinecarboxamide.

This invention also relates to a method for controlling undesired vegetation comprising applying to the locus of the vegetation herbicidally effective amounts of the compounds of the invention (e.g., as a composition described herein). Of note as embodiments relating to methods of use are those involving the compounds of embodiments described above. Compounds of the invention are particularly useful for selective control of weeds in crops such as wheat, barley, maize, soybean, sunflower, cotton, oilseed rape and rice, and specialty crops such as sugarcane, citrus, fruit and nut crops.

Also noteworthy as embodiments are herbicidal compositions of the present invention comprising the compounds of embodiments described above.

This invention also includes a herbicidal mixture comprising (a) a compound selected from Formula 1, N-oxides, and salts thereof, and (b) at least one additional active ingredient selected from (b1) photosystem II inhibitors, (b2) acetohydroxy acid synthase (AHAS) inhibitors, (b3) acetyl-CoA carboxylase (ACCase) inhibitors, (b4) auxin mimics, (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solenesyltransererase (HST) inhibitors, (b14) cellulose biosynthesis inhibitors, (b15) other herbicides including mitotic disruptors, organic arsenicals, asulam, bromobutide, cinmethylin, cumyluron, dazomet, 2-[(2,5-dichlorophenyl)methyl]-4,4-dimethyl-3-isoxazolidinone, difenzoquat, dymron, etobenzanid, flurenol, fosamine, fosamine-ammonium, hydantocidin, metam, methyldymron, oleic acid, oxaziclomefone, pelargonic acid and pyributicarb, and (b16) herbicide safeners; and salts of compounds of (b1) through (b16).

"Photosystem II inhibitors" (b1) are chemical compounds that bind to the D-1 protein at the $Q_B$-binding niche and thus block electron transport from $Q_A$ to $Q_B$ in the chloroplast thylakoid membranes. The electrons blocked from passing through photosystem II are transferred through a series of reactions to form toxic compounds that disrupt cell membranes and cause chloroplast swelling, membrane leakage, and ultimately cellular destruction. The $Q_B$-binding niche has three different binding sites: binding site A binds the triazines such as atrazine, triazinones such as hexazinone, and uracils such as bromacil, binding site B binds the phenylureas such as diuron, and binding site C binds benzothiadiazoles such as bentazon, nitriles such as bromoxynil and phenyl-pyridazines such as pyridate. Examples of photosystem II inhibitors include ametryn, amicarbazone, atrazine, bentazon, bromacil, bromofenoxim, bromoxynil, chlorbromuron, chloridazon, chlorotoluron, chloroxuron, cumyluron, cyanazine, daimuron, desmedipham, desmetryn, dimefuron, dimethametryn, diuron, ethidimuron, fenuron, fluometuron, hexazinone, ioxynil, isoproturon, isouron, lenacil, linuron, metamitron, methabenzthiazuron, metobromuron, metoxuron, metribuzin, monolinuron, neburon, pentanochlor, phenmedipham, prometon, prometryn, propanil, propazine, pyridafol, pyridate, siduron, simazine, simetryn, tebuthiuron, terbacil, terbumeton, terbuthylazine, terbutryn and trietazine.

"AHAS inhibitors" (b2) are chemical compounds that inhibit acetohydroxy acid synthase (AHAS), also known as acetolactate synthase (ALS), and thus kill plants by inhibiting the production of the branched-chain aliphatic amino acids such as valine, leucine and isoleucine, which are required for protein synthesis and cell growth. Examples of AHAS inhibitors include amidosulfuron, azimsulfuron, bensulfuron-methyl, bispyribac-sodium, cloransulam-methyl, chlorimuron-ethyl, chlorsulfuron, cinosulfuron, cyclosulfamuron, diclosulam, ethametsulfuron-methyl, ethoxysulfuron, flazasulfuron, florasulam, flucarbazone-sodium, flumetsulam, flupyrsulfuron-methyl, flupyrsulfuron-sodium, foramsulfuron, halosulfuron-methyl, imazamethabenzmethyl, imazamox, imazapic, imazapyr, imazaquin, imazethapyr, imazosulfuron, iodosulfuron-methyl (including sodium salt), iofensulfuron (2-iodo-N-[[(4-methoxy-6-methyl-1,3,5-triazin-2-yl)amino]carbonyl]benzenesulfonamide), mesosulfuron-methyl, metazosulfuron (3-chloro-4-(5,6-dihydro-5-methyl-1,4,2-dioxazin-3-yl)-N-[[(4,6-dimethoxy-2-pyrimidinyl)amino]carbonyl]-1-methyl-1H-pyrazole-5-sulfonamide), metosulam, metsulfuron-methyl, nicosulfuron, oxasulfuron, penoxsulam, primisulfuron-methyl, propoxycarbazone-sodium, propyrisulfuron (2-chloro-N-[[(4,6-dimethoxy-2-pyrimidinyl)amino]carbonyl]-6-propylimidazo[1,2-b]pyridazine-3-sulfonamide), prosulfuron, pyrazosulfuron-ethyl, pyribenzoxim, pyriftalid, pyriminobac-methyl, pyrithiobac-sodium, rimsulfuron, sulfometuron-methyl, sulfosulfuron, thiencarbazone, thifensulfuron-methyl, triafamone (N-[2-[(4,6-dimethoxy-1,3,5-triazin-2-yl)carbonyl]-6-fluorophenyl]-1,1-difluoro-N-methylmethanesulfonamide), triasulfuron, tribenuron-methyl, trifloxysulfuron (including sodium salt), triflusulfuron-methyl and tritosulfuron.

"ACCase inhibitors" (b3) are chemical compounds that inhibit the acetyl-CoA carboxylase enzyme, which is responsible for catalyzing an early step in lipid and fatty acid synthesis in plants. Lipids are essential components of cell membranes, and without them, new cells cannot be produced. The inhibition of acetyl CoA carboxylase and the subsequent lack of lipid production leads to losses in cell membrane integrity, especially in regions of active growth such as meristems. Eventually shoot and rhizome growth ceases, and shoot meristems and rhizome buds begin to die back. Examples of ACCase inhibitors include alloxydim, butroxydim, clethodim, clodinafop, cycloxydim, cyhalofop, diclofop, fenoxaprop, fluazifop, haloxyfop, pinoxaden, profoxydim, propaquizafop, quizalofop, sethoxydim, tepraloxydim and tralkoxydim, including resolved forms such as fenoxaprop-P, fluazifop-P, haloxyfop-P and quizalofop-P and ester forms such as clodinafop-propargyl, cyhalofop-butyl, diclofop-methyl and fenoxaprop-P-ethyl.

Auxin is a plant hormone that regulates growth in many plant tissues. "Auxin mimics" (b4) are chemical compounds mimicking the plant growth hormone auxin, thus causing uncontrolled and disorganized growth leading to plant death in susceptible species. Examples of auxin mimics include aminocyclopyrachlor (6-amino-5-chloro-2-cyclopropyl-4-pyrimidinecarboxylic acid) and its methyl and ethyl esters and its sodium and potassium salts, aminopyralid, benazolin-ethyl, chloramben, clacyfos, clomeprop, clopyralid, dicamba, 2,4-D, 2,4-DB, dichlorprop, fluroxypyr, halauxifen (4-amino-3-chloro-6-(4-chloro-2-fluoro-3-methoxyphenyl)-2-pyridinecarboxylic acid), halauxifen-methyl (methyl 4-amino-3-chloro-6-(4-chloro-2-fluoro-3-methoxyphenyl)-2-pyridinecarboxylate), MCPA, MCPB, mecoprop, picloram, quinclorac, quinmerac, 2,3,6-TBA, triclopyr, and methyl 4-amino-3-chloro-6-(4-chloro-2-fluoro-3-methoxyphenyl)-5-fluoro-2-pyridinecarboxylate.

"EPSP synthase inhibitors" (b5) are chemical compounds that inhibit the enzyme, 5-enol-pyruvylshikimate-3-phosphate synthase, which is involved in the synthesis of aromatic amino acids such as tyrosine, tryptophan and phenylalanine. EPSP inhibitor herbicides are readily absorbed through plant foliage and translocated in the phloem to the growing points. Glyphosate is a relatively nonselective postemergence herbicide that belongs to this group. Glyphosate includes esters and salts such as ammonium, isopropylammonium, potassium, sodium (including sesquisodium) and trimesium (alternatively named sulfosate)).

"Photosystem I electron diverters" (b6) are chemical compounds that accept electrons from Photosystem I, and after several cycles, generate hydroxyl radicals. These radicals are extremely reactive and readily destroy unsaturated lipids, including membrane fatty acids and chlorophyll. This destroys cell membrane integrity, so that cells and organelles "leak", leading to rapid leaf wilting and desiccation, and eventually to plant death. Examples of this second type of photosynthesis inhibitor include diquat and paraquat.

"PPO inhibitors" (b7) are chemical compounds that inhibit the enzyme protoporphyrinogen oxidase, quickly resulting in formation of highly reactive compounds in plants that rupture cell membranes, causing cell fluids to leak out. Examples of PPO inhibitors include acifluorfen-sodium, azafenidin, benzfendizone, bifenox, butafenacil, carfentrazone, carfentrazone-ethyl, chlomethoxyfen, cinidon-ethyl, cyclopyranil, fluazolate, flufenpyr-ethyl, flumiclorac-pentyl, flumioxazin, fluoroglycofen-ethyl, fluthiacet-methyl, fomesafen, halosafen, lactofen, oxadiargyl, oxadiazon, oxyfluorfen, pentoxazone, profluazol, pyraclonil, pyraflufen-ethyl, saflufenacil, sulfentrazone, thidiazimin, trifludimoxazin (dihydro-1,5-dimehyl-6-thioxo-3-[2,2,7-trifluoro-3,4-dihydro-3-oxo-4-(2-propyn-1-yl)-2H-1,4-benzoxazin-6-yl]-1,3,5-triazine-2,4(1H,3H)-dione) and tiafenacil (methyl N-[2-[[2-chloro-5-[3,6-dihydro-3-methyl-2,6-dioxo-4-(trifluoromethyl)-1(2H)-pyrimidinyl]-4-fluorophenyl]thio]-1-oxopropyl]-β-alaninate).

"GS inhibitors" (b8) are chemical compounds that inhibit the activity of the glutamine synthetase enzyme, which plants use to convert ammonia into glutamine. Consequently, ammonia accumulates and glutamine levels decrease. Plant damage probably occurs due to the combined effects of ammonia toxicity and deficiency of amino acids required for other metabolic processes. The GS inhibitors include glufosinate and its esters and salts such as glufosinate-ammonium and other phosphinothricin derivatives, glufosinate-P ((2S)-2-amino-4-(hydroxymethylphosphinyl)butanoic acid) and bilanaphos.

"VLCFA elongase inhibitors" (b9) are herbicides having a wide variety of chemical structures, which inhibit the elongase. Elongase is one of the enzymes located in or near chloroplasts which are involved in biosynthesis of VLCFAs. In plants, very-long-chain fatty acids are the main constituents of hydrophobic polymers that prevent desiccation at the leaf surface and provide stability to pollen grains. Such herbicides include acetochlor, alachlor, anilofos, butachlor, cafenstrole, dimethachlor, dimethenamid, diphenamid, fenoxasulfone (3-[[(2,5-dichloro-4-ethoxyphenyl)methyl]sulfonyl]-4,5-dihydro-5,5-dimethylisoxazole), fentrazamide, flufenacet, indanofan, mefenacet, metazachlor, metolachlor, naproanilide, napropamide, napropamide-M ((2R)—N,N-diethyl-2-(1-naphthalenyloxy)propanamide), pethoxamid, piperophos, pretilachlor, propachlor, propisochlor, pyroxasulfone, and thenylchlor, including resolved forms such as S-metolachlor and chloroacetamides and oxyacetamides.

"Auxin transport inhibitors" (b10) are chemical substances that inhibit auxin transport in plants, such as by binding with an auxin-carrier protein. Examples of auxin transport inhibitors include diflufenzopyr, naptalam (also known as N-(1-naphthyl)phthalamic acid and 2-[(1-naphthalenylamino)carbonyl]benzoic acid).

"PDS inhibitors" (b11) are chemical compounds that inhibit carotenoid biosynthesis pathway at the phytoene desaturase step. Examples of PDS inhibitors include beflubutamid, S-beflubutamid, diflufenican, fluridone, fluorochloridone, flurtamone norflurzon and picolinafen.

"HPPD inhibitors" (b12) are chemical substances that inhibit the biosynthesis of synthesis of 4-hydroxyphenylpyruvate dioxygenase. Examples of HPPD inhibitors include benzobicyclon, benzofenap, bicyclopyrone (4-hydroxy-3-[[2-[(2-methoxyethoxy)methyl]-6-(trifluoromethyl)-3-pyridinyl]carbonyl]bicyclo[3.2.1]oct-3-en-2-one), fenquinotrione (2-[[8-chloro-3,4-dihydro-4-(4-methoxyphenyl)-3-oxo-2-quinoxalinyl]carbonyl]-1,3-cyclohexanedione), isoxachlortole, isoxaflutole, mesotrione, pyrasulfotole, pyrazolynate, pyrazoxyfen, sulcotrione, tefuryltrione, tembotrione, tolpyralate (1-[[1-ethyl-4-[3-(2-methoxyethoxy)-2-methyl-4-(methylsulfonyl)benzoyl]-1H-pyrazol-5-yl]oxy]ethyl methyl carbonate), topramezone, 5-chloro-3-[(2-hydroxy-6-oxo-1-cyclohexen-1-yl)carbonyl]-1-(4-methoxyphenyl)-2(1H)-quinoxalinone, 4-(2,6-diethyl-4-methylphenyl)-5-hydroxy-2,6-dimethyl-3(2H)-pyridazinone, 4-(4-fluorophenyl)-6-[(2-hydroxy-6-oxo-1-cyclohexen-1-yl)carbonyl]-2-methyl-1,2,4-triazine-3,5(2H, 4H)-dione, 5-[(2-hydroxy-6-oxo-1-cyclohexen-1-yl)carbonyl]-2-(3-methoxyphenyl)-3-(3-methoxypropyl)-4(3H)-pyrimidinone, 2-methyl-N-(4-methyl-1,2,5-oxadiazol-3-yl)-3-(methylsulfinyl)-4-(trifluoromethyl)benzamide and 2-methyl-3-(methylsulfonyl)-N-(1-methyl-1H-tetrazol-5-yl)-4-(trifluoromethyl)benzamide.

"HST inhibitors" (b13) disrupt a plant's ability to convert homogentisate to 2-methyl-6-solanyl-1,4-benzoquinone, thereby disrupting carotenoid biosynthesis. Examples of HST inhibitors include haloxydine, pyriclor, 3-(2-chloro-3,6-difluorophenyl)-4-hydroxy-1-methyl-1,5-naphthyridin-2(1H)-one, 7-(3,5-dichloro-4-pyridinyl)-5-(2,2-difluoroethyl)-8-hydroxypyrido[2,3-b]pyrazin-6(5H)-one and 4-(2,6-diethyl-4-methylphenyl)-5-hydroxy-2,6-dimethyl-3(2H)-pyridazinone.

HST inhibitors also include compounds of Formulae A and B.

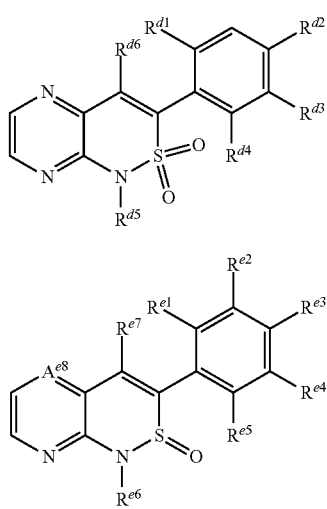

wherein $R^{d1}$ is H, Cl or $CF_3$; $R^{d2}$ is H, Cl or Br; $R^{d3}$ is H or Cl; $R^{d4}$ is H, Cl or $CF_3$; $R^{d5}$ is $CH_3$, $CH_2CH_3$ or $CH_2CHF_2$; and $R^{d6}$ is OH, or $-OC(=O)$-i-Pr; and $R^{e1}$ is H, F, Cl, $CH_3$ or $CH_2CH_3$; $R^{e2}$ is H or $CF_3$; $R^{e3}$ is H, $CH_3$ or $CH_2CH_3$; $R^{e4}$ is H, F or Br; $R^{e5}$ is Cl, $CH_3$, $CF_3$, $OCF_3$ or $CH_2CH_3$; $R^{e6}$ is H, $CH_3$, $CH_2CHF_2$ or $C\equiv CH$; $R^{e7}$ is OH, $-OC(=O)Et$, $-OC(=O)$-i-Pr or $-OC(=O)$-t-Bu; and $A^{e8}$ is N or CH.

"Cellulose biosynthesis inhibitors" (b14) inhibit the biosynthesis of cellulose in certain plants. They are most effective when applied preemergence or early postemergence on young or rapidly growing plants. Examples of cellulose biosynthesis inhibitors include chlorthiamid, dichlobenil, flupoxam, indaziflam ($N^2$-[(1R,2S)-2,3-dihydro-2,6-dimethyl-1H-inden-1-yl]-6-(1-fluoroethyl)-1,3,5-triazine-2,4-diamine), isoxaben and triaziflam.

"Other herbicides" (b15) include herbicides that act through a variety of different modes of action such as mitotic disruptors (e.g., flamprop-M-methyl and flamprop-M-isopropyl), organic arsenicals (e.g., DSMA, and MSMA), 7,8-dihydropteroate synthase inhibitors, chloroplast isoprenoid synthesis inhibitors and cell-wall biosynthesis inhibitors. Other herbicides include those herbicides having unknown modes of action or do not fall into a specific category listed in (b1) through (b14) or act through a combination of modes of action listed above. Examples of other herbicides include aclonifen, asulam, amitrole, bromobutide, cinmethylin, clomazone, cumyluron, cyclopyrimorate (6-chloro-3-(2-cyclopropyl-6-methylphenoxy)-4-pyridazinyl 4-morpholinecarboxylate), daimuron, 2-[(2,5-dichlorophenyl)methyl]-4,4-dimethyl-3-isoxazolidinone, difenzoquat, etobenzanid, fluometuron, flurenol, fosamine, fosamine-ammonium, dazomet, dymron, ipfencarbazone (1-(2,4-dichlorophenyl)-N-(2,4-difluorophenyl)-1,5-dihydro-N-(1-methylethyl)-5-oxo-4H-1,2,4-triazole-4-carboxamide), metam, methyldymron, oleic acid, oxaziclomefone, pelargonic acid, pyributicarb and 5-[[(2,6-difluorophenyl)methoxy]methyl]-4,5-dihydro-5-methyl-3-(3-methyl-2-thienyl)isoxazole.

"Other herbicides" (b15) also include a compound of Formula (b15A),

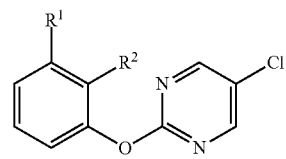

wherein $R^1$ is Cl, Br or CN; and $R^2$ is $C(=O)$ $CH_2CH_2CF_3$, $CH_2CH_2CH_2CH_2CF_3$ or 3-$CHF_2$-isoxazol-5-yl. "Other herbicides" (b15) also include a compound of Formula (b15B)

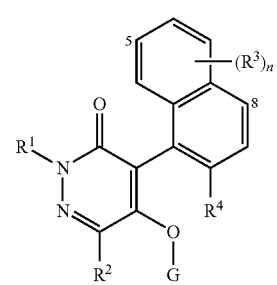

wherein $R^1$ is $CH_3$, $R^2$ is Me, $R^4$ is $OCHF_2$, G is H, and n is 0; $R^1$ is $CH_3$, $R^2$ is Me, $R^3$ is 5-F, $R^4$ is Cl, G is H, and n is 1; $R^1$ is $CH_3$, $R^2$ is Cl, $R^4$ is Me, G is H, and n is 0; $R^1$ is $CH_3$, $R^2$ is Me, $R^4$ is Cl, G is H, and n is 0; $R^1$ is $CH_3$, $R^2$ is Me, $R^3$ is 5-Me, $R^4$ is $OCHF_2$, G is H, and n is 1; $R^1$ is $CH_3$, $R^2$ is Me, $R^3$ is 5-Br, $R^4$ is $OCHF_2$, G is H, and n is 1; $R^1$ is $CH_3$, $R^2$ is Me, $R^3$ is 5-Cl, $R^4$ is Cl, G is H, and n is 1; or $R^1$ is $CH_3$, $R^2$ is $CH_3$, $R^4$ is $OCHF_2$, G is C(O)Me, and n is 0.

"Other herbicides" (b15) also include a compound of Formula (b15C)

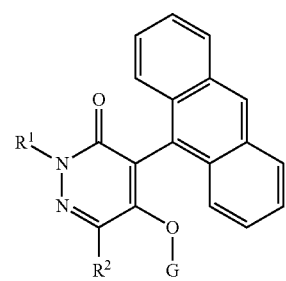

wherein
$R^1$ is $CH_3$, $R^2$ is Cl, and G is H; or
$R^1$ is $CH_3$, $R^2$ is Cl, and G is C(O)Me.

"Herbicide safeners" (b16) are substances added to a herbicide formulation to eliminate or reduce phytotoxic effects of the herbicide to certain crops. These compounds protect crops from injury by herbicides but typically do not prevent the herbicide from controlling undesired vegetation. Examples of herbicide safeners include but are not limited to benoxacor, cloquintocet-mexyl, cumyluron, cyometrinil, cyprosulfamide, daimuron, dichlormid, dicyclonon, dietholate, dimepiperate, fenchlorazole-ethyl, fenclorim, flurazole, fluxofenim, furilazole, isoxadifen-ethyl, mefenpyr-diethyl, mephenate, methoxyphenone, naphthalic anhydride, oxabetrinil, N-(aminocarbonyl)-2-methylbenzenesulfonamide and N-(aminocarbonyl)-2-fluorobenzenesulfonamide, 1-bromo-4-[(chloromethyl)sulfonyl]benzene, 2-(dichloromethyl)-2-methyl-1,3-dioxolane (MG 191), 4-(dichloroacetyl)-1-oxa-4-azospiro[4.5]decane (MON 4660), 2,2-dichloro-1-(2,2,5-trimethyl-3-oxazolidinyl)-ethanone and 2-methoxy-N-[[4-[[(methylamino)carbonyl]amino]phenyl]sulfonyl]-benzamide.

The compounds of Formula 1 can be prepared by general methods known in the art of synthetic organic chemistry. Of note are the following methods described in Schemes 1-5 and variations thereof. The definitions of $R^1$, $R^7$, $R^9$, $Q^1$, $Q^2$, $Y^1$, $Y^2$, J and W in the compounds of Formulae 1 through 2 below are as defined above in the Summary of the Invention unless otherwise noted. Formulae 1A-1F are various subsets of a compound of Formula 1. Substituents for each subset Formula are as defined for its parent Formula unless otherwise noted.

A Compound of Formula 1 can be prepared by reaction of a compound of Formula 2 with an electrophile as shown in Scheme 1. The addition and substitution reactions are carried out in the presence of a stoichiometric, superstoichiometric, or catalytic amount of base and typically in the presence of a co-solvent. Suitable bases for the reaction include, but are not limited to, sodium hydride, sodium methoxide, sodium ethoxide, cesium carbonate, potassium carbonate, potassium tert-butoxide, lithium diisopropylamide, lithium bis(trimethylsilyl)amide, sodium bis(trimethylsilyl)amide, potassium bis(trimethylsilyl)amide, pyridine, triethylamine, and N,N-diisopropylethylamine. Suitable electrophiles for the reaction include, but are not limited to acyl chlorides, acyl anhydrides, chloroformates, cyanoformates, isocyanates, aldehydes, ketones, imines, iminium halides, electron-deficient alkenes (such as acrylates, acrylamides, acrylonitriles, vinylketones, and vinylsulfones), alkylhalides, and alkylsulfonates. Typically the reaction is conducted in a solvent such as water, methanol, ethanol, tetrahydrofuran, dimethylsulfoxide, N,N-dimethylformamide, N,N-dimethylacetamide, N-methylpyrrolidinone and acetonitrile or a mixture thereof at temperatures ranging from −78° C. to the reflux temperature of the solvent. The method of Scheme 1 for the preparation of compounds of Formula 1 wherein L is L-1 utilizing lithium bis(trimethylsilyl)amide and acetyl chloride is illustrated by Step A of Synthesis Example 3. The method of Scheme 1 for the preparation of compounds of Formula 1 wherein L is L-3 utilizing a catalytic amount of potassium hydroxide and paraformaldehyde is illustrated by Step A of Synthesis Example 1.

Scheme 1

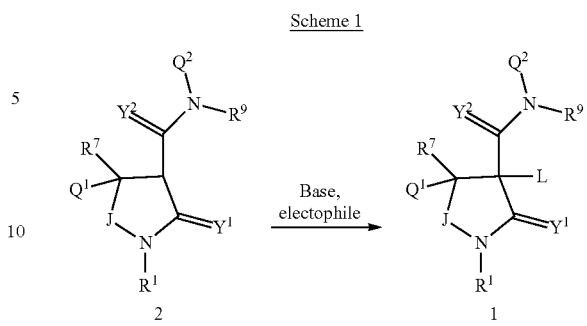

A compound of Formula 1B (i.e. a compound of Formula 1 wherein L is L-3 and $R^F$ is other than H) can be prepared by reaction of an alcohol of Formula 1A (i.e. a compound of Formula 1 wherein L is L-3 and $R^F$ is H) with an electrophile as shown in Scheme 2. The reactions are carried out in the presence of a suitable base and typically in the presence of a co-solvent. Suitable bases for the reaction include, but are not limited to, sodium hydride, sodium methoxide, sodium ethoxide, cesium carbonate, potassium carbonate, potassium tert-butoxide, lithium diisopropylamide, lithium bis(trimethylsilyl)amide, sodium bis(trimethylsilyl)amide, potassium bis(trimethylsilyl)amide, pyridine, triethylamine, and N,N-diisopropylethylamine. Suitable electrophiles for the reaction include, but are not limited to acyl chlorides, acyl anhydrides, chloroformates, cyanoformates, isocyanates, sulfonyl chlorides, sulfinyl chlorides, and phosphoryl chlorides. Typically the reaction is conducted in a solvent such as water, methanol, ethanol, tetrahydrofuran, dimethylsulfoxide, N,N-dimethylformamide, N,N-dimethylacetamide, N-methylpyrrolidinone and acetonitrile or a mixture thereof at temperatures ranging from −78° C. to the reflux temperature of the solvent. The method of Scheme 2 for the preparation of compounds of Formula 1A wherein L is L-3 utilizing pyridine and acetyl chloride is illustrated by Step A of Synthesis Example 2.

Scheme 2

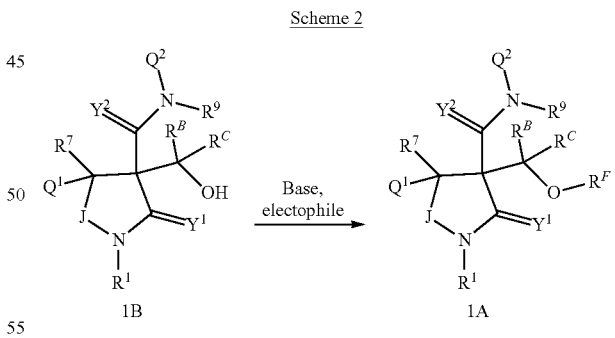

A compound of Formula 1D (i.e. a compound of Formula 1 wherein L is L-2 and $R^D$ is other than H) can be prepared by reaction of compounds of Formula 1C (i.e. a compound of Formula 1 wherein L is L-2 and $R^D$ is H) with an electrophile as shown in Scheme 3. The reactions are carried out in the presence of a suitable base and typically in the presence of a co-solvent. Suitable bases for the reaction include, but are not limited to, sodium hydride, sodium methoxide, sodium ethoxide, cesium carbonate, potassium carbonate, potassium tert-butoxide, lithium diisopropylamide, lithium bis(trimethylsilyl)amide, sodium bis(trimethylsilyl)amide, potassium bis(trimethylsilyl)amide, pyridine, triethylamine, and N,N-diisopropylethylamine. Suitable electrophiles for the reaction include, but are not limited to acyl chlorides, acyl anhydrides, chloroformates, cyanoformates, isocyanates, electron-deficient alkenes (such as acrylates, acrylamides, acrylonitriles, vinylketones, and vinylsulfones), alkylhalides, alkylsulfonates, sulfonyl chlorides, sulfinyl chlorides, and phosphoryl chlorides. Typically the reaction is conducted in a solvent such as water, methanol, ethanol, tetrahydrofuran, dimethylsulfoxide, N,N-dimethylformamide, N,N-dimethylacetamide, N-methylpyrrolidinone and acetonitrile or a mixture thereof at temperatures ranging from −78° C. to the reflux temperature of the solvent.

Scheme 4

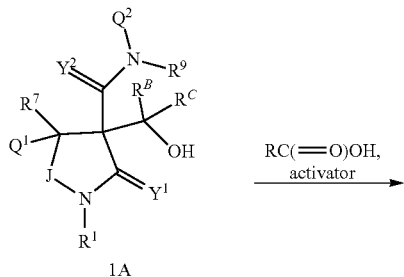

Scheme 3

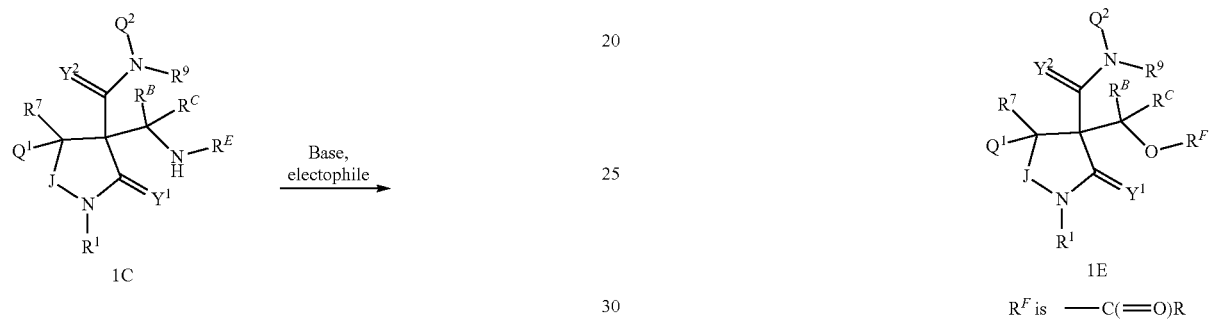

A compound of Formula 1E (i.e. a compound of Formula 1 wherein L is L-3 and $R^F$ is C(=O)R where the atom bonded to the carbonyl is carbon) can also be prepared by reaction of carboxylic acids with an alcohol of Formula 1A (i.e. a compound of Formula 1 wherein L is L-3 and $R^F$ is H) in the presence of a dehydrative coupling reagent such as propylphosphonic anhydride, dicyclohexylcarbodiimide, N-(3-dimethylaminopropyl)-N'-ethylcarbodiimide, N,N'-carbonyldiimidazole, 2-chloro-1,3-dimethylimidazolium chloride or 2-chloro-1-methylpyridinium iodide, optionally in the presence of a catalyst such as N,N-dimethyl-4-aminopyridine as shown in Scheme 4. Polymer-supported reagents, such as polymer-supported cyclohexylcarbodiimide, are also suitable. These reactions are typically run at temperatures ranging from 0° C. to the boiling point of the solvent in a solvent such as dichloromethane, acetonitrile, N,N-dimethylformamide or ethyl acetate in the presence of a base such as triethylamine, N,N-diisopropylamine, or 1,8-diazabicyclo[5.4.0]undec-7-ene.

A compound of Formula 1F (i.e. a compound of Formula 1 wherein L is L-2 and $R^D$ is C(O)R where the atom bonded to the carbonyl is carbon) can also be prepared by reaction of carboxylic acids with a compound of Formula 1C (i.e. a compound of Formula 1 wherein L is L-2 and $R^D$ is H) in the presence of a dehydrative coupling reagent such as propylphosphonic anhydride, dicyclohexylcarbodiimide, N-(3-dimethylaminopropyl)-N'-ethylcarbodiimide, N,N'-carbonyldiimidazole, 2-chloro-1,3-dimethylimidazolium chloride or 2-chloro-1-methylpyridinium iodide as shown in Scheme 5. Polymer-supported reagents, such as polymer-supported cyclohexylcarbodiimide, are also suitable. These reactions are typically run at temperatures ranging from 0 to 60° C. in a solvent such as dichloromethane, acetonitrile, N,N-dimethylformamide or ethyl acetate in the presence of a base such as triethylamine, N,N-diisopropylamine, or 1,8-diazabicyclo[5.4.0]undec-7-ene. See *Organic Process Research & Development* 2009, 13, 900-906 for coupling conditions employing propylphosphonic anhydride.

Scheme 5

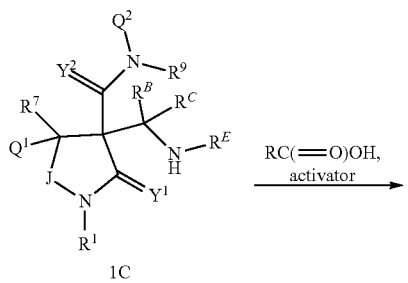

-continued

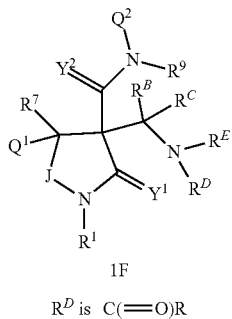

1F

R^D is C(=O)R

It is recognized by one skilled in the art that various functional groups can be converted into others to provide different compounds of Formula 1. For a valuable resource that illustrates the interconversion of functional groups in a simple and straightforward fashion, see Larock, R. C., *Comprehensive Organic Transformations: A Guide to Functional Group Preparations,* 2nd Ed., Wiley-VCH, New York, 1999. For example, intermediates for the preparation of compounds of Formula 1 may contain aromatic nitro groups, which can be reduced to amino groups, and then be converted via reactions well known in the art such as the Sandmeyer reaction, to various halides, providing compounds of Formula 1. The above reactions can also in many cases be performed in alternate order It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products.

The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after the introduction of a given reagent as depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following non-limiting Examples are illustrative of the invention. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane in CDCl$_3$ at 500 Mhz unless otherwise noted; "s" means singlet, "d" means doublet, "t" means triplet, "q" means quartet, "m" means multiplet, "dd" means doublet of doublets, "dt" means doublet of triplets, and "br s" means broad singlet.

Synthesis Example 1

Preparation of (3S,4R)—N-(2,3-difluorophenyl)-3-(hydroxymethyl)-1-methyl-2-oxo-4-[4-(trifluoromethyl)phenyl]-3-pyrrolidinecarboxamide (Compounds 4 and 5)

Step A: Preparation of (3S,4R)—N-(2,3-difluorophenyl)-3-(hydroxymethyl)-1-methyl-2-oxo-4-[4-(trifluoromethyl)phenyl]-3-pyrrolidinecarboxamide A solution of (3S,4S)—N-(2,3-difluorophenyl)-1-methyl-2-oxo-4-[4-(trifluoromethyl)phenyl]-3-pyrrolidinecarboxamide (0.80 g, 2.0 mmol), paraformaldehyde (0.072 g, 2.4 mmol) and potassium hydroxide (0.002 g, 0.04 mmol) were added to tetrahydrofuran (16 mL) and heated to the reflux temperature of the solvent for 30 min. The reaction mixture was concentrated to afford the crude product. The crude product was purified by column chromatography, eluting with 0% to 100% ethyl acetate in hexanes, to afford the title compound, a compound of the present invention, as a colorless oil (0.20 g) and its diastereomer ((3R,4R)—N-(2,3-difluorophenyl)-3-(hydroxymethyl)-1-methyl-2-oxo-4-[4-(trifluoromethyl)phenyl]-3-pyrrolidinecarboxamide), a compound of the present invention, as a colorless solid (0.60 g).

$^1$H NMR δ 10.22 (br s, 1H), 7.52 (d, J=8.2 Hz, 2H), 7.50-7.45 (m, 1H), 7.33 (d, J=8.2 Hz, 2H), 6.99-6.82 (m, 2H), 4.18-4.08 (m, 1H), 4.07-4.00 (m, 1H), 3.98-3.83 (m, 2H), 3.56-3.48 (m, 1H), 3.15-3.11 (m, 1H), 3.07 (s, 3H).

diastereomer: $^1$H NMR δ 10.27 (br s, 1H), 8.03-7.97 (m, 1H), 7.72 (d, J=8.4 Hz, 2H), 7.64 (d, J=8.4 Hz, 2H), 7.08-6.99 (m, 1H), 6.95-6.86 (m, 1H), 4.40-4.33 (m, 1H), 3.91-3.64 (m, 4H), 3.08 (s, 3H), 2.24-2.20 (m, 1H).

Synthesis Example 2

Preparation of (3S,4R)-3-[(acetyloxy)methyl]-N-(2,3-difluorophenyl)-1-methyl-2-oxo-4-[4-(trifluoromethyl)phenyl]-3-pyrrolidincarboxamide (Compound 2)

Step A: Preparation of (3S,4R)-3-[(acetyloxy)methyl]-N-(2,3-difluorophenyl)-1-methyl-2-oxo-4-[4-(trifluoromethyl)phenyl]-3-pyrrolidincarboxamide (3S,4R)—N-(2,3-difluorophenyl)-3-(hydroxymethyl)-1-methyl-2-oxo-4-[4-(trifluoromethyl)phenyl]-3-pyrrolidinecarboxamide and (3R,4R)—N-(2,3-difluorophenyl)-3-(hydroxymethyl)-1-methyl-2-oxo-4-[4-(trifluoromethyl)phenyl]-3-pyrrolidinecarboxamide (i.e. the products of Synthesis Example 1) (0.080 g, 0.19 mmol) and pyridine (0.020 mL, 0.22 mmol) were dissolved in dichloromethane (1.0 mL). Acetyl chloride (0.015 mL, 0.22 mmol) was added and the solution was stirred at 23° C. for 20 min. The reaction mixture was concentrated onto silica gel and purified by column chromatography, eluting with 0% to 50% ethyl acetate in hexanes, to afford the title compound, a compound of the present invention, as a pale yellow oil (0.045 g).

¹H NMR δ 10.51 (br s, 1H), 7.55-7.44 (m, 3H), 7.31-7.26 (m, 2H), 6.94-6.81 (m, 2H), 4.81 (d, J=10.9 Hz, 1H), 4.47 (d, J=10.9 Hz, 1H), 4.06-3.98 (m, 1H), 3.65-3.59 (m, 1H), 3.35-3.29 (m, 1H), 3.05 (s, 3H), 2.10 (s, 3H).

Synthesis Example 3

Preparation of (3S,4R)-3-acetyl-N-(2,3-difluorophenyl)-1-methyl-2-oxo-4-[4-(trifluoromethyl)phenyl]-3-pyrrolidinecarboxamide (Compound 3)

Step A: Preparation of (3S,4R)-3-acetyl-N-(2,3-difluorophenyl)-1-methyl-2-oxo-4-[4-(trifluoromethyl)phenyl]-3-pyrrolidinecarboxamide (3S,4S)—N-(2,3-difluorophenyl)-1-methyl-2-oxo-4-methyl-2-oxo-4-[4-(trifluoromethyl)phenyl]-3-pyrrolidinecarboxamide (0.10 g, 0.25 mmol) was dissolved in tetrahydrofuran (10 mL) and cooled to 0° C. A solution of lithium bis(trimethylsilyl)amide in tetrahydrofuran (1.0 M, 0.50 mL, 0.50 mmol) was added and stirred at 0° C. for 10 min. Acetyl chloride (0.020 mL, 0.28 mmol) was added. The reaction was warmed to 23° C. and stirred for 20 min. The reaction mixture was concentrated onto silica gel and purified by column chromatography, eluting with 0% to 50% ethyl acetate in hexanes, to afford the title compound, a compound of the present invention, as a colorless solid (0.021 g).

¹H NMR δ 10.62 (br s, 1H), 7.51 (d, J=8.0 Hz, 2H), 7.40-7.33 (m, 1H), 7.28 (d, J=8.2 Hz, 2H), 6.95-6.84 (m, 2H), 4.38-4.34 (m, 1H), 4.04-3.98 (m, 1H), 3.06 (s, 3H), 2.42 (s, 3H).

By the procedures described herein together with methods known in the art, the following compounds of Tables 1 to 1008 can be prepared. The following abbreviations are used in the Tables which follow: i means iso, c means cyclo, Me means methyl, Et means ethyl, Pr means propyl, Bu means butyl, c-Pr cyclopropyl, c-Bu means cyclobutyl, Ph means phenyl, OMe means methoxy, OEt means ethoxy, Py means pyridinyl, —NO₂ means nitro.

TABLE 1

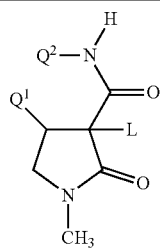

L is L-1; R⁴ is Me; Q² is Ph(2-F); and Q¹ is:

| Q¹ | Q¹ | Q¹ |
|---|---|---|
| Ph(3-Cl) | Ph(3-CF₃) | Ph(3-OCF₂H) |
| Ph(3-F) | Ph(3-CHF₂) | Ph(3-OMe) |
| Ph(3-Br) | Ph(3-CH₂F) | Ph(3-OCF₂CF₂H) |
| Ph(3-Me) | Ph(3-OCF₃) | Ph(4-Cl) |
| Ph(4-F) | 2-Py(6-F) | 4-Py(2-Me,6-F) |
| Ph(4-Br) | 2-Py(6-CF₃) | 4-Py(2-OMe,6-F) |
| Ph(4-Me) | 2-Py(6-Me) | 4-Py(2-OEt,6-F) |
| Ph(4-CF₃) | 2-Py(5-F) | 4-Py(2,6-di-F) |
| Ph(4-CHF₂) | 2-Py(5-CF₃) | 4-Py(2-Me,6-CH₂F) |
| Ph(4-CH₂F) | 2-Py(5-Me) | 4-Py(2-OMe,6-CH₂F) |
| Ph(4-OCF₃) | 2-Py(4-F) | 4-Py(2-OEt,6-CH₂F) |
| Ph(4-OCF₂H) | 2-Py(4-CF₃) | 4-Py(2-F,6-CH₂F) |
| Ph(4-OMe) | 2-Py(4-Me) | 4-Py(2-Me,6-OCHF₂) |

TABLE 1-continued

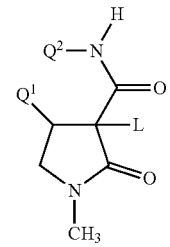

L is L-1; R⁴ is Me; Q² is Ph(2-F); and Q¹ is:

| Q¹ | Q¹ | Q¹ |
|---|---|---|
| Ph(4-OCF₂CF₂H) | 2-Py(3-F) | 4-Py(2-OMe,6-OCHF₂) |
| Ph(2,3-di-F) | 2-Py(3-CF₃) | 4-Py(2-OEt,6-OCHF₂) |
| Ph(2,4-di-F) | 2-Py(3-Me) | 4-Py(2-F,6-OCHF₂) |
| Ph(2,5-di-F) | 3-Py | 2-Thienyl |
| Ph(2,6-di-F) | 3-Py(6-F) | 2-Thienyl(4-CF₃) |
| Ph(3,4-di-F) | 3-Py(6-CF₃) | 2-Thienyl(5-CF₃) |
| Ph(3,5-di-F) | 3-Py(6-Me) | 3-Thienyl |
| Ph(3-Me,4-F) | 3-Py(5-F) | 3-Thienyl(4-CF₃) |
| Ph(3-F,4-Me) | 3-Py(5-CF₃) | 3-Thienyl(5-CF₃) |
| Ph(3-CF₃,4-F) | 3-Py(5-Me) | 2-Furyl |
| Ph(3-F,4-CF₃) | 3-Py(4-F) | 2-Furyl(4-CF₃) |
| Ph(3-CHF₂,4-F) | 3-Py(4-CF₃) | 2-Furyl(5-CF₃) |
| Ph(3-CH₂F,4-F) | 3-Py(4-Me) | 3-Furyl |
| Ph(3,5-di-Et) | 3-Py(2-F) | 3-Furyl(4-CF₃) |
| Ph(3-Me,5-OMe) | 3-Py(2-CF₃) | 3-Furyl(5-CF₃) |
| Ph(3,5-di-OMe) | 3-Py(2-Me) | Pyrazin-2-yl |
| Ph(3-OMe,5-OEt) | 4-Py | Pyrazin-2-yl(5-CF₃) |
| Ph(3-Me,5-CH₂F) | 4-Py(3-F) | Pyrimidin-2-yl |
| Ph(3-OMe,5-CH₂F) | 4-Py(3-CF₃) | Pyrimidin-2-yl(5-CF₃) |
| Ph(3-OEt,5-CH₂F) | 4-Py(3-Me) | Pyrimidin-5-yl |
| Ph(2,3,4-tri-F) | 4-Py(2-F) | Pyrimidin-5-yl(2-CF₃) |
| Ph(3,4,5-tri-F) | 4-Py(2-CF₃) | 1,3-Dioxolan-4-yl |
| 2-Py | 4-Py(2-OMe,6-OEt) | 2,2-di-F-1,3-Dioxolan-4-yl |

Table 2 is constructed in the same manner as Table 1 except that the Row Heading "L is L-1; R⁴ is Me; Q² is Ph(2-F); and Q¹ is" is replaced with the Row Heading listed for Table 2 below (i.e. "L is L-1; R⁴ is Me; Q² is Ph(2,3-di-F); and Q¹ is"). Therefore the first entry in Table 2 is a compound of Formula 1 wherein J is —CH₂—; Q² is Ph(2,3-di-F); Q¹ is Ph(3-Cl) (i.e. 3-chlorophenyl); Y¹ is O; Y² is O; R⁷ is H; R⁹ is H; L is L-1; and R⁴ is Me. Tables 3 through 16 are constructed similarly.

| Table | Row Heading |
|---|---|
| 2 | L is L-1; R⁴ is Me; Q² is Ph(2,3-di-F); and Q¹ is |
| 3 | L is L-1; R⁴ is Me; Q² is Ph(2,4-di-F); and Q¹ is |
| 4 | L is L-1; R⁴ is Me; Q² is Ph(2,3,4-tri-F); and Q¹ is |
| 5 | L is L-1; R⁴ is Me; Q² is Ph(2-CF₃); and Q¹ is |
| 6 | L is L-1; R⁴ is Me; Q² is Ph(2-Me); and Q¹ is |
| 7 | L is L-1; R⁴ is Me; Q² is Ph(2-NO₂); and Q¹ is |
| 8 | L is L-1; R⁴ is Me; Q² is Ph(2-Cl); and Q¹ is |
| 9 | L is L-1; R⁴ is Me; Q² is Ph(2-SO₂Me); and Q¹ is |
| 10 | L is L-1; R⁴ is Me; Q² is Ph(2-F,3-Cl); and Q¹ is |
| 11 | L is L-1; R⁴ is Me; Q² is Ph(2-SOMe); and Q¹ is |
| 12 | L is L-1; R⁴ is Me; Q² is Ph(2-SMe); and Q¹ is |
| 13 | L is L-1; R⁴ is Me; Q² is Ph(2-Me,3-F); and Q¹ is |
| 14 | L is L-1; R⁴ is Me; Q² is 3-Pyridinyl(2,6-di-F); and Q¹ is |
| 15 | L is L-1; R⁴ is Me; Q² is 3-Pyridinyl(2-F); and Q¹is |
| 16 | L is L-1; R⁴ is Me; Q² is 2-Pyridinyl(6-F); and Q¹ is |

Table 17 through 1008

Tables 17 through 1008 are constructed the same way as Tables 1 through 16 except that the part of the Row Heading referring to the identity of L, "L is L-1; R⁴ is Me", is replaced with the part of the Row Heading referring to the identity of L listed for Tables 17 through 32 below (i.e. "L is L-1; $R^4$ is Et"). Therefore the first entry in Table 17 is a compound of Formula 1 wherein J is —CH$_2$—; $Q^2$ is Ph(2,3-di-F); $Q^1$ is Ph(3-Cl) (i.e. 3-chlorophenyl); $Y^1$ is O; $Y^2$ is O; $R^7$ is H; $R^9$ is H; L is L-1; and $R^4$ is Et.

| Tables | Row Heading |
|---|---|
| 17-32 | L is L-1; $R^4$ is Me |
| 33-48 | L is L-1; $R^4$ is Et |
| 49-64 | L is L-1; $R^4$ is n-Pr |
| 65-80 | L is L-1; $R^4$ is i-Pr |
| 81-96 | L is L-1; $R^4$ is c-Pr |
| 97-112 | L is L-1; $R^4$ is n-Bu |
| 113-128 | L is L-1; $R^4$ is CF$_3$ |
| 129-144 | L is L-1; $R^4$ is CCl$_3$ |
| 145-160 | L is L-1; $R^4$ is Ph |
| 161-176 | L is L-1; $R^4$ is Ph(2-Me) |
| 177-192 | L is L-1; $R^4$ is Ph(3-Me) |
| 193-208 | L is L-1; $R^4$ is Ph(4-Me) |
| 209-224 | L is L-1; $R^4$ is OMe |
| 225-240 | L is L-1; $R^4$ is OEt |
| 241-256 | L is L-2; $R^B$ is H; $R^C$ is H; $R^D$ is H; $R^E$ is Me |
| 257-272 | L is L-2; $R^B$ is H; $R^C$ is H; $R^D$ is H; $R^E$ is Et |
| 273-288 | L is L-2; $R^B$ is H; $R^C$ is H; $R^D$ is H; $R^E$ is n-Pr |
| 289-304 | L is L-2; $R^B$ is H; $R^C$ is H; $R^D$ is H; $R^E$ is c-Pr |
| 305-320 | L is L-2; $R^B$ is H; $R^C$ is H; $R^D$ is H; $R^E$ is COMe |
| 321-336 | L is L-2; $R^B$ is H; $R^C$ is H; $R^D$ is H; $R^E$ is COPh |
| 337-352 | L is L-2; $R^B$ is H; $R^C$ is H; $R^D$ is H; $R^E$ is COOMe |
| 353-368 | L is L-2; $R^B$ is H; $R^C$ is H; $R^D$ is H; $R^E$ is COOEt |
| 369-384 | L is L-2; $R^B$ is H; $R^C$ is H; $R^D$ is H; $R^E$ is SO$_2$Me |
| 385-400 | L is L-2; $R^B$ is H; $R^C$ is H; $R^D$ is H; $R^E$ is SO$_2$Ph |
| 401-416 | L is L-2; $R^B$ is H; $R^C$ is H; $R^D$ is Me; $R^E$ is Me |
| 417-432 | L is L-2; $R^B$ is H; $R^C$ is H; $R^D$ is Me; $R^E$ is Et |
| 433-448 | L is L-2; $R^B$ is H; $R^C$ is H; $R^D$ is Me; $R^E$ is n-Pr |
| 449-464 | L is L-2; $R^B$ is H; $R^C$ is H; $R^D$ is Me; $R^E$ is c-Pr |
| 465-480 | L is L-2; $R^B$ is H; $R^C$ is H; $R^D$ is Me; $R^E$ is COMe |
| 481-496 | L is L-2; $R^B$ is H; $R^C$ is H; $R^D$ is Me; $R^E$ is COPh |
| 497-512 | L is L-2; $R^B$ is H; $R^C$ is H; $R^D$ is Me; $R^E$ is COOMe |
| 513-528 | L is L-2; $R^B$ is H; $R^C$ is H; $R^D$ is Me; $R^E$ is COOEt |
| 529-544 | L is L-2; $R^B$ is H; $R^C$ is H; $R^D$ is Me; $R^E$ is SO$_2$Me |
| 545-560 | L is L-2; $R^B$ is H; $R^C$ is H; $R^D$ is Me; $R^E$ is SO$_2$Ph |
| 561-576 | L is L-2; $R^B$ is H; $R^C$ is H; $R^D$ is Et; $R^E$ is Me |
| 577-592 | L is L-2; $R^B$ is H; $R^C$ is H; $R^D$ is Et; $R^E$ is Et |
| 593-608 | L is L-2; $R^B$ is H; $R^C$ is H; $R^D$ is Et; $R^E$ is n-Pr |
| 609-624 | L is L-2; $R^B$ is H; $R^C$ is H; $R^D$ is Et; $R^E$ is c-Pr |
| 625-640 | L is L-2; $R^B$ is H; $R^C$ is H; $R^D$ is Et; $R^E$ is COMe |
| 641-656 | L is L-2; $R^B$ is H; $R^C$ is H; $R^D$ is Et; $R^E$ is COPh |
| 657-672 | L is L-2; $R^B$ is H; $R^C$ is H; $R^D$ is Et; $R^E$ is COOMe |
| 673-688 | L is L-2; $R^B$ is H; $R^C$ is H; $R^D$ is Et; $R^E$ is COOEt |
| 689-704 | L is L-2; $R^B$ is H; $R^C$ is H; $R^D$ is Et; $R^E$ is SO$_2$Me |
| 705-720 | L is L-2; $R^B$ is H; $R^C$ is H; $R^D$ is Et; $R^E$ is SO$_2$Ph |
| 721-736 | L is L-3; $R^B$ is H; $R^C$ is H; $R^F$ is COMe |
| 737-752 | L is L-3; $R^B$ is H; $R^C$ is H; $R^F$ is COCF$_3$ |
| 753-768 | L is L-3; $R^B$ is H; $R^C$ is H; $R^F$ is COPh |
| 769-784 | L is L-3; $R^B$ is H; $R^C$ is H; $R^F$ is COOMe |
| 785-800 | L is L-3; $R^B$ is H; $R^C$ is H; $R^F$ is COOEt |
| 801-816 | L is L-3; $R^B$ is H; $R^C$ is H; $R^F$ is SO$_2$Me |
| 817-832 | L is L-3; $R^B$ is H; $R^C$ is H; $R^F$ is SO$_2$Ph |
| 833-848 | L is L-3; $R^B$ is H; $R^C$ is H; $R^F$ is PO(OH)$_2$ |
| 849-864 | L is L-3; $R^B$ is H; $R^C$ is H; $R^F$ is PO(OMe)$_2$ |
| 865-880 | L is L-4; Both $R^B$'s are each H; Both $R^C$'s are each H; $R^G$ is COMe |
| 881-896 | L is L-4; Both $R^B$'s are each H; Both $R^C$'s are each H; $R^G$ is COCF$_3$ |
| 897-912 | L is L-4; Both $R^B$'s are each H; Both $R^C$'s are each H; $R^G$ is COPh |
| 913-928 | L is L-4; Both $R^B$'s are each H; Both $R^C$'s are each H; $R^G$ is COOMe |
| 929-944 | L is L-4; Both $R^B$'s are each H; Both $R^C$'s are each H; $R^G$ is COOEt |
| 945-960 | L is L-4; Both $R^B$'s are each H; Both $R^C$'s are each H; $R^G$ is SO$_2$Me |
| 961-976 | L is L-4; Both $R^B$'s are each H; Both $R^C$'s are each H; $R^G$ is SO$_2$Ph |

-continued

| Tables | Row Heading |
|---|---|
| 977-992 | L is L-4; Both $R^B$'s are each H; Both $R^C$'s are each H; $R^G$ is PO(OH)$_2$ |
| 993-1008 | L is L-4; Both $R^B$'s are each H; Both $R^C$'s are each H; $R^G$ is PO(OMe)$_2$ |

A compound of this invention will generally be used as a herbicidal active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions, oil-in-water emulsions, flowable concentrates and/or suspoemulsions) and the like, which optionally can be thickened into gels. The general types of aqueous liquid compositions are soluble concentrate, suspension concentrate, capsule suspension, concentrated emulsion, microemulsion, oil-in-water emulsion, flowable concentrate and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water, but occasionally another suitable medium like an aromatic or paraffinic hydrocarbon or vegetable oil. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting.

The formulations will typically contain effective amounts of active ingredient, diluent and surfactant within the following approximate ranges which add up to 100 percent by weight.

|  | Weight Percent | | |
| --- | --- | --- | --- |
|  | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), alkyl phosphates (e.g., triethyl phosphate), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters, alkyl and aryl benzoates and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol, cresol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide,* 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 m can be wet milled using media mills to obtain particles with average diameters below 3 m. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48; *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food—Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, U K, 2000.

In the following Examples, all percentages are by weight and all formulations are prepared in conventional ways. Compound numbers refer to compounds in Index Table A. Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except where otherwise indicated.

Example A

| High Strength Concentrate | |
| --- | --- |
| Compound 1 | 98.5% |
| silica aerogel | 0.5% |
| synthetic amorphous fine silica | 1.0% |

Example B

| Wettable Powder | |
| --- | --- |
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

| Granule | |
| --- | --- |
| Compound 1 | 10.0% |
| attapulgite granules (low volatile matter, 0.71/0.30 mm; U.S.S. No. 25-50 sieves) | 90.0% |

Example D

| Extruded Pellet | |
| --- | --- |
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

| Emulsifiable Concentrate | |
|---|---|
| Compound 1 | 10.0% |
| polyoxyethylene sorbitol hexoleate | 20.0% |
| $C_6$-$C_{10}$ fatty acid methyl ester | 70.0% |

Example F

| Microemulsion | |
|---|---|
| Compound 1 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example G

| Suspension Concentrate | |
|---|---|
| Compound 1 | 35% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| water | 53.7% |

Example H

| Emulsion in Water | |
|---|---|
| Compound 1 | 10.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0 |
| water | 58.7% |

Example I

| Oil Dispersion | |
|---|---|
| Compound 1 | 25% |
| polyoxyethylene sorbitol hexaoleate | 15% |
| organically modified bentonite clay | 2.5% |
| fatty acid methyl ester | 57.5% |

The present disclosure also includes Examples A through I above except "Compound 1" is replaced with "Compound 2" and "Compound 3". "Compound 4", "Compound 5", "Compound 6", "Compound 7", "Compound 8" or "Compound 9" above. Test results indicate that the compounds of the present invention are highly active preemergent and/or postemergent herbicides and/or plant growth regulants. The compounds of the invention generally show highest activity for postemergence weed control (i.e. applied after weed seedlings emerge from the soil) and preemergence weed control (i.e. applied before weed seedlings emerge from the soil). Many of them have utility for broad-spectrum pre- and/or postemergence weed control in areas where complete control of all vegetation is desired such as around fuel storage tanks, industrial storage areas, parking lots, drive-in theaters, air fields, river banks, irrigation and other waterways, around billboards and highway and railroad structures. Many of the compounds of this invention, by virtue of selective metabolism in crops versus weeds, or by selective activity at the locus of physiological inhibition in crops and weeds, or by selective placement on or within the environment of a mixture of crops and weeds, are useful for the selective control of grass and broadleaf weeds within a crop/weed mixture. One skilled in the art will recognize that the preferred combination of these selectivity factors within a compound or group of compounds can readily be determined by performing routine biological and/or biochemical assays. Compounds of this invention may show tolerance to important agronomic crops including, but is not limited to, alfalfa, barley, cotton, wheat, rape, sugar beets, corn (maize), sorghum, soybeans, rice, oats, peanuts, vegetables, tomato, potato, perennial plantation crops including coffee, cocoa, oil palm, rubber, sugarcane, citrus, grapes, fruit trees, nut trees, banana, plantain, pineapple, hops, tea and forests such as *eucalyptus* and conifers (e.g., loblolly pine), and turf species (e.g., Kentucky bluegrass, St. Augustine grass, Kentucky fescue and Bermuda grass). Compounds of this invention can be used in crops genetically transformed or bred to incorporate resistance to herbicides, express proteins toxic to invertebrate pests (such as *Bacillus thuringiensis* toxin), and/or express other useful traits. Those skilled in the art will appreciate that not all compounds are equally effective against all weeds. Alternatively, the subject compounds are useful to modify plant growth.

As the compounds of the invention have both preemergent and postemergent herbicidal activity, to control undesired vegetation by killing or injuring the vegetation or reducing its growth, the compounds can be usefully applied by a variety of methods involving contacting a herbicidally effective amount of a compound of the invention, or a composition comprising said compound and at least one of a surfactant, a solid diluent or a liquid diluent, to the foliage or other part of the undesired vegetation or to the environment of the undesired vegetation such as the soil or water in which the undesired vegetation is growing or which surrounds the seed or other propagule of the undesired vegetation. Undesired vegetation includes at least one selected from the group consisting of grass weeds and broadleaf weeds. Undesired vegetation is selected from the group consisting of annual bluegrass, Benghal dayflower, blackgrass, black nightshade, broadleaf signalgrass, Canada thistle, cheat, common cocklebur (*Xanthium pensylvanicum*), common ragweed, corn poppies, field violet, giant foxtail, goosegrass, green foxtail, guinea grass, hairy beggarticks, herbicide-resistant black grass, horseweed, Italian rye grass, jimsonweed, Johnson grass (*Sorghum halepense*), large crabgrass, little seed canary grass, morning glory, Pennsylvania smartweed, pitted morning glory, prickly sida, quackgrass, redroot pigweed, shattercane, shepherd's purse, silky windgrass, sunflower (as a weed in a potato crop), wild buckwheat (*Polygonum convolvulus*), wild mustard (*Brassica kaber*), wild oat (*Avena fatua*), wild pointsettia, yellow foxtail, and yellow nutsedge (*Cyperus esculentus*).

A herbicidally effective amount of the compounds of this invention is determined by a number of factors. These factors include: formulation selected, method of application, amount and type of vegetation present, growing conditions, etc. In general, a herbicidally effective amount of compounds of this invention is about 0.001 to 20 kg/ha with a preferred range of about 0.004 to 1 kg/ha. One skilled in the art can easily determine the herbicidally effective amount necessary for the desired level of weed control.

In one common embodiment, a compound of the invention is applied, typically in a formulated composition, to a locus comprising desired vegetation (e.g., crops) and undesired vegetation (i.e. weeds), both of which may be seeds, seedlings and/or larger plants, in contact with a growth medium (e.g., soil). In this locus, a composition comprising a compound of the invention can be directly applied to a plant or a part thereof, particularly of the undesired vegetation, and/or to the growth medium in contact with the plant.

Plant varieties and cultivars of the desired vegetation in the locus treated with a compound of the invention can be obtained by conventional propagation and breeding methods or by genetic engineering methods. Genetically modified plants (transgenic plants) are those in which a heterologous gene (transgene) has been stably integrated into the plant's genome. A transgene that is defined by its particular location in the plant genome is called a transformation or transgenic event.

Genetically modified plant cultivars in the locus which can be treated according to the invention include those that are resistant against one or more biotic stresses (pests such as nematodes, insects, mites, fungi, etc.) or abiotic stresses (drought, cold temperature, soil salinity, etc.), or that contain other desirable characteristics. Plants can be genetically modified to exhibit traits of, for example, herbicide tolerance, insect-resistance, modified oil profiles or drought tolerance.

Although most typically, compounds of the invention are used to control undesired vegetation, contact of desired vegetation in the treated locus with compounds of the invention may result in super-additive or synergistic (enhanced) effects with genetic traits in the desired vegetation, including traits incorporated through genetic modification. For example, resistance to phytophagous insect pests or plant diseases, tolerance to biotic/abiotic stresses or storage stability may be greater than expected from the genetic traits in the desired vegetation.

Compounds of this invention can also be mixed with one or more other biologically active compounds or agents including herbicides, herbicide safeners, fungicides, insecticides, nematocides, bactericides, acaricides, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Mixtures of the compounds of the invention with other herbicides can broaden the spectrum of activity against additional weed species, and suppress the proliferation of any resistant biotypes. Thus the present invention also pertains to a composition comprising a compound of Formula 1 (in a herbicidally effective amount) and at least one additional biologically active compound or agent (in a biologically effective amount) and can further comprise at least one of a surfactant, a solid diluent or a liquid diluent. The other biologically active compounds or agents can be formulated in compositions comprising at least one of a surfactant, solid or liquid diluent. For mixtures of the present invention, one or more other biologically active compounds or agents can be formulated together with a compound of Formula 1, to form a premix, or one or more other biologically active compounds or agents can be formulated separately from the compound of Formula 1, and the formulations combined together before application (e.g., in a spray tank) or, alternatively, applied in succession.

A mixture of one or more of the following herbicides with a compound of this invention may be particularly useful for weed control: acetochlor, acifluorfen and its sodium salt, aclonifen, acrolein (2-propenal), alachlor, alloxydim, ametryn, amicarbazone, amidosulfuron, aminocyclopyrachlor and its esters (e.g., methyl, ethyl) and salts (e.g., sodium, potassium), aminopyralid, amitrole, ammonium sulfamate, anilofos, asulam, atrazine, azimsulfuron, beflubutamid, S-beflubutamide, benazolin, benazolin-ethyl, bencarbazone, benfluralin, benfuresate, bensulfuron-methyl, bensulide, bentazone, benzobicyclon, benzofenap, bicyclopyrone, bifenox, bilanafos, bispyribac and its sodium salt, bromacil, bromobutide, bromofenoxim, bromoxynil, bromoxynil octanoate, butachlor, butafenacil, butamifos, butralin, butroxydim, butylate, cafenstrole, carbetamide, carfentrazone-ethyl, catechin, chlomethoxyfen, chloramben, chlorbromuron, chlorflurenol-methyl, chloridazon, chlorimuron-ethyl, chlorotoluron, chlorpropham, chlorsulfuron, chlorthal-dimethyl, chlorthiamid, cinidon-ethyl, cinmethylin, cinosulfuron, clacyfos, clefoxydim, clethodim, clodinafop-propargyl, clomazone, clomeprop, clopyralid, clopyralid-olamine, cloransulam-methyl, cumyluron, cyanazine, cycloate, cyclopyranil, cyclopyrimorate, cyclosulfamuron, cycloxydim, cyhalofop-butyl, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, diclosulam, difenzoquat metilsulfate, diflufenican, diflufenzopyr, dimefuron, dimepiperate, dimethachlor, dimethametryn, dimethenamid, dimethenamid-P, dimethipin, dimethylarsinic acid and its sodium salt, dinitramine, dinoterb, diphenamid, diquat dibromide, dithiopyr, diuron, DNOC, endothal, EPTC, esprocarb, ethalfluralin, ethametsulfuron-methyl, ethiozin, ethofumesate, ethoxyfen, ethoxysulfuron, etobenzanid, fenoxaprop-ethyl, fenoxaprop-P-ethyl, fenoxasulfone, fenquinotrione, fentrazamide, fenuron, fenuron-TCA, flamprop-methyl, flamprop-M-isopropyl, flamprop-M-methyl, flazasulfuron, florasulam, fluazifop-butyl, fluazifop-P-butyl, fluazolate, flucarbazone, flucetosulfuron, fluchloralin, flufenacet, flufenpyr, flufenpyr-ethyl, flumetsulam, flumiclorac-pentyl, flumioxazin, fluometuron, fluoroglycofen-ethyl, flupoxam, flupyrsulfuron-methyl and its sodium salt, flurenol, flurenol-butyl, fluridone, flurochloridone, fluroxypyr, flurtamone, fluthiacet-methyl, fomesafen, foramsulfuron, fosamine-ammonium, glufosinate, glufosinate-ammonium, glufosinate-P, glyphosate and its salts such as ammonium, isopropylammonium, potassium, sodium (including sesquisodium) and trimesium (alternatively named sulfosate), halauxifen, halauxifen-methyl, halosulfuron-methyl, haloxyfop-etotyl, haloxyfop-methyl, hexazinone, hydantocidin, imazamethabenz-methyl, imazamox, imazapic, imazapyr, imazaquin, imazaquin-ammonium, imazethapyr, imazethapyr-ammonium, imazosulfuron, indanofan, indaziflam, iofensulfuron, iodosulfuron-methyl, ioxynil, ioxynil octanoate, ioxynil-sodium, ipfencarbazone, isoproturon, isouron, isoxaben, isoxaflutole, isoxachlortole, lactofen, lenacil, linuron, maleic hydrazide, MCPA and its salts (e.g., MCPA-dimethylammonium, MCPA-potassium and MCPA-sodium, esters (e.g., MCPA-2-ethylhexyl, MCPA-butotyl) and thioesters (e.g., MCPA-thioethyl), MCPB and its salts (e.g., MCPB-sodium) and esters (e.g., MCPB-ethyl), mecoprop, mecoprop-P, mefenacet, mefluidide, mesosulfuron-methyl, mesotrione, metam-sodium, metamifop, metamitron, metazachlor, metazosulfuron, methabenzthiazuron, methylarsonic acid and its calcium, monoammonium, monosodium and disodium salts, methyldymron, metobenzuron, metobromuron, metolachlor, S-metolachlor, metosulam, metoxuron, metribuzin, metsulfuron-methyl, molinate, monolinuron, naproanilide, napropamide, napropamide-M, naptalam, neburon, nicosulfuron, norflurazon, orbencarb, orthosulfamuron, oryzalin, oxadiargyl, oxadiazon, oxasulfuron, oxaziclomefone, oxyfluorfen, paraquat dichloride, pebulate, pelargonic acid, pendimethalin, penoxsulam, pentanochlor, pentoxazone, perfluidone, pethoxamid, pethoxyamid, phenmedipham, picloram, picloram-potassium, picolinafen, pinoxaden, piperophos, pretilachlor, primisulfuron-methyl, prodiamine, profoxydim, prometon, prometryn, propachlor, propanil, propaquizafop, propazine, propham, propisochlor, propoxycarbazone, propyrisulfuron, propyzamide, prosulfocarb, prosulfuron, pyraclonil, pyraflufen-ethyl, pyrasulfotole, pyrazogyl, pyrazolynate, pyrazoxyfen, pyrazosulfuron-ethyl, pyribenzoxim, pyributicarb, pyridate, pyriftalid, pyriminobac-methyl, pyrimisulfan, pyrithiobac, pyrithiobac-sodium, pyroxasulfone, pyroxsulam, quinclorac, quinmerac, quinoclamine, quizalofop-ethyl, quizalofop-P-ethyl, quizalofop-P-tefuryl, rimsulfuron, saflufenacil, sethoxydim, siduron, simazine, simetryn, sulcotrione, sulfentrazone, sulfometuron-methyl, sulfosulfuron, 2,3,6-TBA, TCA, TCA-sodium, tebutam, tebuthiuron, tefuryltrione, tembotrione, tepraloxydim, terbacil, terbumeton, terbuthylazine, terbutryn, thenylchlor, thiazopyr, thiencarbazone, thifensulfuron-methyl, thiobencarb, tiafenacil, tiocarbazil, tolpyralate, topramezone, tralkoxydim, triallate, triafamone, triasulfuron, triaziflam, tribenuron-methyl, triclopyr, triclopyr-butotyl, triclopyr-triethylammonium, tridiphane, trietazine, trifloxysulfuron, trifludimoxazin, trifluralin, triflusulfuron-methyl, tritosulfuron, vernolate, 3-(2-chloro-3,6-difluorophenyl)-4-hydroxy-1-methyl-1,5-naphthyridin-2(1H)-one, 5-chloro-3-[(2-hydroxy-6-oxo-1-cyclohexen-1-yl)carbonyl]-1-(4-methoxyphenyl)-2(1H)-quinoxalinone, 2-chloro-N-(1-methyl-1H-tetrazol-5-yl)-6-(trifluoromethyl)-3-pyridinecarboxamide, 7-(3,5-dichloro-4-pyridinyl)-5-(2,2-difluoroethyl)-8-hydroxypyrido[2,3-b]pyrazin-6(5H)-one), 4-(2,6-diethyl-4-methylphenyl)-5-hydroxy-2,6-dimethyl-3 (2H)-pyridazinone), 5-[[(2,6-difluorophenyl)methoxy]methyl]-4,5-dihydro-5-methyl-3-(3-methyl-2-thienyl)isoxazole (previously methioxolin), 4-(4-fluorophenyl)-6-[(2-hydroxy-6-oxo-1-cyclohexen-1-yl)carbonyl]-2-methyl-1,2,4-triazine-3,5(2H,4H)-dione, methyl 4-amino-3-chloro-6-(4-chloro-2-fluoro-3-methoxyphenyl)-5-fluoro-2-pyridinecarboxylate, 2-methyl-3-(methylsulfonyl)-N-(1-methyl-1H-tetrazol-5-yl)-4-(trifluoromethyl)benzamide and 2-methyl-N-(4-methyl-1,2,5-oxadiazol-3-yl)-3-(methylsulfinyl)-4-(trifluoromethyl)benzamide. Other herbicides also include bioherbicides such as *Alternaria destruens* Simmons, *Colletotrichum* gloeosporiodes (Penz.) Penz. & Sacc., *Drechsiera monoceras* (MTB-951), *Myrothecium verrucaria* (Albertini & Schweinitz) Ditmar: Fries, *Phytophthora palmivora* (Butl.) Butl. and *Puccinia thlaspeos* Schub.

Preferred for better control of undesired vegetation (e.g., lower use rate such as from greater-than-additive effects, broader spectrum of weeds controlled, or enhanced crop safety) or for preventing the development of resistant weeds are mixtures of a compound of this invention with a herbicide selected from the group consisting of atrazine, azimsulfuron, beflubutamid, S-beflubutamide F4050, benzisothiazolinone, carfentrazone-ethyl, chlorimuron-ethyl, chlorsulfuron-methyl, clomazone, clopyralid potassium, cloransulam-methyl, 2-[(2,5-dichlorophenyl)methyl]-4,4-dimethyl-3-isoxazolidinone F9600, ethametsulfuron-methyl, flumetsulam, 4-(4-fluorophenyl)-6-[(2-hydroxy-6-oxo-1-cyclohexen-1-yl)carbonyl]-2-methyl-1,2,4-triazine-3,5-(2H,4H)-dione F9960, flupyrsulfuron-methyl, fluthiacet-methyl, fomesafen, imazethapyr, lenacil, mesotrione, metribuzin, metsulfuron-methyl, pethoxamid, picloram, pyroxasulfone, quinclorac, rimsulfuron, S-metolachlor, sulfentrazone, thifensulfuron-methyl, triflusulfuron-methyl and tribenuron-methyl.

Compounds of this invention can also be used in combination with plant growth regulators such as aviglycine, N-(phenylmethyl)-1H-purin-6-amine, epocholeone, gibberellic acid, gibberellin $A_4$ and $A_7$, harpin protein, mepiquat chloride, prohexadione calcium, prohydrojasmon, sodium nitrophenolate and trinexapac-methyl, and plant growth modifying organisms such as *Bacillus cereus* strain BP01.

General references for agricultural protectants (i.e. herbicides, herbicide safeners, insecticides, fungicides, nematocides, acaricides and biological agents) include *The Pesticide Manual,* 13*th Edition*, C. D. S. Tomlin, Ed., British Crop Protection Council, Farnham, Surrey, U. K., 2003 and *The BioPesticide Manual,* 2nd Edition, L. G. Copping, Ed., British Crop Protection Council, Farnham, Surrey, U. K., 2001.

For embodiments where one or more of these various mixing partners are used, the mixing partners are typically used in the amounts similar to amounts customary when the mixture partners are used alone. More particularly in mixtures, active ingredients are often applied at an application rate between one-half and the full application rate specified on product labels for use of active ingredient alone. These amounts are listed in references such as *The Pesticide Manual* and *The BioPesticide Manual*. The weight ratio of these various mixing partners (in total) to the compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of weeds controlled beyond the spectrum controlled by the compound of Formula 1 alone.

In certain instances, combinations of a compound of this invention with other biologically active (particularly herbicidal) compounds or agents (i.e. active ingredients) can result in a greater-than-additive (i.e. synergistic (enhanced)) effect on weeds and/or a less-than-additive effect (i.e. safening) on crops or other desirable plants. Reducing the quantity of active ingredients released in the environment while ensuring effective pest control is always desirable. Ability to use greater amounts of active ingredients to provide more effective weed control without excessive crop injury is also desirable. When synergism (enhanced effects) of herbicidal active ingredients occurs on weeds at application rates giving agronomically satisfactory levels of weed control, such combinations can be advantageous for reducing crop production cost and decreasing environmental load. When safening of herbicidal active ingredients occurs on crops, such combinations can be advantageous for increasing crop protection by reducing weed competition.

Of note is a combination of a compound of the invention with at least one other herbicidal active ingredient. Of particular note is such a combination where the other herbicidal active ingredient has different site of action from the compound of the invention. In certain instances, a combination with at least one other herbicidal active ingredient having a similar spectrum of control but a different site of action will be particularly advantageous for resistance management. Thus, a composition of the present invention can further comprise (in a herbicidally effective amount) at least one additional herbicidal active ingredient having a similar spectrum of control but a different site of action.

Compounds of this invention can also be used in combination with herbicide safeners such as allidochlor, benoxacor, cloquintocet-mexyl, cumyluron, cyometrinil, cyprosulfonamide, daimuron, dichlormid, dicyclonon, diethatyl, dimepiperate, fenchlorazole-ethyl, fenclorim, flurazole, fluxofenim, furilazole, isoxadifen-ethyl, mefenpyr-diethyl, mephenate, methoxyphenone, naphthalic anhydride (1,8-naphthalic anhydride), oxabetrinil, N-(aminocarbonyl)-2-methylbenzenesulfonamide, N-(aminocarbonyl)-2-fluorobenzenesulfonamide, 1-bromo-4-[(chloromethyl)sulfonyl]benzene (BCS), 4-(dichloroacetyl)-1-oxa-4-azospiro[4.5]decane (MON 4660), 2-(dichloromethyl)-2-methyl-1,3-dioxolane (MG 191), ethyl 1,6-dihydro-1-(2-methoxyphenyl)-6-oxo-2-phenyl-5-pyrimidinecarboxylate, 2-hydroxy-N,N-dimethyl-6-(trifluoromethyl)pyridine-3-carboxamide, and 3-oxo-1-cyclohexen-1-yl 1-(3,4-dimethylphenyl)-1,6-dihydro-6-oxo-2-phenyl-5-pyrimidinecarboxylate, 2,2-dichloro-1-(2,2,5-trimethyl-3-oxazolidinyl)-ethanone and 2-methoxy-N-[[4-[[(methylamino)carbonyl]amino]phenyl]sulfonyl]-benzamide to increase safety to certain crops. Antidotally effective amounts of the herbicide safeners can be applied at the same time as the compounds of this invention, or applied as seed treatments. Therefore an aspect of the present invention relates to a herbicidal mixture comprising a compound of this invention and an antidotally effective amount of a herbicide safener. Seed treatment is particularly useful for selective weed control, because it physically restricts antidoting to the crop plants. Therefore a particularly useful embodiment of the present invention is a method for selectively controlling the growth of undesired vegetation in a crop comprising contacting the locus of the crop with a herbicidally effective amount of a compound of this invention wherein seed from which the crop is grown is treated with an antidotally effective amount of safener. Antidotally effective amounts of safeners can be easily determined by one skilled in the art through simple experimentation.

Compounds of the invention cans also be mixed with: (1) polynucleotides including but not limited to DNA, RNA, and/or chemically modified nucleotides influencing the amount of a particular target through down regulation, interference, suppression or silencing of the genetically derived transcript that render a herbicidal effect; or (2) polynucleotides including but not limited to DNA, RNA, and/or chemically modified nucleotides influencing the amount of a particular target through down regulation, interference, suppression or silencing of the genetically derived transcript that render a safening effect.

Of note is a composition comprising a compound of the invention (in a herbicidally effective amount), at least one additional active ingredient selected from the group consisting of other herbicides and herbicide safeners (in an effective amount), and at least one component selected from the group consisting of surfactants, solid diluents and liquid diluents.

Table A1 lists specific combinations of a Component (a) with Component (b) illustrative of the mixtures, compositions and methods of the present invention. Compound 1 (i.e. "Cmpd. No." stands for "Compound Number") in the Component (a) column is identified in Index Table A. The second column of Table A1 lists the specific Component (b) compound (e.g., "2,4-D" in the first line). The third, fourth and fifth columns of Table A1 lists ranges of weight ratios for rates at which the Component (a) compound is typically applied to a field-grown crop relative to Component (b) (i.e. (a):(b)). Thus, for example, the first line of Table A1 specifically discloses the combination of Component (a) (i.e. Compound 1 in Index Table A) with 2,4-D is typically applied in a weight ratio between 1:192-6:1. The remaining lines of Table A1 are to be construed similarly.

TABLE A1

| Component (a) (Cmpd. No.) | Component (b) | Typical Weight Ratio | More Typical Weight Ratio | Most Typical Weight Ratio |
| --- | --- | --- | --- | --- |
| 1 | 2,4-D | 1:192-6:1 | 1:64-2:1 | 1:24-1:3 |
| 1 | Acetochlor | 1:768-2:1 | 1:256-1:2 | 1:96-1:11 |
| 1 | Acifluorfen | 1:96-12:1 | 1:32-4:1 | 1:12-1:2 |
| 1 | Aclonifen | 1:857-2:1 | 1:285-1:3 | 1:107-1:12 |
| 1 | Alachlor | 1:768-2:1 | 1:256-1:2 | 1:96-1:11 |
| 1 | Ametryn | 1:384-3:1 | 1:128-1:1 | 1:48-1:6 |
| 1 | Amicarbazone | 1:192-6:1 | 1:64-2:1 | 1:24-1:3 |
| 1 | Amidosulfuron | 1:6-168:1 | 1:2-56:1 | 1:1-11:1 |
| 1 | Aminocyclopyrachlor | 1:48-24:1 | 1:16-8:1 | 1:6-2:1 |
| 1 | Aminopyralid | 1:20-56:1 | 1:6-19:1 | 1:2-4:1 |
| 1 | Amitrole | 1:768-2:1 | 1:256-1:2 | 1:96-1:11 |
| 1 | Anilofos | 1:96-12:1 | 1:32-4:1 | 1:12-1:2 |
| 1 | Asulam | 1:960-2:1 | 1:320-1:3 | 1:120-1:14 |
| 1 | Atrazine | 1:192-6:1 | 1:64-2:1 | 1:24-1:3 |
| 1 | Azimsulfuron | 1:6-168:1 | 1:2-56:1 | 1:1-11:1 |
| 1 | Beflubutamid | 1:342-4:1 | 1:114-2:1 | 1:42-1:5 |
| 1 | S-Beflubutamid | 1:171-4:0.5 | 1:57-2:0.5 | 1:21-1:2.5 |
| 1 | Benfuresate | 1:617-2:1 | 1:205-1:2 | 1:77-1:9 |
| 1 | Bensulfuron-methyl | 1:25-45:1 | 1:8-15:1 | 1:3-3:1 |
| 1 | Bentazone | 1:192-6:1 | 1:64-2:1 | 1:24-1:3 |
| 1 | Benzobicyclon | 1:85-14:1 | 1:28-5:1 | 1:10-1:2 |
| 1 | Benzofenap | 1:257-5:1 | 1:85-2:1 | 1:32-1:4 |

TABLE A1-continued

| Component (a) (Cmpd. No.) | Component (b) | Typical Weight Ratio | More Typical Weight Ratio | Most Typical Weight Ratio |
|---|---|---|---|---|
| 1 | Bicyclopyrone | 1:42-27:1 | 1:14-9:1 | 1:5-2:1 |
| 1 | Bifenox | 1:257-5:1 | 1:85-2:1 | 1:32-1:4 |
| 1 | Bispyribac-sodium | 1:10-112:1 | 1:3-38:1 | 1:1-7:1 |
| 1 | Bromacil | 1:384-3:1 | 1:128-1:1 | 1:48-1:6 |
| 1 | Bromobutide | 1:384-3:1 | 1:128-1:1 | 1:48-1:6 |
| 1 | Bromoxynil | 1:96-12:1 | 1:32-4:1 | 1:12-1:2 |
| 1 | Butachlor | 1:768-2:1 | 1:256-1:2 | 1:96-1:11 |
| 1 | Butafenacil | 1:42-27:1 | 1:14-9:1 | 1:5-2:1 |
| 1 | Butylate | 1:1542-1:2 | 1:514-1:5 | 1:192-1:22 |
| 1 | Carfenstrole | 1:192-6:1 | 1:64-2:1 | 1:24-1:3 |
| 1 | Carfentrazone-ethyl | 1:128-9:1 | 1:42-3:1 | 1:16-1:2 |
| 1 | Chlorimuron-ethyl | 1:8-135:1 | 1:2-45:1 | 1:1-9:1 |
| 1 | Chlorotoluron | 1:768-2:1 | 1:256-1:2 | 1:96-1:11 |
| 1 | Chlorsulfuron | 1:6-168:1 | 1:2-56:1 | 1:1-11:1 |
| 1 | Cincosulfuron | 1:17-68:1 | 1:5-23:1 | 1:2-5:1 |
| 1 | Cinidon-ethyl | 1:384-3:1 | 1:128-1:1 | 1:48-1:6 |
| 1 | Cinmethylin | 1:34-34:1 | 1:11-12:1 | 1:4-3:1 |
| 1 | Clacyfos | 1:34-34:1 | 1:11-12:1 | 1:4-3:1 |
| 1 | Clethodim | 1:48-24:1 | 1:16-8:1 | 1:6-2:1 |
| 1 | Clodinafop-propargyl | 1:20-56:1 | 1:6-19:1 | 1:2-4:1 |
| 1 | Clomazone | 1:384-3:1 | 1:128-1:1 | 1:48-1:6 |
| 1 | Clomeprop | 1:171-7:1 | 1:57-3:1 | 1:21-1:3 |
| 1 | Clopyralid | 1:192-6:1 | 1:64-2:1 | 1:24-1:3 |
| 1 | Cloransulam-methyl | 1:12-96:1 | 1:4-32:1 | 1:1-6:1 |
| 1 | Cumyluron | 1:384-3:1 | 1:128-1:1 | 1:48-1:6 |
| 1 | Cyanazine | 1:384-3:1 | 1:128-1:1 | 1:48-1:6 |
| 1 | Cyclopyrimorate | 1:17-68:1 | 1:5-23:1 | 1:2-5:1 |
| 1 | Cyclosulfamuron | 1:17-68:1 | 1:5-23:1 | 1:2-5:1 |
| 1 | Cycloxydim | 1:96-12:1 | 1:32-4:1 | 1:12-1:2 |
| 1 | Cyhalofop | 1:25-45:1 | 1:8-15:1 | 1:3-3:1 |
| 1 | Daimuron | 1:192-6:1 | 1:64-2:1 | 1:24-1:3 |
| 1 | Desmedipham | 1:322-4:1 | 1:107-2:1 | 1:40-1:5 |
| 1 | Dicamba | 1:192-6:1 | 1:64-2:1 | 1:24-1:3 |
| 1 | Dichlobenil | 1:1371-1:2 | 1:457-1:4 | 1:171-1:20 |
| 1 | Dichlorprop | 1:925-2:1 | 1:308-1:3 | 1:115-1:13 |
| 1 | Diclofop-methyl | 1:384-3:1 | 1:128-1:1 | 1:48-1:6 |
| 1 | Diclosulam | 1:10-112:1 | 1:3-38:1 | 1:1-7:1 |
| 1 | Difenzoquat | 1:288-4:1 | 1:96-2:1 | 1:36-1:4 |
| 1 | Diflufenican | 1:857-2:1 | 1:285-1:3 | 1:107-1:12 |
| 1 | Diflufenzopyr | 1:12-96:1 | 1:4-32:1 | 1:1-6:1 |
| 1 | Dimethachlor | 1:768-2:1 | 1:256-1:2 | 1:96-1:11 |
| 1 | Dimethametryn | 1:192-6:1 | 1:64-2:1 | 1:24-1:3 |
| 1 | Dimethenamid-P | 1:384-3:1 | 1:128-1:1 | 1:48-1:6 |
| 1 | Dithiopyr | 1:192-6:1 | 1:64-2:1 | 1:24-1:3 |
| 1 | Diuron | 1:384-3:1 | 1:128-1:1 | 1:48-1:6 |
| 1 | EPTC | 1:768-2:1 | 1:256-1:2 | 1:96-1:11 |
| 1 | Esprocarb | 1:1371-1:2 | 1:457-1:4 | 1:171-1:20 |
| 1 | Ethalfluralin | 1:384-3:1 | 1:128-1:1 | 1:48-1:6 |
| 1 | Ethametsulfuron-methyl | 1:17-68:1 | 1:5-23:1 | 1:2-5:1 |
| 1 | Ethoxyfen | 1:8-135:1 | 1:2-45:1 | 1:1-9:1 |
| 1 | Ethoxysulfuron | 1:20-56:1 | 1:6-19:1 | 1:2-4:1 |
| 1 | Etobenzanid | 1:257-5:1 | 1:85-2:1 | 1:32-1:4 |
| 1 | Fenoxaprop-ethyl | 1:120-10:1 | 1:40-4:1 | 1:15-1:2 |
| 1 | Fenoxasulfone | 1:85-14:1 | 1:28-5:1 | 1:10-1:2 |
| 1 | Fenquinotrione | 1:17-68:1 | 1:5-23:1 | 1:2-5:1 |
| 1 | Fentrazamide | 1:17-68:1 | 1:5-23:1 | 1:2-5:1 |
| 1 | Flazasulfuron | 1:17-68:1 | 1:5-23:1 | 1:2-5:1 |
| 1 | Florasulam | 1:2-420:1 | 1:1-140:1 | 2:1-27:1 |
| 1 | Fluazifop-butyl | 1:192-6:1 | 1:64-2:1 | 1:24-1:3 |
| 1 | Flucarbazone | 1:8-135:1 | 1:2-45:1 | 1:1-9:1 |
| 1 | Flucetosulfuron | 1:8-135:1 | 1:2-45:1 | 1:1-9:1 |
| 1 | Flufenacet | 1:257-5:1 | 1:85-2:1 | 1:32-1:4 |
| 1 | Flumetsulam | 1:24-48:1 | 1:8-16:1 | 1:3-3:1 |
| 1 | Flumiclorac-pentyl | 1:10-112:1 | 1:3-38:1 | 1:1-7:1 |
| 1 | Flumioxazin | 1:25-45:1 | 1:8-15:1 | 1:3-3:1 |
| 1 | Fluometuron | 1:384-3:1 | 1:128-1:1 | 1:48-1:6 |
| 1 | Flupyrsulfuron-methyl | 1:3-336:1 | 1:1-112:1 | 2:1-21:1 |
| 1 | Fluridone | 1:384-3:1 | 1:128-1:1 | 1:48-1:6 |
| 1 | Fluroxypyr | 1:96-12:1 | 1:32-4:1 | 1:12-1:2 |
| 1 | Flurtamone | 1:857-2:1 | 1:285-1:3 | 1:107-1:12 |
| 1 | Fluthiacet-methyl | 1:48-42:1 | 1:16-14:1 | 1:3-3:1 |
| 1 | Fomesafen | 1:96-12:1 | 1:32-4:1 | 1:12-1:2 |
| 1 | Foramsulfuron | 1:13-84:1 | 1:4-28:1 | 1:1-6:1 |
| 1 | Glufosinate | 1:288-4:1 | 1:96-2:1 | 1:36-1:4 |
| 1 | Glyphosate | 1:288-4:1 | 1:96-2:1 | 1:36-1:4 |
| 1 | Halosulfuron-methyl | 1:17-68:1 | 1:5-23:1 | 1:2-5:1 |
| 1 | Halauxifen | 1:20-56:1 | 1:6-19:1 | 1:2-4:1 |

TABLE A1-continued

| Component (a) (Cmpd. No.) | Component (b) | Typical Weight Ratio | More Typical Weight Ratio | Most Typical Weight Ratio |
|---|---|---|---|---|
| 1 | Halauxifen methyl | 1:20-56:1 | 1:6-19:1 | 1:2-4:1 |
| 1 | Haloxyfop-methyl | 1:34-34:1 | 1:11-12:1 | 1:4-3:1 |
| 1 | Hexazinone | 1:192-6:1 | 1:64-2:1 | 1:24-1:3 |
| 1 | Hydantocidin | 1:1100-16:1 | 1:385-8:1 | 1:144-4:1 |
| 1 | Imazamox | 1:13-84:1 | 1:4-28:1 | 1:1-6:1 |
| 1 | Imazapic | 1:20-56:1 | 1:6-19:1 | 1:2-4:1 |
| 1 | Imazapyr | 1:85-14:1 | 1:28-5:1 | 1:10-1:2 |
| 1 | Imazaquin | 1:34-34:1 | 1:11-12:1 | 1:4-3:1 |
| 1 | Imazethabenz-methyl | 1:171-7:1 | 1:57-3:1 | 1:21-1:3 |
| 1 | Imazethapyr | 1:24-48:1 | 1:8-16:1 | 1:3-3:1 |
| 1 | Imazosulfuron | 1:27-42:1 | 1:9-14:1 | 1:3-3:1 |
| 1 | Indanofan | 1:342-4:1 | 1:114-2:1 | 1:42-1:5 |
| 1 | Indaziflam | 1:25-45:1 | 1:8-15:1 | 1:3-3:1 |
| 1 | Iodosulfuron-methyl | 1:3-336:1 | 1:1-112:1 | 2:1-21:1 |
| 1 | Ioxynil | 1:192-6:1 | 1:64-2:1 | 1:24-1:3 |
| 1 | Ipfencarbazone | 1:85-14:1 | 1:28-5:1 | 1:10-1:2 |
| 1 | Isoproturon | 1:384-3:1 | 1:128-1:1 | 1:48-1:6 |
| 1 | Isoxaben | 1:288-4:1 | 1:96-2:1 | 1:36-1:4 |
| 1 | Isoxaflutole | 1:60-20:1 | 1:20-7:1 | 1:7-2:1 |
| 1 | Lactofen | 1:42-27:1 | 1:14-9:1 | 1:5-2:1 |
| 1 | Lenacil | 1:384-3:1 | 1:128-1:1 | 1:48-1:6 |
| 1 | Linuron | 1:384-3:1 | 1:128-1:1 | 1:48-1:6 |
| 1 | MCPA | 1:192-6:1 | 1:64-2:1 | 1:24-1:3 |
| 1 | MCPB | 1:288-4:1 | 1:96-2:1 | 1:36-1:4 |
| 1 | Mecoprop | 1:768-2:1 | 1:256-1:2 | 1:96-1:11 |
| 1 | Mefenacet | 1:384-3:1 | 1:128-1:1 | 1:48-1:6 |
| 1 | Mefluidide | 1:192-6:1 | 1:64-2:1 | 1:24-1:3 |
| 1 | Mesosulfuron-methyl | 1:5-224:1 | 1:1-75:1 | 1:1-14:1 |
| 1 | Mesotrione | 1:42-27:1 | 1:14-9:1 | 1:5-2:1 |
| 1 | Metamifop | 1:42-27:1 | 1:14-9:1 | 1:5-2:1 |
| 1 | Metazachlor | 1:384-3:1 | 1:128-1:1 | 1:48-1:6 |
| 1 | Metazosulfuron | 1:25-45:1 | 1:8-15:1 | 1:3-3:1 |
| 1 | Methabenzthiazuron | 1:768-2:1 | 1:256-1:2 | 1:96-1:11 |
| 1 | Metolachlor | 1:768-2:1 | 1:256-1:2 | 1:96-1:11 |
| 1 | Metosulam | 1:8-135:1 | 1:2-45:1 | 1:1-9:1 |
| 1 | Metribuzin | 1:192-6:1 | 1:64-2:1 | 1:24-1:3 |
| 1 | Metsulfuron-methyl | 1:2-560:1 | 1:1-187:1 | 3:1-35:1 |
| 1 | Molinate | 1:1028-2:1 | 1:342-1:3 | 1:128-1:15 |
| 1 | Napropamide | 1:384-3:1 | 1:128-1:1 | 1:48-1:6 |
| 1 | Napropamide-M | 1:192-6:1 | 1:64-2:1 | 1:24-1:3 |
| 1 | Naptalam | 1:192-6:1 | 1:64-2:1 | 1:24-1:3 |
| 1 | Nicosulfuron | 1:12-96:1 | 1:4-32:1 | 1:1-6:1 |
| 1 | Norflurazon | 1:1152-1:1 | 1:384-1:3 | 1:144-1:16 |
| 1 | Orbencarb | 1:1371-1:2 | 1:457-1:4 | 1:171-1:20 |
| 1 | Orthosulfamuron | 1:20-56:1 | 1:6-19:1 | 1:2-4:1 |
| 1 | Oryzalin | 1:514-3:1 | 1:171-1:2 | 1:64-1:8 |
| 1 | Oxadiargyl | 1:384-3:1 | 1:128-1:1 | 1:48-1:6 |
| 1 | Oxadiazon | 1:548-3:1 | 1:182-1:2 | 1:68-1:8 |
| 1 | Oxasulfuron | 1:27-42:1 | 1:9-14:1 | 1:3-3:1 |
| 1 | Oxaziclomefone | 1:42-27:1 | 1:14-9:1 | 1:5-2:1 |
| 1 | Oxyfluorfen | 1:384-3:1 | 1:128-1:1 | 1:48-1:6 |
| 1 | Paraquat | 1:192-6:1 | 1:64-2:1 | 1:24-1:3 |
| 1 | Pendimethalin | 1:384-3:1 | 1:128-1:1 | 1:48-1:6 |
| 1 | Penoxsulam | 1:10-112:1 | 1:3-38:1 | 1:1-7:1 |
| 1 | Penthoxamid | 1:384-3:1 | 1:128-1:1 | 1:48-1:6 |
| 1 | Pentoxazone | 1:102-12:1 | 1:34-4:1 | 1:12-1:2 |
| 1 | Phenmedipham | 1:102-12:1 | 1:34-4:1 | 1:12-1:2 |
| 1 | Picloram | 1:96-12:1 | 1:32-4:1 | 1:12-1:2 |
| 1 | Picolinafen | 1:34-34:1 | 1:11-12:1 | 1:4-3:1 |
| 1 | Pinoxaden | 1:25-45:1 | 1:8-15:1 | 1:3-3:1 |
| 1 | Pretilachlor | 1:192-6:1 | 1:64-2:1 | 1:24-1:3 |
| 1 | Primisulfuron-methyl | 1:8-135:1 | 1:2-45:1 | 1:1-9:1 |
| 1 | Prodiamine | 1:384-3:1 | 1:128-1:1 | 1:48-1:6 |
| 1 | Profoxydim | 1:42-27:1 | 1:14-9:1 | 1:5-2:1 |
| 1 | Prometryn | 1:384-3:1 | 1:128-1:1 | 1:48-1:6 |
| 1 | Propachlor | 1:1152-1:1 | 1:384-1:3 | 1:144-1:16 |
| 1 | Propanil | 1:384-3:1 | 1:128-1:1 | 1:48-1:6 |
| 1 | Propaquizafop | 1:48-24:1 | 1:16-8:1 | 1:6-2:1 |
| 1 | Propoxycarbazone | 1:17-68:1 | 1:5-23:1 | 1:2-5:1 |
| 1 | Propyrisulfuron | 1:17-68:1 | 1:5-23:1 | 1:2-5:1 |
| 1 | Propyzamide | 1:384-3:1 | 1:128-1:1 | 1:48-1:6 |
| 1 | Prosulfocarb | 1:1200-1:2 | 1:400-1:4 | 1:150-1:17 |
| 1 | Prosulfuron | 1:6-168:1 | 1:2-56:1 | 1:1-11:1 |
| 1 | Pyraclonil | 1:42-27:1 | 1:14-9:1 | 1:5-2:1 |
| 1 | Pyraflufen-ethyl | 1:5-224:1 | 1:1-75:1 | 1:1-14:1 |
| 1 | Pyrasulfotole | 1:13-84:1 | 1:4-28:1 | 1:1-6:1 |
| 1 | Pyrazolynate | 1:857-2:1 | 1:285-1:3 | 1:107-1:12 |

TABLE A1-continued

| Component (a) (Cmpd. No.) | Component (b) | Typical Weight Ratio | More Typical Weight Ratio | Most Typical Weight Ratio |
|---|---|---|---|---|
| 1 | Pyrazosulfuron-ethyl | 1:10-112:1 | 1:3-38:1 | 1:1-7:1 |
| 1 | Pyrazoxyfen | 1:5-224:1 | 1:1-75:1 | 1:1-14:1 |
| 1 | Pyribenzoxim | 1:10-112:1 | 1:3-38:1 | 1:1-7:1 |
| 1 | Pyributicarb | 1:384-3:1 | 1:128-1:1 | 1:48-1:6 |
| 1 | Pyridate | 1:288-4:1 | 1:96-2:1 | 1:36-1:4 |
| 1 | Pyriftalid | 1:10-112:1 | 1:3-38:1 | 1:1-7:1 |
| 1 | Pyriminobac-methyl | 1:20-56:1 | 1:6-19:1 | 1:2-4:1 |
| 1 | Pyrimisulfan | 1:17-68:1 | 1:5-23:1 | 1:2-5:1 |
| 1 | Pyrithiobac | 1:24-48:1 | 1:8-16:1 | 1:3-3:1 |
| 1 | Pyroxasulfone | 1:85-14:1 | 1:28-5:1 | 1:10-1:2 |
| 1 | Pyroxsulam | 1:5-224:1 | 1:1-75:1 | 1:1-14:1 |
| 1 | Quinclorac | 1:192-6:1 | 1:64-2:1 | 1:24-1:3 |
| 1 | Quizalofop-ethyl | 1:42-27:1 | 1:14-9:1 | 1:5-2:1 |
| 1 | Rimsulfuron | 1:13-84:1 | 1:4-28:1 | 1:1-6:1 |
| 1 | Saflufenacil | 1:25-45:1 | 1:8-15:1 | 1:3-3:1 |
| 1 | Sethoxydim | 1:96-12:1 | 1:32-4:1 | 1:12-1:2 |
| 1 | Simazine | 1:384-3:1 | 1:128-1:1 | 1:48-1:6 |
| 1 | Sulcotrione | 1:120-10:1 | 1:40-4:1 | 1:15-1:2 |
| 1 | Sulfentrazone | 1:147-8:1 | 1:49-3:1 | 1:18-1:3 |
| 1 | Sulfometuron-methyl | 1:34-34:1 | 1:11-12:1 | 1:4-3:1 |
| 1 | Sulfosulfuron | 1:8-135:1 | 1:2-45:1 | 1:1-9:1 |
| 1 | Tebuthiuron | 1:384-3:1 | 1:128-1:1 | 1:48-1:6 |
| 1 | Tefuryltrione | 1:42-27:1 | 1:14-9:1 | 1:5-2:1 |
| 1 | Tembotrione | 1:31-37:1 | 1:10-13:1 | 1:3-3:1 |
| 1 | Tepraloxydim | 1:25-45:1 | 1:8-15:1 | 1:3-3:1 |
| 1 | Terbacil | 1:288-4:1 | 1:96-2:1 | 1:36-1:4 |
| 1 | Terbuthylazine | 1:857-2:1 | 1:285-1:3 | 1:107-1:12 |
| 1 | Terbutryn | 1:192-6:1 | 1:64-2:1 | 1:24-1:3 |
| 1 | Thenylchlor | 1:85-14:1 | 1:28-5:1 | 1:10-1:2 |
| 1 | Thiazopyr | 1:384-3:1 | 1:128-1:1 | 1:48-1:6 |
| 1 | Thiencarbazone | 1:3-336:1 | 1:1-112:1 | 2:1-21:1 |
| 1 | Thifensulfuron-methyl | 1:5-224:1 | 1:1-75:1 | 1:1-14:1 |
| 1 | Tiafenacil | 1:17-68:1 | 1:5-23:1 | 1:2-5:1 |
| 1 | Thiobencarb | 1:768-2:1 | 1:256-1:2 | 1:96-1:11 |
| 1 | Tolpyralate | 1:31-37:1 | 1:10-13:1 | 1:3-3:1 |
| 1 | Topramzone | 1:6-168:1 | 1:2-56:1 | 1:1-11:1 |
| 1 | Tralkoxydim | 1:68-17:1 | 1:22-6:1 | 1:8-2:1 |
| 1 | Triafamone | 1:2-420:1 | 1:1-140:1 | 2:1-27:1 |
| 1 | Triallate | 1:768-2:1 | 1:256-1:2 | 1:96-1:11 |
| 1 | Triasulfuron | 1:5-224:1 | 1:1-75:1 | 1:1-14:1 |
| 1 | Triaziflam | 1:171-7:1 | 1:57-3:1 | 1:21-1:3 |
| 1 | Tribenuron-methyl | 1:3-336:1 | 1:1-112:1 | 2:1-21:1 |
| 1 | Triclopyr | 1:192-6:1 | 1:64-2:1 | 1:24-1:3 |
| 1 | Trifloxysulfuron | 1:2-420:1 | 1:1-140:1 | 2:1-27:1 |
| 1 | Trifludimoxazin | 1:25-45:1 | 1:8-15:1 | 1:3-3:1 |
| 1 | Trifluralin | 1:288-4:1 | 1:96-2:1 | 1:36-1:4 |
| 1 | Triflusulfuron-methyl | 1:17-68:1 | 1:5-23:1 | 1:2-5:1 |
| 1 | Tritosulfuron | 1:13-84:1 | 1:4-28:1 | 1:1-6:1 |

Table A2 is constructed the same as Table A1 above except that entries below the "Component (a)" column heading are replaced with the respective Component (a) Column Entry shown below. Compound 2 in the Component (a) column is identified in Index Table A. Thus, for example, in Table A2 the entries below the "Component (a)" column heading all recite "Compound 2" (i.e. Compound 2 identified in Index Table A), and the first line below the column headings in Table A2 specifically discloses a mixture of Compound 2 with 2,4-D. Tables A3 through A11 are constructed similarly.

| Table Number | Component (a) Column Entries |
|---|---|
| A2 | Compound 2 |
| A3 | Compound 3 |
| A4 | Compound 4 |
| A5 | Compound 5 |
| A6 | Compound 6 |
| A7 | Compound 7 |
| A8 | Compound 8 |
| A9 | Compound 9 |

Preferred for better control of undesired vegetation (e.g., lower use rate such as from synergism (enhanced effects), broader spectrum of weeds controlled, or enhanced crop safety) or for preventing the development of resistant weeds are mixtures of a compound of Formula 1 with a herbicide selected from the group consisting of chlorimuron-ethyl, nicosulfuron, mesotrione, thifensulfuron-methyl, flupyrsulfuron-methyl, tribenuron, pyroxasulfone, pinoxaden, tembotrione, pyroxsulam, metolachlor and S-metolachlor.

The following Tests demonstrate the control efficacy of the compounds of this invention against specific weeds. The weed control afforded by the compounds is not limited, however, to these species. See Index Tables A for compound descriptions. The following abbreviations are used in the Index Table which follow: The abbreviation "Cmpd. No."

stands for "Compound Number". The abbreviation "Ex." stands for "Example" and is followed by a number indicating in which example the compound is prepared. Mass spectral data are reported with an estimated precision within ±0.5 Da as the molecular weight of the highest isotopic abundance parent ion (M+1) formed by addition of H⁺ (molecular weight of 1) to the molecule observed by using atmospheric pressure chemical ionization (AP+).

and were in the one- to two-leaf stage for the postemergence treatment. Treated plants and untreated controls were maintained in a greenhouse for approximately 10 d, after which time all treated plants were compared to untreated controls and visually evaluated for injury. Plant response ratings, summarized in Table A, are based on a 0 to 100 scale where 0 is no effect and 100 is complete control. A dash (-) response means no test result.

INDEX TABLE A

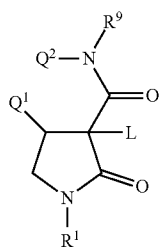

| Cmpd. No. | $Q^1$ | $Q^2$ | L | $R^9$ | L |
|---|---|---|---|---|---|
| 1 (Ex. 3) | Ph(4-CF₃) | Ph(2,3-di-F) | L-1 | H | $R^A$ = CH₃ |
| 2 (Ex. 2) | Ph(4-CF₃) | Ph(2,3-di-F) | L-3 | H | $R^B$, $R^C$ = H; $R^F$ = C(=O)CH₃ |
| 3 | Ph(4-CF₃) | Ph(2,3-di-F) | L-1 | | —C(=O)C(CH₃)₂C(=O)— |
| 4 (Ex. 1) (cis) | Ph(4-CF₃) | Ph(2,3-di-F) | L-3 | H | $R^B$; $R^C$ = H; $R^F$ = H |
| 5 (Ex. 1) (trans) | Ph(4-CF₃) | Ph(2,3-di-F) | L-3 | H | $R^B$; $R^C$ = H; $R^F$ = H |
| 6 (trans) | Ph(4-CF₃) | Ph(2,3-di-F) | L-3 | H | $R^B$, $R^C$ = H; $R^F$ = C(=O)(CH₂)₃C(=O)OH |
| 7 | Ph(4-CF₃) | Ph(2,3-di-F) | L-1 | H | $R^A$ = N(H)CH₂CH₃ |
| 8 | Ph(4-CF₃) | Ph(2,3-di-F) | L-1 | H | $R^A$ = N(H)CH(CH₃)₂ |
| 9 | Ph(4-CF₃) | Ph(2,3-di-F) | L-2 | H | $R^B$; $R^C$ = H; $R^D$ = CH₃; $R^E$ is CH₃ |

INDEX TABLE B

| Cmpd. No. | Mass (M+) |
|---|---|
| 1 | * |
| 2 | * |
| 3 | 495 (M + 1) |
| 4 | 429 (M + 1) |
| 5 | 429 (M + 1) |
| 6 | 529 (M + 1) |
| 7 | 470 (M + 1) |
| 8 | 484 (M + 1) |
| 9 | 454 (M − 1) |

* See Synthesis Example for ¹H NMR data

Biological Examples of the Invention

Test A

Seeds of plant species selected from barnyardgrass (*Echinochloa crus-galli*), kochia (*Kochia scoparia*), ragweed (common ragweed, *Ambrosia elatior*), ryegrass, Italian (Italian ryegrass, *Lolium multiflorum*), foxtail, green (green foxtail, *Setaria viridis*), and pigweed (*Amaranthus retroflexus*) were planted into a blend of loam soil and sand and treated preemergence with a directed soil spray using test chemicals formulated in a non-phytotoxic solvent mixture which included a surfactant.

At the same time, plants selected from these weed species and also wheat (*Triticum aestivum*), corn (*Zea mays*), blackgrass (*Alopecurus myosuroides*), and galium (catchweed bedstraw, *Galium aparine*) were planted in pots containing the same blend of loam soil and sand and treated with postemergence applications of test chemicals formulated in the same manner. Plants ranged in height from 2 to 10 cm

TABLE A

| | Postemergence | | | | | | | | |
|---|---|---|---|---|---|---|---|---|---|
| | Compounds | | | | | | | | |
| | 1 | 2 | 3 | 4 | 5 | 6 | 7 | 8 | 9 |
| 125 g ai/ha | | | | | | | | | |
| Barnyardgrass | 90 | 50 | 70 | 60 | 80 | 50 | 10 | 0 | 90 |
| Blackgrass | 50 | 10 | 30 | 40 | 30 | 0 | 0 | 0 | 60 |
| Corn | 80 | 40 | 80 | 50 | 60 | 0 | 0 | 0 | 50 |
| Foxtail, Green | 90 | 70 | 60 | 60 | 80 | 20 | 20 | 0 | 90 |
| Galium | 60 | 40 | 50 | 40 | 40 | 0 | 30 | 0 | 60 |
| Kochia | 70 | 40 | 60 | 60 | 70 | 0 | 0 | 0 | 70 |
| Pigweed | 80 | 40 | 60 | 70 | 50 | 0 | 30 | 0 | 80 |
| Ragweed | 40 | 40 | 40 | 0 | 40 | 0 | 0 | 0 | 30 |
| Ryegrass, Italian | 80 | 50 | 50 | 50 | 50 | 40 | 10 | 0 | 60 |
| Wheat | 50 | 20 | 40 | 20 | 30 | 10 | 0 | 0 | 60 |
| 31 g ai/ha | | | | | | | | | |
| Barnyardgrass | 70 | 0 | 40 | 0 | 30 | 0 | 0 | 0 | 70 |
| Blackgrass | 0 | 0 | 20 | 0 | 0 | 0 | 0 | 0 | 50 |
| Corn | 20 | 0 | 10 | 0 | 0 | 0 | 0 | 0 | 40 |
| Foxtail, Green | 50 | 20 | 0 | 10 | 30 | 0 | 0 | 0 | 50 |
| Galium | 50 | 0 | 40 | 20 | 40 | 0 | 0 | 0 | 60 |
| Kochia | 20 | 0 | 0 | 0 | 30 | 0 | 0 | 0 | 50 |
| Pigweed | 30 | 20 | 40 | 30 | 30 | 0 | 10 | 0 | 30 |
| Ragweed | 0 | 0 | 0 | 0 | 0 | 0 | 0 | 0 | 30 |
| Ryegrass, Italian | 60 | 20 | 40 | 0 | 20 | 0 | 0 | 0 | 50 |
| Wheat | 20 | 0 | 0 | 0 | 0 | 0 | 0 | 0 | 30 |

TABLE A-continued

Preemergence

| | \multicolumn{9}{c}{Compounds} |
| --- | --- | --- | --- | --- | --- | --- | --- | --- | --- |
| | 1 | 2 | 3 | 4 | 5 | 6 | 7 | 8 | 9 |
| 125 g ai/ha | | | | | | | | | |
| Barnyardgrass | 90 | 80 | 90 | 90 | 90 | 50 | 70 | 0 | 90 |
| Foxtail, Green | 90 | 90 | 90 | 90 | 90 | 80 | 80 | 0 | 90 |
| Kochia | 80 | 50 | 50 | 40 | 60 | 0 | 0 | 0 | 70 |
| Pigweed | 90 | 80 | 100 | 90 | 60 | 0 | 10 | 0 | 80 |
| Ragweed | 70 | 30 | 20 | 0 | 60 | 0 | 0 | 0 | 60 |
| Ryegrass, Italian | 60 | 10 | 40 | 50 | 80 | 30 | 0 | 0 | 80 |
| 31 g ai/ha | | | | | | | | | |
| Barnyardgrass | 80 | 50 | 80 | 30 | 80 | 10 | 0 | 0 | 90 |
| Foxtail, Green | 90 | 60 | 90 | 50 | 70 | 30 | 0 | 0 | 90 |
| Kochia | 40 | 20 | 0 | 0 | 0 | 0 | 0 | 0 | 30 |
| Pigweed | 50 | 20 | 20 | 0 | 0 | 0 | 0 | 0 | 70 |
| Ragweed | 20 | 0 | 0 | 0 | 0 | 0 | 0 | 0 | 0 |
| Ryegrass, Italian | 30 | 0 | 20 | 0 | 10 | 0 | 0 | 0 | 60 |

Test B

Plant species in the flooded paddy test selected from rice (*Oryza sativa*), sedge, umbrella (small-flower umbrella sedge, *Cyperus difformis*), ducksalad (*Heteranthera limosa*), and barnyardgrass (*Echinochloa crus-galli*) were grown to the 2-leaf stage for testing. At time of treatment, test pots were flooded to 3 cm above the soil surface, treated by application of test compounds directly to the paddy water, and then maintained at that water depth for the duration of the test. Treated plants and controls were maintained in a greenhouse for 13 to 15 d, after which time all species were compared to controls and visually evaluated. Plant response ratings, summarized in Table B, are based on a scale of 0 to 100 where 0 is no effect and 100 is complete control. A dash (-) response means no test result.

TABLE B

| | \multicolumn{9}{c}{Compounds} |
| --- | --- | --- | --- | --- | --- | --- | --- | --- | --- |
| 250 g ai/ha | 1 | 2 | 3 | 4 | 5 | 6 | 7 | 8 | 9 |
| Flood | | | | | | | | | |
| Barnyardgrass | 70 | 65 | 45 | 50 | 65 | 60 | 0 | 0 | 65 |
| Ducksalad | 90 | 95 | 80 | 95 | 90 | 85 | 75 | 0 | 95 |
| Rice | 0 | 30 | 10 | 0 | 25 | 20 | 30 | 0 | 0 |
| Sedge, Umbrella | 0 | 0 | 0 | 0 | 0 | 0 | 0 | 0 | 0 |

What is claimed is:

1. A compound selected from Formula 1, N-oxides, and salts thereof

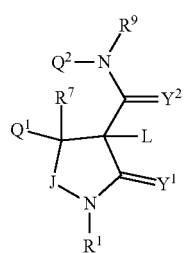

wherein
L is selected from

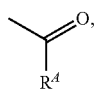

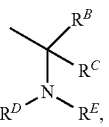

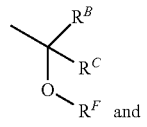

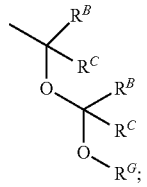

$R^A$ is $C_1$-$C_7$ alkyl, $C_1$-$C_7$ haloalkyl, $C_3$-$C_9$ cycloalkyl, $C_3$-$C_9$ halocycloalkyl, $C_1$-$C_7$ alkoxy, $C_1$-$C_7$ haloalkoxy, $C_3$-$C_9$ cycloalkoxy, $C_3$-$C_9$ halocycloalkoxy, $C_2$-$C_8$ alkenyl, $C_2$-$C_8$ haloalkenyl, $C_1$-$C_7$ alkylamino, $C_1$-$C_7$ haloalkylamino, $C_2$-$C_9$ dialkylamino, $C_2$-$C_9$ halodialkylamino, $C_3$-$C_9$ cycloalkylamino or $C_3$-$C_9$ halocycloalkylamino, each substituted or unsubstituted with up to 3 substituents independently selected from $R^8$ or $G^1$; or $R^A$ is $G^1$ or $OG^1$; or $R^A$ is taken together with $R^9$ as $-C(R^I)(R^J)C(=O)-$;

$R^B$ is H, $C_1$-$C_4$ alkoxy, $C_1$-$C_4$ haloalkyl or $C_1$-$C_4$ alkyl; or phenyl substituted or unsubstituted with halogen or $C_1$-$C_4$ alkyl;

$R^C$ is H, $C_1$-$C_4$ alkoxy, $C_1$-$C_4$ haloalkyl or $C_1$-$C_4$ alkyl; or phenyl substituted or unsubstituted with halogen or $C_1$-$C_4$ alkyl;

$R^D$ is H, $C_1$-$C_4$ alkyl or $C_2$-$C_4$ alkylcarbonyl;

$R^E$ is H, hydroxy, amino, cyano, formyl, $-C(O)NH_2$, $C_1$-$C_6$ alkyl, $C_1$-$C_6$ haloalkyl, $C_2$-$C_6$ cyanoalkyl, $C_3$-$C_6$ cycloalkyl, $C_4$-$C_8$ cycloalkylalkyl, $C_2$-$C_8$ alkoxyalkyl, $C_3$-$C_8$ alkoxyalkoxyalkyl, $C_2$-$C_8$ haloalkoxyalkyl, $C_2$-$C_8$ alkenyl, $C_2$-$C_8$ haloalkenyl, $C_2$-$C_8$ alkenylalkyl, $C_2$-$C_8$ haloalkenylalkyl, $C_2$-$C_8$ alkylcarbonyl, $C_2$-$C_8$ haloalkylcarbonyl, $C_4$-$C_{10}$ cycloalkylcarbonyl, $C_5$-$C_{10}$ cycloalkylcarbonylalkyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl or $C_2$-$C_8$ dialkylaminosulfonyl; or $G^E$ or $W^EG^E$;

$R^F$ is H, formyl, $-C(O)NH_2$, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, —P(=O)(OH)$_2$, $C_1$-$C_6$ dialkylphosphoryl, $C_1$-$C_6$ haloalkylphosphoryl, $C_3$-$C_8$ cycloalkylphosphoryl, $C_2$-$C_8$ dialkoxyphosphoryl, $C_6$-$C_{14}$ dicycloalkoxyphosphoryl, $C_8$-$C_{16}$ dicycloalkylalkoxyphosphoryl, $C_2$-$C_{12}$ bis(alkylamino)phosphoryl, $C_4$-$C_{24}$ bis(dialkylamino)phosphoryl; or $G^F$ or $W^F G^F$;

$R^G$ is formyl, —C(O)NH$_2$, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, —P(=O)(OH)$_2$, $C_1$-$C_6$ dialkylphosphoryl, $C_1$-$C_6$ haloalkylphosphoryl, $C_3$-$C_8$ cycloalkylphosphoryl, $C_2$-$C_8$ dialkoxyphosphoryl, $C_6$-$C_{14}$ dicycloalkoxyphosphoryl, $C_8$-$C_{16}$ dicycloalkylalkoxyphosphoryl, $C_2$-$C_{12}$ bis(alkylamino)phosphoryl, $C_4$-$C_{24}$ bis(dialkylamino)phosphoryl; or phenyl substituted or unsubstituted with $R^{16}$; or $W^G G^G$;

$R^I$ is H, $C_1$-$C_4$ alkoxy, $C_1$-$C_4$ haloalkyl or $C_1$-$C_4$ alkyl; or phenyl substituted or unsubstituted with halogen or $C_1$-$C_4$ alkyl;

$R^J$ is H, $C_1$-$C_4$ alkoxy, $C_1$-$C_4$ haloalkyl or $C_1$-$C_4$ alkyl; or phenyl substituted or unsubstituted with halogen or $C_1$-$C_4$ alkyl;

$Q^1$ is a phenyl ring or a naphthalenyl ring system, each ring or ring system substituted or unsubstituted with up to 5 substituents independently selected from $R^7$; or a 4- to 7-membered heterocyclic ring; or an 8- to 10-membered bicyclic ring system, each ring or ring system containing ring members selected from carbon atoms and 1 to 5 heteroatoms independently selected from up to 2 O, up to 2 S and up to 5 N atoms, wherein up to 3 carbon ring members are independently selected from C(=O) and C(=S), and the sulfur atom ring members are independently selected from S(=O)$_u$ (=NR$^{14}$)$_v$, each ring or ring system substituted or unsubstituted with up to 5 substituents independently selected from $R^{10}$ on carbon atom ring members and selected from $R^{12}$ on nitrogen atom ring members; or $Q^2$ is a phenyl ring or a naphthalenyl ring system, each ring or ring system substituted or unsubstituted with up to 5 substituents independently selected from $R^{10}$; or a 4- to 7-membered heterocyclic ring; or an 8- to 10-membered bicyclic ring system, each ring or ring system containing ring members selected from carbon atoms and 1 to 4 heteroatoms independently selected from up to 2 O, up to 2 S and up to 5 N atoms, wherein up to 3 carbon ring members are independently selected from C(=O) and C(=S), and the sulfur atom ring members are independently selected from S(=O)$_u$ (=NR$^{14}$)$_v$, each ring or ring system substituted or unsubstituted with up to 5 substituents independently selected from $R^{11}$ on carbon atom ring members and selected from $R^{13}$ on nitrogen atom ring members; or J is —CR$^2$R$^3$—, —CR$^2$R$^3$—CR$^4$R$^5$—, —NR$^6$— or —O—;

$Y^1$ and $Y^2$ are each independently O, S or NR$^{15}$;

$R^1$ is H, hydroxy, amino, cyano, formyl, $C_3$-$C_8$ alkylcarbonylalkyl, —C(C$_1$-C$_4$ alkyl)=N—O(C$_1$-C$_4$ alkyl), —C(O)NH$_2$, $C_1$-$C_6$ alkyl, $C_1$-$C_6$ haloalkyl, $C_2$-$C_6$ alkenyl, $C_2$-$C_6$ alkynyl, $C_2$-$C_6$ cyanoalkyl, $C_3$-$C_6$ cycloalkyl, $C_3$-$C_8$ cycloalkenyl, $C_4$-$C_8$ cycloalkylalkyl, $C_2$-$C_8$ alkoxyalkyl, $C_3$-$C_8$ alkoxyalkoxyalkyl, $C_2$-$C_8$ haloalkoxyalkyl, $C_2$-$C_8$ haloalkenylalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_5$-$C_{10}$ cycloalkylcarbonylalkyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl; or —CPh=N—O(C$_1$-C$_4$ alkyl), each substituted or unsubstituted on ring members with up to 5 substituents independently selected from $R^{13}$; or $G^1$;

$R^2$ and $R^3$ are each independently H, halogen, hydroxy, $C_1$-$C_4$ alkyl, $C_1$-$C_4$ haloalkyl or $C_1$-$C_4$ alkoxy; or $R^2$ and $R^3$ are taken together with the carbon atom to which they are bonded to form a $C_3$-$C_7$ cycloalkyl ring;

$R^4$ and $R^5$ are each independently H, halogen, hydroxy, $C_1$-$C_4$ alkyl, $C_1$-$C_4$ haloalkyl or $C_1$-$C_4$ alkoxy;

$R^6$ is $C_1$-$C_6$ alkyl, $C_2$-$C_6$ alkenyl, $C_3$-$C_6$ alkynyl or $C_1$-$C_6$ alkoxy; or $R^1$ and $R^6$ are taken together as $C_3$-$C_6$ alkylene or —CH$_2$OCH$_2$—;

$R^7$ is H, halogen, hydroxy, $C_1$-$C_4$ alkoxy, $C_1$-$C_4$ haloalkyl or $C_1$-$C_4$ alkyl;

each $R^8$ is independently cyano, hydroxy, amino, nitro, —CHO, —C(=O)OH, —C(=O)NH$_2$, —SO$_2$NH$_2$, $C_2$-$C_6$ alkenyl, $C_2$-$C_6$ alkynyl, $C_2$-$C_8$ alkylcarbonyl, $C_2$-$C_8$ haloalkylcarbonyl, $C_2$-$C_8$ alkoxycarbonyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_1$-$C_6$ alkoxy, $C_1$-$C_6$ haloalkoxy, $C_2$-$C_8$ alkylcarbonyloxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylaminosulfonyl, $C_2$-$C_8$ dialkylaminosulfonyl, $C_3$-$C_{10}$ trialkylsilyl, $C_1$-$C_6$ alkylamino, $C_2$-$C_8$ dialkylamino, $C_2$-$C_8$ alkylcarbonylamino or $C_1$-$C_6$ alkylsulfonylamino;

$R^9$ is H, hydroxy, amino, $C_1$-$C_6$ alkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl or $C_3$-$C_{10}$ trialkylsilyl or $G^1$;

each $R^{10}$ and $R^{11}$ is independently halogen, hydroxy, cyano, nitro, amino, $C_1$-$C_8$ alkyl, $C_1$-$C_8$ cyanoalkyl, $C_1$-$C_8$ cyanoalkoxy, $C_1$-$C_8$ haloalkyl, $C_1$-$C_8$ hydroxyalkyl, $C_1$-$C_8$ nitroalkyl, $C_2$-$C_8$ alkenyl, $C_2$-$C_8$ haloalkenyl, $C_2$-$C_8$ nitroalkenyl, $C_2$-$C_8$ alkynyl, $C_2$-$C_8$ haloalkynyl, $C_2$-$C_8$ alkoxyalkyl, $C_3$-$C_8$ alkoxyalkoxyalkyl, $C_2$-$C_8$ haloalkoxyalkyl, $C_2$-$C_8$ haloalkoxyhaloalkoxy, $C_3$-$C_6$ cycloalkyl, cyclopropylmethyl, 1-methylcyclopropyl, 2-methylcyclopropyl, $C_4$-$C_{10}$ cycloalkylalkyl, $C_4$-$C_{10}$ halocycloalkylalkyl, $C_5$-$C_{12}$ alkylcycloalkylalkyl, $C_5$-$C_{12}$ cycloalkylalkenyl, $C_5$-$C_{12}$ cycloalkylalkynyl, $C_3$-$C_8$ cycloalkyl, $C_3$-$C_8$ halocycloalkyl, $C_4$-$C_{10}$ alkylcycloalkyl, $C_6$-$C_{12}$ cycloalkylcycloalkyl, $C_3$-$C_8$ cycloalkenyl, $C_3$-$C_8$ halocycloalkenyl, $C_2$-$C_8$ haloalkoxyalkoxy, $C_2$-$C_8$ alkoxyalkoxy, $C_4$-$C_{10}$ cycloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylamino, $C_2$-$C_8$ dialkylamino, $C_2$-$C_8$ halodialkylamino, $C_2$-$C_8$ alkylaminoalkyl, $C_2$-$C_8$ haloalkylaminoalkyl, $C_4$-$C_{10}$ cycloalkylaminoalkyl, $C_3$-$C_{10}$ dialkylaminoalkyl, —CHO, $C_2$-$C_8$ alkylcarbonyl, $C_2$-$C_8$ haloalkylcarbonyl, $C_4$-$C_{10}$ cycloalkylcarbonyl, —C(=O)OH, $C_2$-$C_8$ alkoxycarbonyl, $C_2$-$C_8$ haloalkoxycarbonyl, $C_4$-$C_{10}$ cycloalkoxycarbonyl, $C_5$-$C_{12}$ cycloalkylalkoxycarbonyl, —C(=O)NH$_2$, $C_2$-$C_8$ alkylaminocarbonyl, $C_4$-$C_{10}$ cycloalkylaminocarbonyl, $C_3$-$C_{10}$ dialkylaminocarbonyl, $C_1$-$C_8$ alkoxy, $C_1$-$C_8$ haloalkoxy, $C_2$-$C_8$ alkenyloxy, $C_2$-$C_8$ haloalkenyloxy, $C_3$-$C_8$ alkynyloxy, $C_3$-$C_8$ haloalkynyloxy, $C_3$-$C_8$ cycloalkoxy, $C_3$-$C_8$ halocycloalkoxy, $C_4$-$C_{10}$ cycloalkylalkoxy, $C_3$-$C_{10}$ alkylcarbonylalkoxy, $C_2$-$C_8$ alkylcarbonyloxy, $C_2$-$C_8$ haloalkylcarbonyloxy, $C_4$-$C_{10}$ cycloalkylcarbonyloxy, $C_1$-$C_8$ alkylsulfonyloxy, $C_1$-$C_8$ haloalkylsulfonyloxy, $C_1$-$C_8$ alkylthio, $C_1$-$C_8$ haloalkylthio, $C_3$-$C_8$ cycloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, $C_3$-$C_8$ cycloalkylsulfonyl, formylamino, $C_2$-$C_8$ alkylcarbonylamino, $C_2$-$C_8$ haloalkylcarbonylamino, $C_3$-$C_8$ cycloalkylamino, $C_2$-$C_8$ alkoxycarbonylamino, $C_1$-$C_6$ alkylsulfonylamino, $C_1$-$C_6$ haloalkylsulfonylamino, —SF$_5$, —SCN, SO$_2$NH$_2$, $C_3$-$C_{12}$ trialkylsilyl, $C_4$-$C_{12}$ trialkylsilylalkyl or $C_4$-$C_{12}$ trialkylsilylalkoxy; or G$^2$; or R$^{20}$S(=O)=N—, R$^{20}$S(=O)$_2$NR$^{19}$—C(=O)— or R$^{20}$(R$^{19}$N=)$_q$S(=O)$_p$—, wherein the free bond projecting to the right indicates the connecting point to Q$^1$; or each R$^{12}$ and R$^{13}$ is independently cyano, $C_1$-$C_3$ alkyl, $C_1$-$C_8$ hydroxyalkyl, $C_2$-$C_3$ alkenyl, $C_2$-$C_3$ alkynyl, $C_3$-$C_6$ cycloalkyl, $C_2$-$C_3$ alkoxyalkyl, $C_1$-$C_3$ alkoxy, $C_2$-$C_3$ alkylcarbonyl, $C_2$-$C_3$ alkoxycarbonyl, $C_2$-$C_3$ alkylaminoalkyl or $C_3$-$C_4$ dialkylaminoalkyl;

each R$^{14}$ is independently H, cyano, $C_2$-$C_3$ alkylcarbonyl or $C_2$-$C_3$ haloalkylcarbonyl;

each R$^{15}$ is independently H, cyano, hydroxy, CHO, $C_1$-$C_4$ alkyl, $C_1$-$C_4$ haloalkyl, $C_1$-$C_4$ alkoxy, $C_2$-$C_6$ alkylcarbonyl, $C_2$-$C_6$ haloalkylcarbonyl, —(C=O)CH$_3$ or —(C=O)CF$_3$;

each G$^1$ is independently phenyl; or a 5- or 6-membered heterocyclic ring, each substituted or unsubstituted on ring members with up to 5 substituents independently selected from R$^{17}$;

each W$^E$, W$^F$ and W$^G$ is independently —C(=O)—, —C(=O)O—, —C(=O)NH— or —S(=O)$_2$—;

each G$^E$, G$^F$ and G$^G$ is independently phenyl substituted or unsubstituted with R$^{16}$; or a 5- or 6-membered heterocyclic ring, each heterocyclic ring substituted or unsubstituted on ring members with up to 5 substituents independently selected from R$^{16}$;

each G$^2$ is independently phenyl, phenylmethyl, pyridinylmethyl, phenylcarbonyl, phenoxy, phenylethynyl, phenylsulfonyl or a 5- or 6-membered heterocyclic ring, each substituted or unsubstituted on ring members with up to 5 substituents independently selected from R$^{18}$;

each R$^{16}$, R$^{17}$ and R$^{18}$ is independently halogen, cyano, hydroxy, amino, nitro, —CHO, —C(=O)OH, —C(=O)NH$_2$, —SO$_2$NH$_2$, $C_1$-$C_6$ alkyl, $C_1$-$C_6$ haloalkyl, $C_2$-$C_6$ alkenyl, $C_2$-$C_6$ alkynyl, $C_2$-$C_8$ alkylcarbonyl, $C_2$-$C_8$ haloalkylcarbonyl, $C_2$-$C_8$ alkoxycarbonyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_1$-$C_6$ alkoxy, $C_1$-$C_6$ haloalkoxy, $C_2$-$C_8$ alkylcarbonyloxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylaminosulfonyl, $C_2$-$C_8$ dialkylaminosulfonyl, $C_3$-$C_{10}$ trialkylsilyl, $C_1$-$C_6$ alkylamino, $C_2$-$C_8$ dialkylamino, $C_2$-$C_8$ alkylcarbonylamino, $C_1$-$C_6$ alkylsulfonylamino, phenyl, pyridinyl or thienyl;

each R$^{19}$ is independently H, cyano, $C_2$-$C_3$ alkylcarbonyl or $C_2$-$C_3$ haloalkylcarbonyl;

each R$^{20}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_1$-$C_6$ alkoxy or $C_3$-$C_{10}$ trialkylsilyl; or G$^1$;

each u and v are independently 0, 1 or 2 in each instance of S(=O)$_u$(=NR$^{14}$)$_v$, provided that the sum of u and v is 0, 1 or 2; and each p and q are independently 0, 1 or 2 in each instance of R$^{20}$(R$^{19}$N=)$_q$S(=O)$_p$—, provided that the sum of u and v is 0, 1 or 2 and when p is 0, q is other than 1 or 2.

2. The compound of claim 1 wherein
R$^A$ is $C_1$-$C_7$ alkyl, $C_1$-$C_7$ haloalkyl, $C_3$-$C_9$ cycloalkyl, $C_1$-$C_7$ alkoxy or $C_1$-$C_7$ haloalkoxy, $C_3$-$C_9$ cycloalkoxy, each substituted or unsubstituted with up to 2 substituents independently selected from R$^8$ or G$^1$; or
R$^A$ is G$^1$;
R$^B$ is H, $C_1$-$C_4$ alkoxy, $C_1$-$C_4$ haloalkyl or $C_1$-$C_4$ alkyl;
R$^C$ is H, $C_1$-$C_4$ alkoxy, $C_1$-$C_4$ haloalkyl or $C_1$-$C_4$ alkyl;
R$^D$ is H, $C_1$-$C_3$ alkyl or $C_2$-$C_3$ alkylcarbonyl;
R$^E$ is H, hydroxy, amino, cyano, formyl, —C(O)NH$_2$, $C_1$-$C_6$ alkyl, $C_1$-$C_6$ haloalkyl, $C_2$-$C_6$ cyanoalkyl, $C_3$-$C_6$ cycloalkyl, $C_4$-$C_8$ cycloalkylalkyl, $C_2$-$C_8$ alkoxyalkyl, $C_3$-$C_8$ alkoxyalkoxyalkyl, $C_2$-$C_8$ haloalkoxyalkyl, $C_2$-$C_8$ alkenyl, $C_2$-$C_8$ haloalkenyl, $C_2$-$C_8$ alkenylalkyl, $C_2$-$C_8$ haloalkenylalkyl, $C_2$-$C_8$ alkylcarbonyl, $C_2$-$C_8$ haloalkylcarbonyl, $C_4$-$C_{10}$ cycloalkylcarbonyl, $C_5$-$C_{10}$ cycloalkylcarbonylalkyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl or $C_2$-$C_8$ dialkylaminosulfonyl;
R$^F$ is formyl, —C(O)NH$_2$, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, —P(=O)(OH)$_2$, $C_1$-$C_6$ dialkylphosphoryl, $C_1$-$C_6$ haloalkylphosphoryl, $C_3$-$C_8$ cycloalkylphosphoryl, $C_2$-$C_8$ dialkoxyphosphoryl, $C_6$-$C_{14}$ dicycloalkoxyphosphoryl, $C_8$-$C_{16}$ dicycloalkylalkoxyphosphoryl, $C_2$-$C_{12}$ bis(alkylamino)phosphoryl, $C_4$-$C_{24}$ bis(dialkylamino)phosphoryl; or phenyl substituted or unsubstituted with $R^{16}$;

$R^G$ is formyl, —C(O)NH$_2$, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl or $C_1$-$C_6$ alkylaminosulfonyl;

$Q^1$ is a phenyl ring or a naphthalenyl ring system, each ring or ring system substituted or unsubstituted with up to 5 substituents independently selected from $R^{10}$; or a 5- to 6-membered heterocyclic ring; or an 8- to 10-membered bicyclic ring system, each ring or ring system containing ring members selected from carbon atoms and 1 to 4 heteroatoms independently selected from up to 2 O, up to 2 S and up to 4 N atoms, wherein up to 2 carbon ring members are independently selected from C(=O) and C(=S), and the sulfur atom ring members are independently selected from S(=O)$_u$ (=NR$^{14}$)$_v$, each ring or ring system substituted or unsubstituted with up to 4 substituents independently selected from $R^{10}$ on carbon atom ring members and selected from $R^{12}$ on nitrogen atom ring members;

$Q^2$ is a phenyl ring, each ring substituted or unsubstituted with up to 4 substituents independently selected from $R^{11}$; or a 5- to 6-membered heterocyclic ring; or an 8- to 10-membered bicyclic ring system, each ring or ring system containing ring members selected from carbon atoms and 1 to 4 heteroatoms independently selected from up to 2 O, up to 2 S and up to 4 N atoms, wherein up to 2 carbon ring members are independently selected from C(=O) and C(=S), and the sulfur atom ring members are independently selected from S(=O)$_u$ (=NR$^{14}$)$_v$, each ring or ring system substituted or unsubstituted with up to 4 substituents independently selected from $R^{11}$ on carbon atom ring members and selected from $R^{13}$ on nitrogen atom ring members;

J is —CR$^2$R$^3$—, —CR$^2$R$^3$—CR$^4$R$^5$— or —NR$^6$—;

$Y^1$ and $Y^2$ are each independently O or S;

$R^1$ is H, CHO, $C_3$-$C_8$ alkylcarbonylalkyl, $C_1$-$C_6$ alkyl, $C_1$-$C_6$ haloalkyl, $C_2$-$C_6$ alkenyl, $C_3$-$C_6$ alkynyl, $C_2$-$C_6$ cyanoalkyl, $C_3$-$C_6$ cycloalkyl, $C_4$-$C_8$ cycloalkylalkyl, $C_2$-$C_8$ alkoxyalkyl, $C_3$-$C_8$ alkoxyalkoxyalkyl, $C_2$-$C_8$ haloalkoxyalkyl, $C_2$-$C_8$ alkylthioalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_2$-$C_8$ alkylaminocarbonyl, $C_3$-$C_{10}$ dialkylaminocarbonyl or $C_4$-$C_{10}$ cycloalkylaminocarbonyl;

$R^2$ and $R^3$ are each independently H or $C_1$-$C_4$ alkyl;

$R^4$ and $R^5$ are each independently H, halogen, $C_1$-$C_4$ alkyl or $C_1$-$C_4$ alkoxy;

$R^6$ is H, $C_1$-$C_6$ alkyl or $C_1$-$C_6$ alkoxy;

$R^7$ is H, halogen, $C_1$-$C_4$ alkoxy or $C_1$-$C_4$ alkyl;

each $R^8$ is independently cyano, nitro, —CHO, $C_2$-$C_6$ alkenyl, $C_2$-$C_6$ alkynyl, $C_2$-$C_8$ haloalkylcarbonyl, $C_2$-$C_8$ alkoxycarbonyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_1$-$C_6$ alkoxy, $C_1$-$C_6$ haloalkoxy or $C_2$-$C_8$ alkylcarbonyloxy;

$R^9$ is H, $C_1$-$C_6$ alkyl, $C_2$-$C_8$ alkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_4$-$C_{10}$ cycloalkylcarbonyl, $C_2$-$C_8$ alkoxycarbonyl or $C_4$-$C_{10}$ cycloalkoxycarbonyl;

each $R^{10}$ and $R^{11}$ is halogen, nitro, $C_1$-$C_8$ alkyl, $C_1$-$C_8$ cyanoalkyl, $C_1$-$C_8$ cyanoalkoxy, $C_1$-$C_8$ haloalkyl, $C_1$-$C_8$ nitroalkyl, $C_2$-$C_8$ alkenyl, $C_2$-$C_8$ haloalkenyl, $C_2$-$C_8$ nitroalkenyl, $C_2$-$C_8$ alkoxyalkyl, $C_3$-$C_8$ alkoxyalkoxyalkyl, $C_2$-$C_8$ haloalkoxyalkyl, $C_2$-$C_8$ haloalkoxyhaloalkoxy, $C_4$-$C_{10}$ cycloalkylalkyl, $C_4$-$C_{10}$ halocycloalkylalkyl, $C_5$-$C_{12}$ alkylcycloalkylalkyl, $C_5$-$C_{12}$ cycloalkylalkenyl, $C_3$-$C_8$ cycloalkyl, $C_3$-$C_8$ halocycloalkyl, $C_4$-$C_{10}$ alkylcycloalkyl, $C_6$-$C_{12}$ cycloalkylcycloalkyl, $C_3$-$C_8$ cycloalkenyl, $C_3$-$C_8$ halocycloalkenyl, $C_2$-$C_8$ haloalkoxyalkoxy, $C_2$-$C_8$ alkoxyalkoxy, $C_4$-$C_{10}$ cycloalkoxyalkyl, $C_2$-$C_8$ alkylcarbonyl, $C_2$-$C_8$ haloalkylcarbonyl, $C_4$-$C_{10}$ cycloalkylcarbonyl, —C(=O)OH, $C_2$-$C_8$ alkoxycarbonyl, $C_2$-$C_8$ haloalkoxycarbonyl, $C_4$-$C_{10}$ cycloalkoxycarbonyl, $C_5$-$C_{12}$ cycloalkylalkoxycarbonyl, —C(=O)NH$_2$, $C_1$-$C_8$ alkoxy, $C_1$-$C_8$ haloalkoxy, $C_2$-$C_8$ alkenyloxy, $C_2$-$C_8$ haloalkenyloxy, $C_3$-$C_8$ cycloalkoxy, $C_3$-$C_8$ halocycloalkoxy, $C_4$-$C_{10}$ cycloalkylalkoxy, $C_3$-$C_{10}$ alkylcarbonylalkoxy, $C_2$-$C_8$ alkylcarbonyloxy, $C_2$-$C_8$ haloalkylcarbonyloxy, $C_4$-$C_{10}$ cycloalkylcarbonyloxy, $C_1$-$C_8$ alkylsulfonyloxy, $C_1$-$C_8$ haloalkylsulfonyloxy, $C_1$-$C_8$ alkylsulfonyl, $C_1$-$C_8$ haloalkylsulfonyl, $C_3$-$C_8$ cycloalkylsulfonyl;

each $G^1$ is independently phenyl; or a 6-membered heterocyclic ring, each substituted or unsubstituted on ring members with up to 4 substituents independently selected from $R^{17}$;

each $R^{16}$ and $R^{17}$ is independently halogen, cyano, hydroxy, amino, nitro, —CHO, —C(=O)OH, —C(=O)NH$_2$, —SO$_2$NH$_2$, $C_1$-$C_6$ alkyl, $C_1$-$C_6$ haloalkyl, $C_2$-$C_6$ alkenyl, $C_2$-$C_6$ alkynyl, $C_2$-$C_8$ alkylcarbonyl, $C_1$-$C_8$ hydroxyalkyl, $C_2$-$C_8$ haloalkylcarbonyl, $C_2$-$C_6$ alkoxyalkyl, $C_2$-$C_6$ alkylaminoalkyl, $C_2$-$C_8$ alkoxycarbonyl, $C_3$-$C_8$ cycloalkyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_3$-$C_8$ dialkylaminoalkyl, $C_1$-$C_6$ alkoxy, $C_1$-$C_6$ haloalkoxy, $C_2$-$C_8$ alkylcarbonyloxy or $C_1$-$C_6$ alkylthio; and provided the sum of u and v is 2.

3. The compound of claim 2 wherein

L is selected from L-1, L-2 or L-3;

$R^A$ is $C_1$-$C_7$ alkyl, $C_1$-$C_7$ haloalkyl, $C_1$-$C_7$ alkoxy or $C_1$-$C_7$ haloalkoxy; each substituted or unsubstituted with up to 2 substituents independently selected from $R^8$; or $R^A$ is $G^1$;

$R^B$ is H, —OCH$_3$, CF$_3$ or CH$_3$;

$R^C$ is H, $C_1$-$C_2$ alkoxy or $C_1$-$C_2$ alkyl;

$R^D$ is H, CH$_3$, CH$_2$CH$_3$ or —C(=O)CH$_3$ CH$_2$CH$_3$;

$R^E$ is H, hydroxy, amino, cyano, formyl, —C(O)NH$_2$, $C_1$-$C_6$ alkyl, $C_3$-$C_6$ cycloalkyl, $C_4$-$C_8$ cycloalkylalkyl, $C_2$-$C_8$ alkoxyalkyl, $C_3$-$C_8$ alkoxyalkoxyalkyl, $C_2$-$C_8$ alkylcarbonyl, $C_4$-$C_{10}$ cycloalkylcarbonyl, $C_5$-$C_{10}$ cycloalkylcarbonylalkyl, $C_2$-$C_8$ alkoxycarbonyl, $C_4$-$C_{10}$ cycloalkoxycarbonyl, $C_1$-$C_6$ alkylsulfonyl;

$R^F$ is $C_2$-$C_8$ alkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkylsulfonyl, $C_1$-$C_6$ haloalkylsulfonyl, $C_3$-$C_8$ cycloalkylsulfonyl or $C_1$-$C_6$ alkylaminosulfonyl; or phenyl substituted or unsubstituted with $R^{16}$;

$R^G$ is formyl, $C_2$-$C_8$ alkylcarbonyl, $C_2$-$C_8$ alkoxycarbonyl, $C_4$-$C_{10}$ cycloalkoxycarbonyl, $C_2$-$C_8$ alkylaminocarbonyl, $C_4$-$C_{10}$ cycloalkylaminocarbonyl, $C_1$-$C_6$ alkylsulfonyl, $C_1$-$C_6$ haloalkylsulfonyl, $C_3$-$C_8$ cycloalkylsulfonyl or $C_1$-$C_6$ alkylaminosulfonyl;

each $R^8$ is independently $C_2$-$C_6$ alkenyl, $C_1$-$C_6$ alkoxy or $C_1$-$C_6$ haloalkoxy;

J is —$CR^2R^3$— or —$CR^2R^3$—$CR^4R^5$—;

$Y^1$ and $Y^2$ are each independently O;

$R^1$ is H, $C_3$-$C_8$ alkylcarbonylalkyl, $C_1$-$C_6$ alkyl, $C_1$-$C_6$ haloalkyl, $C_2$-$C_6$ cyanoalkyl, $C_3$-$C_6$ cycloalkyl, $C_4$-$C_8$ cycloalkylalkyl, $C_2$-$C_8$ alkoxyalkyl, $C_2$-$C_8$ haloalkoxyalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl or $C_2$-$C_8$ haloalkoxycarbonyl;

$Q^1$ is a phenyl ring substituted or unsubstituted with up to 4 substituents independently selected from $R^{10}$; or a 5- to 6-membered heterocyclic ring, each ring containing ring members selected from carbon atoms and 1 to 4 heteroatoms independently selected from up to 2 O, up to 2 S and up to 4 N atoms, each ring substituted or unsubstituted with up to 4 substituents independently selected from $R^{10}$ on carbon atom ring members and selected from $R^{12}$ on nitrogen atom ring members;

$Q^2$ is a phenyl ring, substituted or unsubstituted with up to 4 substituents independently selected from $R^{11}$; or a 5- to 6-membered heterocyclic ring; or an 8- to 10-membered bicyclic ring system, each ring or ring system containing ring members selected from carbon atoms and 1 to 4 heteroatoms independently selected from up to 2 O, up to 2 S and up to 4 N atoms, wherein up to 2 carbon ring members are independently selected from C(=O) and C(=S), and the sulfur atom ring members are independently selected from S(=O)$_u$(=NR$^{14}$)$_v$, each ring or ring system substituted or unsubstituted with up to 4 substituents independently selected from $R^{11}$ on carbon atom ring members and selected from $R^{13}$ on nitrogen atom ring members;

$R^2$ and $R^3$ are each independently H or $CH_3$;

$R^4$ and $R^5$ are each independently H, halogen or $C_1$-$C_4$ alkyl;

$R^7$ is H, F, Cl or $CH_3$;

$R^9$ is H, $C_1$-$C_6$ alkyl, $C_2$-$C_8$ alkoxyalkyl, $C_2$-$C_8$ alkylcarbonyl or $C_2$-$C_8$ alkoxycarbonyl;

each $R^{10}$ and $R^{11}$ is independently halogen, $C_1$-$C_8$ alkyl, $C_1$-$C_8$ haloalkyl, $C_2$-$C_8$ alkoxyalkyl, $C_3$-$C_8$ alkoxyalkoxyalkyl, $C_4$-$C_{10}$ cycloalkylalkyl, $C_5$-$C_{12}$ alkylcycloalkylalkyl, $C_3$-$C_8$ cycloalkyl, $C_3$-$C_8$ halocycloalkyl, $C_6$-$C_{12}$ cycloalkylcycloalkyl, $C_3$-$C_8$ halocycloalkenyl, $C_2$-$C_8$ haloalkoxyalkoxy, $C_2$-$C_8$ alkoxyalkoxy, $C_4$-$C_{10}$ cycloalkoxyalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_4$-$C_{10}$ cycloalkoxycarbonyl, $C_5$-$C_{12}$ cycloalkylalkoxycarbonyl, $C_1$-$C_8$ alkoxy, $C_1$-$C_8$ haloalkoxy, $C_2$-$C_8$ haloalkenyloxy, $C_3$-$C_8$ cycloalkoxy, $C_3$-$C_8$ halocycloalkoxy, $C_4$-$C_{10}$ cycloalkylalkoxy, $C_3$-$C_{10}$ alkylcarbonylalkoxy or $C_2$-$C_8$ haloalkylcarbonyloxy;

each $R^{12}$ and $R^{13}$ is independently $C_1$-$C_3$ alkyl, $C_3$-$C_6$ cycloalkyl or $C_2$-$C_3$ alkylcarbonyl;

each $R^{14}$ is independently H;

$R^{15}$ is H, $CH_3$, —(C=O)$CH_3$ or —(C=O)$CF_3$;

each $G^1$ is independently phenyl substituted or unsubstituted on ring members with up to 3 substituents independently selected from $R^{17}$; and each $R^{16}$ and $R^{17}$ is independently halogen, cyano, hydroxy, amino, nitro, —CHO, —C(=O)OH, —C(=O)$NH_2$, —$SO_2NH_2$, $C_1$-$C_6$ alkyl or $C_1$-$C_6$ haloalkyl.

4. The compound of claim 3 wherein

L is selected from L-1 or L-2;

$R^A$ is $C_1$-$C_7$ alkyl or $C_1$-$C_7$ alkoxy; each substituted or unsubstituted with up to 2 substituents independently selected from $R^8$;

$R^B$ is H, —$OCH_3$ or $CH_3$;

$R^C$ is H or $CH_3$;

$R^D$ is $CH_3$ or $CH_2CH_3$;

$R^E$ is H, $C_1$-$C_6$ alkyl, $C_3$-$C_6$ cycloalkyl, $C_4$-$C_8$ cycloalkylalkyl, $C_2$-$C_8$ alkoxyalkyl, $C_2$-$C_8$ alkylcarbonyl, $C_2$-$C_8$ alkoxycarbonyl, $C_4$-$C_{10}$ cycloalkoxycarbonyl, $C_1$-$C_6$ alkylsulfonyl;

each $R^8$ is independently $C_1$-$C_6$ alkoxy or $C_1$-$C_6$ haloalkoxy;

J is —$CR^2R^3$—;

$Y^1$ and $Y^2$ are each independently O;

$R^1$ is H, $C_1$-$C_6$ alkyl, $C_1$-$C_6$ haloalkyl, $C_2$-$C_6$ cyanoalkyl, $C_3$-$C_6$ cycloalkyl, $C_4$-$C_8$ cycloalkylalkyl, $C_2$-$C_8$ alkoxyalkyl, $C_2$-$C_8$ haloalkoxyalkyl or $C_2$-$C_8$ alkoxycarbonyl;

$Q^1$ is a phenyl ring substituted or unsubstituted with up to 4 substituents independently selected from $R^{10}$;

$Q^2$ is a phenyl ring, substituted or unsubstituted with up to 4 substituents independently selected from $R^{11}$; or a 5- to 6-membered heterocyclic ring containing ring members selected from carbon atoms and 1 to 4 heteroatoms independently selected from up to 4 N atoms, wherein up to 2 carbon ring members are independently selected from C(=O) and C(=S), each ring or ring system substituted or unsubstituted with up to 4 substituents independently selected from $R^{11}$ on carbon atom ring members and selected from $R^{13}$ on nitrogen atom ring members;

$R^2$ and $R^3$ are each independently H;

$R^7$ is H or $CH_3$;

$R^9$ is H, $C_1$-$C_6$ alkyl or $C_2$-$C_8$ alkoxycarbonyl;

each $R^{10}$ and $R^{11}$ is independently halogen, $C_1$-$C_8$ alkyl, $C_1$-$C_8$ haloalkyl, $C_2$-$C_8$ alkoxyalkyl, $C_4$-$C_{10}$ cycloalkylalkyl, $C_5$-$C_{12}$ alkylcycloalkylalkyl, $C_3$-$C_8$ cycloalkyl, $C_3$-$C_8$ halocycloalkyl, $C_2$-$C_8$ haloalkoxyalkoxy, $C_1$-$C_8$ alkoxy, $C_1$-$C_8$ haloalkoxy or $C_2$-$C_8$ alkoxyalkoxy; and each $R^{12}$ and $R^{13}$ is independently $C_1$-$C_3$ alkyl or $C_2$-$C_3$ alkylcarbonyl.

5. The compound of claim 4 wherein

L is selected from L-1;

$R^A$ is $C_1$-$C_3$ alkyl substituted or unsubstituted with up to 2 substituents independently selected from $R^8$;

each $R^8$ is independently $C_1$-$C_6$ alkoxy;

$R^1$ is H, $C_1$-$C_6$ alkyl, $C_3$-$C_6$ cycloalkyl, $C_4$-$C_8$ cycloalkylalkyl or $C_2$-$C_8$ alkoxyalkyl;

$Q^1$ is a phenyl ring substituted or unsubstituted with up to 3 substituents independently selected from $R^{10}$;

$Q^2$ is a phenyl ring, substituted or unsubstituted with up to 4 substituents independently selected from $R^{11}$;

$R^7$ is H;

$R^9$ is H, $CH_3$ or —C(=O)$CH_3$; and each $R^{10}$ and $R^{11}$ is independently halogen, $C_1$-$C_8$ alkyl, $C_1$-$C_8$ haloalkyl, $C_3$-$C_8$ cycloalkyl, $C_1$-$C_8$ alkoxy or $C_1$-$C_8$ haloalkoxy.

6. The compound of claim 4 wherein
L is selected from L-1;
$R^A$ is $C_1$-$C_3$ alkoxy, substituted or unsubstituted with up to 2 substituents independently selected from $R^8$;
each $R^8$ is independently $C_1$-$C_6$ alkoxy;
$R^1$ is H, $CH_3$, $CH_2CH_3$, cyclopropyl, cyclopropylmethyl or $CH_2OCH_3$;
$Q^1$ is a phenyl ring substituted or unsubstituted with up to 2 substituents independently selected from $R^{10}$;
$Q^2$ is a phenyl ring, substituted or unsubstituted with up to 3 substituents independently selected from $R^{11}$;
$R^7$ is H;
$R^9$ is H; and
each $R^{10}$ and $R^{11}$ is independently halogen, $C_1$-$C_8$ alkyl, $C_1$-$C_8$ haloalkyl, $C_1$-$C_8$ alkoxy or $C_1$-$C_8$ haloalkoxy.

7. A compound of claim 1 selected from the group consisting of
(3S,4R)—N-(2,3-difluorophenyl)-3-(hydroxymethyl)-1-methyl-2-oxo-4-[4-(trifluoromethyl)-3-pyrrolidinecarboxamide (cis);
(3R,4S)—N-(2,3-difluorophenyl)-3-(hydroxymethyl)-1-methyl-2-oxo-4-[4-(trifluoromethyl)-3-pyrrolidinecarboxamide (trans);
(3S,4R)-3-[(acetyloxy)methyl]-N-(2,3-difluorophenyl)-1-methyl-2-oxo-4-[4-(trifluoromethyl)-3-pyrrolidinenecarboxamide; and
(3S,4R)-3-acetyl-N-(2,3-difluorophenyl)-1-methyl-2-oxo-4-[4-(trifluoromethyl)-3-pyrrolidinecarboxamide.

8. A herbicidal composition comprising a compound of claim 1 and at least one component selected from the group consisting of surfactants, solid diluents and liquid diluents.

9. A herbicidal composition comprising a compound of claim 1, at least one additional active ingredient selected from the group consisting of other herbicides and herbicide safeners, and at least one component selected from the group consisting of surfactants, solid diluents and liquid diluents.

10. A herbicidal mixture comprising (a) a compound of claim 1, and (b) at least one additional active ingredient selected from (b1) photosystem II inhibitors, (b2) acetohydroxy acid synthase (AHAS) inhibitors, (b3) acetyl-CoA carboxylase (ACCase) inhibitors, (b4) auxin mimics, (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solenesyltransererase (HST) inhibitors, (b14) cellulose biosynthesis inhibitors, (b15) other herbicides including mitotic disruptors, organic arsenicals, asulam, bromobutide, cinmethylin, cumyluron, dazomet, difenzoquat, dymron, etobenzanid, flurenol, fosamine, fosamine-ammonium, hydantocidin, metam, methyldymron, oleic acid, oxaziclomefone, pelargonic acid and pyributicarb, and (b16) herbicide safeners; and salts of compounds of (b1) through (b16).

11. A method for controlling the growth of undesired vegetation comprising contacting the vegetation or its environment with a herbicidally effective amount of a compound of claim 1.

\* \* \* \* \*